(12) United States Patent
Fife et al.

(10) Patent No.: US 8,741,680 B2
(45) Date of Patent: *Jun. 3, 2014

(54) TWO-TRANSISTOR PIXEL ARRAY

(71) Applicant: Life Technologies Corporation, Carlsbad, CA (US)

(72) Inventors: Keith G. Fife, Palo Alto, CA (US); Kim L. Johnson, Carlsbad, CA (US); Mark James Milgrew, Branford, CT (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/849,343

(22) Filed: Mar. 22, 2013

(65) Prior Publication Data

US 2013/0228829 A1 Sep. 5, 2013

Related U.S. Application Data

(63) Continuation of application No. 13/174,222, filed on Jun. 30, 2011, now Pat. No. 8,415,177.

(60) Provisional application No. 61/360,493, filed on Jun. 30, 2010, provisional application No. 61/360,495, filed on Jul. 1, 2010, provisional application No. 61/361,403, filed on Jul. 3, 2010, provisional application No. 61/365,327, filed on Jul. 17, 2010.

(51) Int. Cl.
*H01L 21/00* (2006.01)

(52) U.S. Cl.
USPC .................................. 438/49; 438/10; 438/14

(58) Field of Classification Search
USPC ................................................ 438/49, 10, 14
See application file for complete search history.

(56) References Cited

U.S. PATENT DOCUMENTS

| | | |
|---|---|---|
| 4,411,741 A | 10/1983 | Janata |
| 4,437,969 A | 3/1984 | Covington et al. |
| 4,490,678 A | 12/1984 | Kuisl et al. |
| 4,641,084 A | 2/1987 | Komatsu |
| 4,660,063 A | 4/1987 | Anthony |
| 4,691,167 A | 9/1987 | Vlekkert et al. |
| 4,701,253 A | 10/1987 | Ligtenberg et al. |
| 4,722,830 A | 2/1988 | Urie et al. |
| 4,743,954 A | 5/1988 | Brown |

(Continued)

FOREIGN PATENT DOCUMENTS

| | | |
|---|---|---|
| CN | 102203282 | 9/2011 |
| DE | 19512117 | 10/1996 |

(Continued)

OTHER PUBLICATIONS

[No Author Listed], "ISFET Wikipedia article", Wikipedia, Last modified Nov. 7, 2006.

(Continued)

*Primary Examiner* — Laura Menz

(57) ABSTRACT

A two-transistor (2T) pixel comprises a chemically-sensitive transistor (ChemFET) and a selection device which is a non-chemically sensitive transistor. A plurality of the 2T pixels may form an array, having a number of rows and a number of columns. The ChemFET can be configured in a source follower or common source readout mode. Both the ChemFET and the non-chemically sensitive transistor can be NMOS or PMOS device.

11 Claims, 27 Drawing Sheets

(56) References Cited

U.S. PATENT DOCUMENTS

| | | |
|---|---|---|
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,971,903 A | 11/1990 | Hyman |
| 5,009,766 A | 4/1991 | Lauks |
| 5,038,192 A | 8/1991 | Bonneau |
| 5,110,441 A | 5/1992 | Kinlen et al. |
| 5,113,870 A | 5/1992 | Rossenfeld |
| 5,138,251 A | 8/1992 | Koshiishi et al. |
| 5,151,759 A | 9/1992 | Vinal |
| 5,164,319 A | 11/1992 | Hafeman et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,490,971 A | 2/1996 | Gifford et al. |
| 5,554,339 A | 9/1996 | Cozzette et al. |
| 5,583,462 A | 12/1996 | Grasshoff |
| 5,593,838 A | 1/1997 | Zanzucchi et al. |
| 5,600,451 A | 2/1997 | Maki |
| 5,631,704 A | 5/1997 | Dickinson et al. |
| 5,637,469 A | 6/1997 | Wilding et al. |
| 5,702,964 A | 12/1997 | Lee |
| 5,793,230 A | 8/1998 | Chu et al. |
| 5,846,708 A | 12/1998 | Hollis et al. |
| 5,911,873 A | 6/1999 | McCarron et al. |
| 5,922,591 A | 7/1999 | Anderson et al. |
| 5,923,421 A | 7/1999 | Rajic et al. |
| 5,958,703 A | 9/1999 | Dower et al. |
| 5,965,452 A | 10/1999 | Kovacs |
| 6,002,299 A | 12/1999 | Thomsen |
| 6,107,032 A | 8/2000 | Kilger et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,262,568 B1 | 7/2001 | Komatsu et al. |
| 6,274,320 B1 | 8/2001 | Rothberg et al. |
| 6,327,410 B1 | 12/2001 | Walt et al. |
| 6,355,431 B1 | 3/2002 | Chee et al. |
| 6,361,671 B1 | 3/2002 | Mathies et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,499,499 B2 | 12/2002 | Dantsker et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,602,702 B1 | 8/2003 | McDevitt et al. |
| 6,605,428 B2 | 8/2003 | Kilger et al. |
| 6,613,513 B1 | 9/2003 | Parce et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,657,269 B2 | 12/2003 | Migliorato et al. |
| 6,682,899 B2 | 1/2004 | Bryan et al. |
| 6,682,936 B2 | 1/2004 | Kovacs |
| 6,700,814 B1 | 3/2004 | Nahas et al. |
| 6,703,660 B2 | 3/2004 | Yitzchaik et al. |
| 6,716,629 B2 | 4/2004 | Hess et al. |
| 6,762,022 B2 | 7/2004 | Makarov et al. |
| 6,770,472 B2 | 8/2004 | Manalis et al. |
| 6,780,591 B2 | 8/2004 | Williams et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,841,128 B2 | 1/2005 | Kambara et al. |
| 6,859,570 B2 | 2/2005 | Walt et al. |
| 6,888,194 B2 | 5/2005 | Yoshino |
| 6,898,121 B2 | 5/2005 | Chien et al. |
| 6,919,211 B1 | 7/2005 | Fodor et al. |
| 6,926,865 B2 | 8/2005 | Howard |
| 6,927,045 B2 | 8/2005 | Hadd et al. |
| 6,929,944 B2 | 8/2005 | Matson |
| 6,939,451 B2 | 9/2005 | Zhao et al. |
| 6,953,958 B2 | 10/2005 | Baxter et al. |
| 6,958,216 B2 | 10/2005 | Kelley et al. |
| 6,969,488 B2 | 11/2005 | Bridgham et al. |
| 6,998,274 B2 | 2/2006 | Chee et al. |
| 7,019,305 B2 | 3/2006 | Eversmann et al. |
| 7,022,288 B1 | 4/2006 | Boss |
| 7,033,754 B2 | 4/2006 | Chee et al. |
| 7,037,687 B2 | 5/2006 | Williams et al. |
| 7,045,097 B2 | 5/2006 | Kovacs |
| 7,049,645 B2 | 5/2006 | Sawada et al. |
| 7,060,431 B2 | 6/2006 | Chee et al. |
| 7,067,886 B2 | 6/2006 | Bonges et al. |
| 7,084,641 B2 | 8/2006 | Brederlow |
| 7,085,502 B2 | 8/2006 | Shushakob et al. |
| 7,087,387 B2 | 8/2006 | Gerdes et al. |
| 7,090,975 B2 | 8/2006 | Shultz et al. |
| 7,091,059 B2 | 8/2006 | Rhodes |
| 7,092,757 B2 | 8/2006 | Larson et al. |
| 7,097,973 B1 | 8/2006 | Zenhausern |
| 7,105,300 B2 | 9/2006 | Parce et al. |
| 7,129,554 B2 | 10/2006 | Lieber et al. |
| 7,169,560 B2 | 1/2007 | Lapidus et al. |
| 7,190,026 B2 | 3/2007 | Lotfi et al. |
| 7,192,745 B2 | 3/2007 | Jaeger |
| 7,193,453 B2 | 3/2007 | Wei et al. |
| 7,211,390 B2 | 5/2007 | Rothberg et al. |
| 7,220,550 B2 | 5/2007 | Keen |
| 7,223,540 B2 | 5/2007 | Pourmand et al. |
| 7,226,734 B2 | 6/2007 | Chee et al. |
| 7,229,799 B2 | 6/2007 | Williams et al. |
| 7,235,389 B2 | 6/2007 | Lim et al. |
| 7,238,323 B2 | 7/2007 | Knapp et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,264,934 B2 | 9/2007 | Fuller |
| 7,265,929 B2 | 9/2007 | Umeda et al. |
| 7,267,751 B2 | 9/2007 | Gelbart et al. |
| 7,276,749 B2 | 10/2007 | Martin et al. |
| 7,279,588 B2 | 10/2007 | Hong et al. |
| 7,282,370 B2 | 10/2007 | Bridgham et al. |
| 7,285,384 B2 | 10/2007 | Fan et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,323,305 B2 | 1/2008 | Leamon et al. |
| 7,335,526 B2 | 2/2008 | Peters et al. |
| 7,335,762 B2 | 2/2008 | Rothberg et al. |
| 7,359,058 B2 | 4/2008 | Kranz et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,425,431 B2 | 9/2008 | Church et al. |
| 7,455,971 B2 | 11/2008 | Chee et al. |
| 7,462,452 B2 | 12/2008 | Williams et al. |
| 7,462,512 B2 | 12/2008 | Levon et al. |
| 7,462,709 B2 | 12/2008 | Jaeger |
| 7,465,512 B2 | 12/2008 | Wright et al. |
| 7,466,258 B1 | 12/2008 | Akopyan et al. |
| 7,470,352 B2 | 12/2008 | Eversmann et al. |

(56) References Cited

U.S. PATENT DOCUMENTS

| | | |
|---|---|---|
| 7,476,504 B2 | 1/2009 | Turner |
| 7,482,153 B2 | 1/2009 | Okada et al. |
| 7,482,677 B2 | 1/2009 | Lee et al. |
| 7,515,124 B2 | 4/2009 | Yaguma et al. |
| 7,534,097 B2 | 5/2009 | Wong et al. |
| 7,538,827 B2 | 5/2009 | Chou |
| 7,575,865 B2 | 8/2009 | Leamon et al. |
| 7,576,037 B2 | 8/2009 | Engelhardt et al. |
| 7,595,883 B1 | 9/2009 | El Gamal et al. |
| 7,605,650 B2 | 10/2009 | Forbes |
| 7,608,810 B2 | 10/2009 | Yamada |
| 7,609,093 B2 | 10/2009 | Sarig et al. |
| 7,609,303 B1 | 10/2009 | Lee |
| 7,612,369 B2 | 11/2009 | Stasiak |
| 7,612,817 B2 | 11/2009 | Tay |
| 7,614,135 B2 | 11/2009 | Santini et al. |
| 7,622,294 B2 | 11/2009 | Walt et al. |
| 7,645,596 B2 | 1/2010 | Williams et al. |
| 7,649,358 B2 | 1/2010 | Toumazou et al. |
| 7,667,501 B2 | 2/2010 | Surendranath et al. |
| 7,686,929 B2 | 3/2010 | Toumazou et al. |
| 7,695,907 B2 | 4/2010 | Miyahara et al. |
| 7,733,401 B2 | 6/2010 | Takeda |
| 7,772,383 B2 | 8/2010 | Chakrabarti et al. |
| 7,785,785 B2 | 8/2010 | Pourmand et al. |
| 7,785,790 B1 | 8/2010 | Church et al. |
| 7,794,584 B2 | 9/2010 | Chodavarapu et al. |
| 7,821,806 B2 | 10/2010 | Horiuchi |
| 7,838,226 B2 | 11/2010 | Kamahori et al. |
| 7,842,377 B2 | 11/2010 | Lanphere et al. |
| 7,842,457 B2 | 11/2010 | Berka et al. |
| 7,859,029 B2 | 12/2010 | Lee et al. |
| 7,859,291 B2 | 12/2010 | Kim |
| 7,875,440 B2 | 1/2011 | Williams et al. |
| 7,884,398 B2 | 2/2011 | Levon et al. |
| 7,885,490 B2 | 2/2011 | Heideman et al. |
| 7,888,013 B2 | 2/2011 | Miyahara et al. |
| 7,888,015 B2 | 2/2011 | Toumazou et al. |
| 7,888,708 B2 | 2/2011 | Yazawa et al. |
| 7,890,891 B2 | 2/2011 | Stuber et al. |
| 7,898,277 B2 | 3/2011 | Weir |
| 7,923,240 B2 | 4/2011 | Su |
| 7,927,797 B2 | 4/2011 | Nobile et al. |
| 7,932,034 B2 | 4/2011 | Esfandyarpour et al. |
| 7,948,015 B2 | 5/2011 | Rothberg et al. |
| 7,972,828 B2 | 7/2011 | Ward et al. |
| 7,981,362 B2 | 7/2011 | Glezer et al. |
| 8,012,690 B2 | 9/2011 | Berka et al. |
| 8,017,938 B2 | 9/2011 | Gomez et al. |
| 8,035,175 B2 | 10/2011 | Shim et al. |
| 8,052,863 B2 | 11/2011 | Suzuki et al. |
| 8,067,731 B2 | 11/2011 | Matyjaszczyk et al. |
| 8,114,591 B2 | 2/2012 | Toumazou et al. |
| 8,124,936 B1 | 2/2012 | Lagna |
| 8,133,698 B2 | 3/2012 | Silver |
| 8,138,496 B2 | 3/2012 | Li et al. |
| 8,199,859 B2 | 6/2012 | Zerbe et al. |
| 8,217,433 B1 | 7/2012 | Fife |
| 8,231,831 B2 | 7/2012 | Hartzell et al. |
| 8,232,582 B2 | 7/2012 | Sauer et al. |
| 8,232,813 B2 | 7/2012 | Burdett et al. |
| 8,247,849 B2 * | 8/2012 | Fife et al. ............... 257/253 |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg et al. |
| 8,277,628 B2 | 10/2012 | Ronaghi et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,349,167 B2 | 1/2013 | Rothberg et al. |
| 8,361,713 B2 | 1/2013 | Bridgham et al. |
| 8,383,896 B2 | 2/2013 | Floyd |
| 8,426,898 B2 | 4/2013 | Rothberg et al. |
| 8,445,194 B2 | 5/2013 | Drmanac et al. |
| 8,449,824 B2 | 5/2013 | Sun |
| 2002/0012933 A1 | 1/2002 | Rothberg et al. |
| 2002/0042388 A1 | 4/2002 | Cooper et al. |
| 2002/0150909 A1 | 10/2002 | Stuelpnagel et al. |
| 2002/0168678 A1 | 11/2002 | Williams et al. |
| 2003/0054396 A1 | 3/2003 | Weiner |
| 2003/0068629 A1 | 4/2003 | Rothberg et al. |
| 2003/0108867 A1 | 6/2003 | Chee et al. |
| 2003/0124599 A1 | 7/2003 | Chen et al. |
| 2003/0141928 A1 | 7/2003 | Lee |
| 2003/0141929 A1 | 7/2003 | Casper et al. |
| 2003/0186262 A1 | 10/2003 | Cailloux |
| 2003/0211502 A1 | 11/2003 | Sauer et al. |
| 2003/0215857 A1 | 11/2003 | Kilger et al. |
| 2003/0224419 A1 | 12/2003 | Corcoran et al. |
| 2003/0231531 A1 | 12/2003 | Baxter et al. |
| 2004/0023253 A1 | 2/2004 | Kunwar et al. |
| 2004/0079636 A1 | 4/2004 | Hsia et al. |
| 2004/0136866 A1 | 7/2004 | Pontis et al. |
| 2004/0185484 A1 | 9/2004 | Costa et al. |
| 2004/0197803 A1 | 10/2004 | Yaku et al. |
| 2005/0006234 A1 | 1/2005 | Hassibi |
| 2005/0009022 A1 | 1/2005 | Weiner et al. |
| 2005/0031490 A1 | 2/2005 | Gumbrecht et al. |
| 2005/0032075 A1 | 2/2005 | Yaku et al. |
| 2005/0058990 A1 | 3/2005 | Guia et al. |
| 2005/0106587 A1 | 5/2005 | Klapproth et al. |
| 2005/0156207 A1 | 7/2005 | Yazawa et al. |
| 2005/0181440 A1 | 8/2005 | Chee et al. |
| 2005/0191698 A1 | 9/2005 | Chee et al. |
| 2005/0212016 A1 | 9/2005 | Brunner et al. |
| 2005/0221473 A1 | 10/2005 | Dubin et al. |
| 2005/0230245 A1 | 10/2005 | Morgenshtein et al. |
| 2005/0233318 A1 | 10/2005 | Chee et al. |
| 2005/0239132 A1 | 10/2005 | Klapproth |
| 2005/0282224 A1 | 12/2005 | Fouillet et al. |
| 2006/0024711 A1 | 2/2006 | Lapidus et al. |
| 2006/0057604 A1 | 3/2006 | Chen et al. |
| 2006/0073513 A1 | 4/2006 | Chee et al. |
| 2006/0141474 A1 | 6/2006 | Miyahara et al. |
| 2006/0166203 A1 | 7/2006 | Tooke et al. |
| 2006/0197118 A1 | 9/2006 | Migliorato et al. |
| 2006/0199193 A1 | 9/2006 | Koo et al. |
| 2006/0205061 A1 | 9/2006 | Roukes |
| 2006/0219558 A1 | 10/2006 | Hafeman et al. |
| 2006/0228721 A1 | 10/2006 | Leamon et al. |
| 2006/0246497 A1 | 11/2006 | Huang et al. |
| 2006/0269927 A1 | 11/2006 | Lieber |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0212681 A1 | 9/2007 | Shapiro et al. |
| 2007/0231824 A1 | 10/2007 | Chee et al. |
| 2007/0233477 A1 | 10/2007 | Halowani et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0014589 A1 | 1/2008 | Link et al. |
| 2008/0096216 A1 | 4/2008 | Quake et al. |
| 2008/0121946 A1 | 5/2008 | Youn et al. |
| 2008/0230386 A1 | 9/2008 | Srinivasan et al. |
| 2009/0048124 A1 | 2/2009 | Leamon et al. |
| 2009/0062132 A1 | 3/2009 | Bortner |
| 2009/0079414 A1 | 3/2009 | Levon et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2010/0007326 A1 | 1/2010 | Nakazato |
| 2010/0137143 A1 | 6/2010 | Rothberg et al. |
| 2010/0244106 A1 | 9/2010 | Parker et al. |
| 2010/0301398 A1 * | 12/2010 | Rothberg et al. ............ 257/253 |
| 2011/0037121 A1 | 2/2011 | Lee et al. |
| 2011/0062972 A1 | 3/2011 | Je et al. |
| 2011/0165557 A1 | 7/2011 | Ah et al. |
| 2011/0181253 A1 | 7/2011 | Isham et al. |
| 2011/0217697 A1 | 9/2011 | Rothberg et al. |
| 2011/0230375 A1 | 9/2011 | Rothberg et al. |

(56) References Cited

U.S. PATENT DOCUMENTS

| | | |
|---|---|---|
| 2011/0236263 A1 | 9/2011 | Sawada et al. |
| 2011/0247933 A1 | 10/2011 | Rothberg et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2012/0000274 A1 | 1/2012 | Fife |
| 2012/0001056 A1 | 1/2012 | Fife et al. |
| 2012/0001235 A1 | 1/2012 | Fife |
| 2012/0001236 A1 | 1/2012 | Fife et al. |
| 2012/0001237 A1 | 1/2012 | Fife et al. |
| 2012/0001646 A1 | 1/2012 | Bolander et al. |
| 2012/0001779 A1 | 1/2012 | Fife et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |
| 2012/0037961 A1 | 2/2012 | Rothberg et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife et al. |
| 2012/0074956 A1 | 3/2012 | Fife et al. |
| 2012/0129703 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0173159 A1 | 7/2012 | Davey et al. |
| 2012/0247977 A1 | 10/2012 | Rothberg et al. |
| 2012/0261274 A1 | 10/2012 | Rearick et al. |
| 2012/0265474 A1 | 10/2012 | Rearick et al. |
| 2012/0279859 A1 | 11/2012 | Rothberg et al. |
| 2012/0280285 A1 | 11/2012 | Rothberg et al. |
| 2012/0280286 A1 | 11/2012 | Rothberg et al. |
| 2012/0283146 A1 | 11/2012 | Rothberg et al. |
| 2012/0286332 A1 | 11/2012 | Rothberg et al. |
| 2012/0286333 A1 | 11/2012 | Rothberg et al. |
| 2012/0286771 A1 | 11/2012 | Rothberg et al. |
| 2012/0288853 A1 | 11/2012 | Rothberg et al. |
| 2012/0288976 A1 | 11/2012 | Rothberg et al. |
| 2012/0289413 A1 | 11/2012 | Rothberg et al. |
| 2012/0293158 A1 | 11/2012 | Rothberg et al. |
| 2012/0295795 A1 | 11/2012 | Rothberg et al. |
| 2012/0322054 A1 | 12/2012 | Rothberg et al. |
| 2012/0325683 A1 | 12/2012 | Milgrew |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329044 A1 | 12/2012 | Milgrew |
| 2012/0329192 A1 | 12/2012 | Bustillo et al. |
| 2013/0001653 A1 | 1/2013 | Milgrew |
| 2013/0004948 A1 | 1/2013 | Milgrew |
| 2013/0004949 A1 | 1/2013 | Rearick et al. |
| 2013/0009214 A1 | 1/2013 | Bustillo et al. |
| 2013/0015505 A1 | 1/2013 | Rothberg et al. |
| 2013/0015506 A1 | 1/2013 | Rothberg et al. |
| 2013/0017959 A1 | 1/2013 | Rothberg et al. |

FOREIGN PATENT DOCUMENTS

| | | |
|---|---|---|
| DE | 102008012899 | 9/2009 |
| EP | 1975246 | 3/1984 |
| EP | 0223618 | 5/1987 |
| EP | 1371974 | 12/2003 |
| EP | 1432818 | 6/2004 |
| EP | 1542009 | 6/2005 |
| EP | 1557884 | 7/2005 |
| EP | 1870703 | 12/2007 |
| EP | 2307577 | 4/2011 |
| GB | 2457851 | 9/2009 |
| GB | 2461127 B | 7/2010 |
| JP | 2000055874 | 2/2000 |
| JP | 2002272463 | 9/2002 |
| JP | 2005218310 | 8/2004 |
| JP | 2005518541 | 6/2005 |
| JP | 2011525810 | 9/2011 |
| KR | 100442838 | 7/2004 |
| KR | 100455283 | 10/2004 |
| WO | WO-89/09283 | 10/1989 |
| WO | WO-98/13523 | 4/1998 |
| WO | WO-98/46797 | 10/1998 |
| WO | WO-01/20039 | 3/2001 |
| WO | WO-01/81896 | 11/2001 |
| WO | WO-02/077287 | 10/2002 |
| WO | WO-02/086162 | 10/2002 |
| WO | WO-03/073088 | 9/2003 |
| WO | WO-2004/040291 | 5/2004 |
| WO | WO-2005/047878 | 5/2005 |
| WO | WO2005043160 | 5/2005 |
| WO | WO-2005/054431 | 6/2005 |
| WO | WO2005602049 | 7/2005 |
| WO | WO-2005/084367 | 9/2005 |
| WO | WO-2006/005967 | 1/2006 |
| WO | WO-2006/022370 | 3/2006 |
| WO | WO2007002204 | 1/2007 |
| WO | WO-2007/086935 | 8/2007 |
| WO | WO-2008/007716 | 1/2008 |
| WO | WO-2008/058282 | 5/2008 |
| WO | WO-2008/076406 | 6/2008 |
| WO | WO-2008/107014 | 9/2008 |
| WO | WO-2009/012112 | 1/2009 |
| WO | WO2009074926 | 6/2009 |
| WO | WO2009008190 | 7/2009 |
| WO | WO-2009/158006 | 12/2009 |
| WO | WO-2010/008480 | 1/2010 |
| WO | WO-2010/047804 | 4/2010 |
| WO | WO-2010/138182 | 12/2010 |
| WO | WO-2012/003359 | 1/2012 |
| WO | WO-2012/003363 | 1/2012 |
| WO | WO-2012/003368 | 1/2012 |
| WO | WO-2012/003380 | 1/2012 |
| WO | WO-2012/006222 | 1/2012 |

OTHER PUBLICATIONS

Akiyama, T. et al., "Ion-Sensitive Field-Effect Transistors with Inorganic Gate Oxide for pH Sensing", IEE Transactions on Electron Devices, vol. ED-29 (12), 1982, pp. 1936-1941.

AU2011226767 Search Information Statement Mailed Oct. 26, 2011.

Bandiera, L. et al., "A fully electronic sensor for the measurement of cDNA hybridization kinetics", Biosens Bioelectron, vol. 22, 2007, pp. 2108-2114.

Barbaro, M. et al., "A CMOS, Fully Integrated Sensor for Electronic Detection of DNA Hybridization", IEEE Electron Device Letters, vol. 27(7), 2006, pp. 595-597.

Barbaro, M. et al., "A Charge-Modulated FET for Detection of Biomolecular Processes: Conception, Modeling, and Simulation", IEEE Transactions on Electron Devices, vol. 53(1), 2006, pp. 158-166.

Barbaro, M. et al., "Fully electronic DNA hybridization detection by a standard CMOS biochip", Sensors and Actuators B Chemical, vol. 118, 2006, pp. 41-46.

Bashford, G. et al., "Automated bead-trapping apparatus and control system for single-molecule DNA sequencing", Optics Express, vol. 16(5), 2008, pp. 3445-3455.

Baumann, W. et al., "Microelectronic sensor system for microphysiological application on living cells", Sensors and Actuators B, vol. 55(1), 1999, pp. 77-89.

Bausells, J. et al., "Ion-sensitive field-effect transistors fabricated in a commercial CMOS technology", Sensors and Actuators B Chemical, vol. 57(1-3), 1999, pp. 56-62.

Bergveld, P., "ISFET, Theory and Practice", IEEE Sensor Conference, Toronto, Oct. 2003, 2003, pp. 1-26.

Bergveld, P., "Thirty years of ISFETOLOGY What happened in the past 30 years and what may happen in the next 30 years", Sensors and Actuators B, vol. 88(1), 2003, pp. 1-20.

Besselink, G. et al., ISFET Affinity Sensor, Methods in Biotechnology, vol. 7: Affinity Biosensors: Techniques and Protocols, 1998, pp. 173-185.

(56) References Cited

OTHER PUBLICATIONS

Bobrov, P. et al., "Chemical sensitivity of an ISFET with $Ta_2O_5$ membrane in strong acid and alkaline solutions", Sensors and Actuators B, vol. 3, 1991, pp. 75-81.
Bousse, L. et al., "A process for the combined fabrication of ion sensors and CMOS circuits", IEEE Electron Device Letters, vol. 9(1), 1988, pp. 44-46.
Bousse, L. et al., "Zeta potential measurements of $Ta_2O_5$ and $SiO_2$ thin films", J. Colloid Interface Sci., vol. 147(1), 1991, pp. 22-32.
Chen, Y. et al., "Nanoscale field effect transistor for biomolecular signal amplification", App Phys Letter, vol. 91(24), 2007, pp. 243511-1-243511-3.
Chen, Y. et al., "Silicon-based nanoelectronic field-effect pH sensor with local gate control", App Phys Letter, vol. 89, 2006, pp. 223512-1-223512-3.
Chou, J. et al., Letter to the Editor on "Simulation of Ta2O5 gate ISFET temperature characteristics", Sensors and Actuators B, vol. 80, 2001, pp. 290-291.
Chou, J. et al., "Simulation of Ta2O5 gate ISFET temperature characteristics", Sensor and Actuators B, vol. 71, Letter to the Editor, 2000, pp. 73-76.
Chung, W-Y. et al., "ISFET interface circuit embedded with noise rejection capability", Electronics Letters, vol. 40(18), e-pub, 2004, 1115-1116.
Chung, W-Y. et al., "ISFET performance enhancement by using the improved circuit techniques", Sensors and Actuators B, vol. 113, 2006, pp. 555-562.
Eijkel, J. et al., "Measuring Donnan-related phenomena using a solid-state ion sensor and a concentration-step method", J. Membrane Sci., vol. 127, 1997, pp. 203-221.
Eijkel, J., "Potentiometric detection and characterization of adsorbed protein using stimulus-response measurement techniques", Thesis, Sep. 3, 1955, pp. 1-147; 160-192.
Eltoukhy, H. et al., "A 0.18um CMOS 10-6 lux Bioluminescence Detection System-on-Chip", ISSCC 2004/Session12/Biomicrosystems/12.3, 2004, pp. 1-3.
Eltoukhy, H. et al., "A. 0.18-um CMOS Bioluminescence Detection Lab-on-Chip", IEEE J Solid-State Circuits, vol. 41(3), 2006, pp. 651-662.
Esfandyarpour, H. et al., "Gate-controlled microfluidic chamber with magnetic bead for DNA sequencing-by-synthesis technology", Proc 5th Intl Conf Nanochannels, Microchannels and Minichannels, Puebla, Mexico, Jun. 18-20, 2007, pp. 1-5.
Eversmann, B. et al., "A 128 x 128 CMOS Biosensor Array for Extracellular Recording of Neural Activity", IEEE J. Solid-State Circ., vol. 38(12), 2003, pp. 2306-2317.
Faramarzpour, N. et al., "CMOS-Based Active Pixel for Low-Light Level Detection: Analysis and Measurements", IEEE Trans Electron Devices, vol. 54(12), 2007, pp. 3229-3237.
Finn, A. et al., "Towards an Optimization of FET-Based Bio-Sensors", European Cells and Materials, vol. 4, Sup 2, 2002, pp. 21-23.
Fraden, J., "Handbook of Modern Sensors-Physics, Designs, and Applications", 17.3.2 CHEMFET Sensors, 1996, pp. 499-501.
Fritz, J. et al., "Electronic detection of DNA by its intrinsic molecular charge", PNAS, vol. 99(22), 2002, pp. 14142-14146.
GB0811656.8 Search and Examination Report Mailed Mar. 12, 2010.
GB0811656.8 Search Report Mailed Sep. 21, 2009.
GB0811657.6 Examination Report Mailed Jun. 30, 2010.
GB0811657.6 Search Report under Section 17 Mailed Oct. 26, 2009.
Gracia, I. et al., "Test Structures for ISFET Chemical Sensors", Proc IEEE 1992 Intl Conf Microelec Test Struct, 1992, pp. 156-159.
Hammond, P. et al., "A System-on-Chip Digital pH Meter for Use in a Wireless Diagnostic Capsule", IEEE Trans Biomedical Eng., vol. 52(4), 2005, pp. 687-694.
Hammond, P. et al., "Design of a Single-Chip pH Sensor Using a Conventional 0.6-μm CMOS Process", IEEE Sensors Journal, vol. 4(6), 2004, pp. 706-712.
Hammond, P. et al., "Encapsulation of a liquid-sensing microchip using SU-8 photoresist", MicoElectronic Engineering, vol. 73-74, 2004, pp. 893-897.
Hammond, S. et al., "Genomic sequencing and analysis of a Chinese Hamster ovary cell line using Illumina sequencing technology", BMC Genomics, vol. 12:67, 2011, pp. 1-8.
Han, Y., "Label-free detection of biomolecules by a field-effect transistor microarray biosensor with bio-functionalized gate surfaces", Aachen, Techn. Hochsch., Diss., 2006, pp. 1-63.
Hara, H. et al., "Dynamic response of a $Ta_2O_5$-gate pH-sensitive field-effect transistor", Sensors Actuators B, vol. 32, 1996, pp. 115-119.
Hermon, Z. et al., "Miniaturized bio-electronic hybrid for chemical sensing applications", Tech Connect News, 2008, p. 1.
Hideshima, S. et al., "Detection of tumor marker in blood serum using antibody-modified field effect transistor with optimized BSA blocking", Sensors and Actuations B: Chemical, vol. 161, 2012, pp. 146-150.
Hizawa, T. et al., "Fabrication of a two-dimensional pH image sensor using a charge transfer technique", Sensors and Actuators B Chemical, vol. 117, 2006, pp. 509-515.
Hizawa, T. et al., "32 x 32 pH Image Sensors for Real Time Observation of Biochemical Phenomena", Solid-State Sensors, Actuators and Microsystems Conference, 2007, Transducers 2007. International, 2007, pp. 1311-1312.
Jakobson, C. et al., "Low frequency noise and drift in Ion Sensitive Field Effect Transistors", Sensors Actuators B, vol. 68, 2000, pp. 134-139.
Ji, H. et al., "A CMOS contact imager for locating individual cells", ISCAS, 2006, pp. 3357-3360.
Ji, H. et al., "Contact Imaging: Simulation and Experiment", IEEE Trans Circuits Systems-I: Regular Papers, vol. 54(8), 2007, pp. 1698-1710.
Kim, D. et al., "An FET-type charger sensor for highly sensitive detection of DNA sequence", Biosens Bioelectron, vol. 20(1), 2004, pp. 69-74.
Klein, M., "Time effects of ion-sensitive field-effect transistors", Sensors and Actuators B, vol. 17(1-2), 1989, pp. 203-208.
Koch, S. et al., "Protein detection with a novel ISFET-based zeta potential analyzer", Biosensors & Bioelectronics, vol. 14, 1999, pp. 413-421.
Kruise, J. et al., "Detection of protein concentrations using a pH-step titration method", Sensors Actuators B, vol. 44, 1997, pp. 297-303.
Leamon, J. et al., "A Massively Parallel PicoTiterPlate Based Platform for Discrete Picoliter-Scale Polymerase Chain Reactions", Electrophoresis, vol. 24, 2003, pp. 3769-3777.
Leamon, J. et al., "Cramming More Sequencing Reactions onto Microreactor Chips", Chemical Reviews, vol. 107, 2007, pp. 3367-3376.
Lee, C-S. et al., "Ion-sensitive Field-Effect Transistor for Biological Sensing", Sensors, vol. 9, 2009, pp. 7111-7131.
Lohrengel, M. et al., "A new microcell or microreactor for material surface investigations at large current densities", Electrochimica Acta, vol. 49, 2004, pp. 2863-2870.
Lui, A. et al., "A Test Chip for ISFET/CMNOS Technology Development", Proc. of the 1996 IEEE Intl. Conf. on Microelectronic Test Structures, vol. 9, 1996, pp. 123-128.
Margulies, M. et al., "Genome sequencing in microfabricated high-density picolitre reactors", Nature, vol. 437(7057), 2005, pp. 376-380.
Marshall, A. et al., "DNA chips: an array of possibilities", Nature Biotechnology, vol. 16, 1998, pp. 27-31.
Martinoia, S. et al., "A behavioral macromodel of the ISFET in SPICE", Sensors Actuators B, vol. 62, 2000, pp. 182-189.
Martinoia, S. et al., "Development of ISFET Array-Based Microsystems for Bioelectrochemical measurements of cell populations", Biosensors & Bioelectronics, vol. 16, 2001, pp. 1043-1050.
Medoro, G. et al., "A Lab-on-a-Chip for Cell Detection and Manipulation", IEEE Sensors J, vol. 3(3), 2003, pp. 317-325.
Meyburg, S. et al., "N-Channel field-effect transistors with floating gates for extracellular recordings", Biosens Bioelectron, vol. 21(7), 2006, pp. 1037-1044.

(56) References Cited

OTHER PUBLICATIONS

Milgrew, M. et al., "A 16x16 CMOS proton camera array for direct extracellular imaging of hydrogen-ion activity", IEEE Intl Solid-State Circuits Conf, Session 32:24, 2008, pp. 590-638.
Milgrew, M. et al., "A large transistor based sensor array chip for direct extracellular imaging", Sensors and Actuators B Chemical, vol. 111-112, 2005, pp. 347-353.
Milgrew, M. et al., "Matching the transconductance characteristics of CMOS ESFET arrays by removing trapped charge", IEEE Trans Electron Devices, vol. 55(4), 2008, pp. 1074-1079.
Milgrew, M. et al., "Microsensor Array Technology for Direct Extracellular Imaging", Dept Electronic and EE, University of Glasgow, 2006, pp. 1-23.
Milgrew, M. et al., "The development of scalable sensor arrays using standard CMOS technology", Sensors and Actuators B, vol. 103, 2004, pp. 37-42.
Milgrew, M. et al., "The fabrication of scalable multi-sensor arrays using standard CMOS technology", 2003 IEEE Custom Integrated Circuits Conference, 2003, pp. 513-516.
Miyahara, Y. et al., "Biochip Using Micromachining Technology", J. Institute of Electrostatics, Japan, vol. 27(6), (Translation Included), 2003, pp. 268-272.
Miyahara, Y. et al., "Direct Transduction of Primer Extension into Electrical Signal Using Genetic Field Effect Transistor", Micro Total Analysis Systems 2004, vol. 1, 2004, pp. 303-305.
Miyahara, Y. et al., "Potentiometric Detection of DNA Molecules Using Field Effect Transistor", The Japan Society of Applied Physics, No. 3 (Translation included), 2003, pp. 1180.
Nyren, P. et al., "Enzymatic Method for Continuous Monitoring of Inorganic Pyrophosphate Synthesis", Analytical Biochemistry, vol. 151, 1985, pp. 504-509.
Oelbner, W. et al., "Encapsulation of ESFET sensor chips", Sensors Actuators B, vol. 105, 2005, pp. 104-117.
Oelbner, W. et al., "Investigation of the dynamic response behaviour of ISFET pH sensors by means of laser Doppler velocimetry (LDV)", Sensors Actuators B, vol. 26-27, 1995, pp. 345-348.
Offenhausser, A. et al., "Field-Effect transistor array for monitoring electrical activity from mammalian neurons in culture", Biosensors & Bioelectronics, vol. 12(8), 1997, pp. 819-826.
Ohno, Y. et al., "Electrolyte-Gated Graphene Field-Effect Transistors for Detecting pH and Protein Adsorption", Nano Letters, vol. 9(9), Jul. 28, 2009, pp. 3318-3322.
Patolsky, F. et al., "Nanowire-Based Biosensors", Analyt Chem 1, vol. 78(13), 2006, pp. 4261-4269.
PCT/US2009/05745 International Preliminary Report on Patentability Mailed Apr. 26, 2011.
PCT/US2009/05745 International Search Report Mailed Dec. 11, 2009.
PCT/US2009/05745 Written Opinion Mailed Dec. 11, 2009.
PCT/US2007/025721 International Preliminary Report on Patentability Mailed Jun. 16, 2009.
PCT/US2007/025721 Written Opinion Mailed Jun. 16, 2009.
PCT/US2009/003766 International Preliminary Report on Patentability Mailed Jan. 5, 2011.
PCT/US2009/003766 International Search Report Mailed Apr. 8, 2010.
PCT/US2009/003766 Written Opinion Mailed Apr. 8, 2010.
PCT/US2009/003797 International Search Report Mailed Mar. 12, 2010.
PCT/US2009/003797 Written Opinion Mailed Mar. 12, 2010.
PCT/US2010/001543 International Preliminary Report on Patentability Mailed Nov. 29, 2011.
PCT/US2010/001543 International Search Report and Written Opinion Mailed Oct. 13, 2010.
PCT/US2010/048835 International Preliminary Report on Patentability Mailed Mar. 19, 2013.
PCT/US2010/048835 International Search Report and Written Opinion Mailed Dec. 16, 2010.
PCT/US2011/042655 International Search Report Mailed Oct. 21, 2011.
PCT/US2011/042660 International Search Report Mailed Nov. 2, 2011.
PCT/US2011/042665 International Search Report Mailed Nov. 2, 2011.
PCT/US2011/042669 International Search Report Mailed Jan. 9, 2012.
PCT/US2011/042669 Written Opinion Mailed Jan. 9, 2012.
PCT/US2011/042683 International Search Report Mailed Feb. 16, 2012.
PCT/US2011/042683 Written Opinion Mailed Feb. 16, 2012.
Poghossian, A. et al., "Functional testing and characterization of ISFETs on wafer level by means of a micro-droplet cell", Sensors, vol. 6, 2006, pp. 397-404.
Pourmand, N. et al., "Direct electrical detection of DNA synthesis", PNAS, vol. 103(17), 2006, pp. 6466-6470.
Pouthas, F. et al., "Spatially resolved electronic detection of biopolymers", Phys Rev, vol. 70, 2004, pp. 031906-1-031906-8.
Premanode, B. et al., "A composite ISFED readout circuit employing current feedback", Sensors Actuators B, vol. 127, 2007, pp. 486-490.
Premanode, B. et al., "A novel, low power biosensor for real time monitoring of creatine and urea in peritoneal dialysis", Sensors Actuators B, vol. 120, 2007, pp. 732-735.
Premanode, B. et al., "Ultra-low power precision ISFET readout using global current feedback", Electronic Lett, vol. 42(22), 2006, pp. 1264-1265.
Purushothaman, S. et al., "Protons and single nucleotide polymorphism detection: A simple use for the Ion Sensitive Field Effect Transistor", Sensors and Actuators B Chemical, vol. 114(2), 2006, pp. 964-968.
Purushothaman, S. et al., "Towards Fast Solid State Dna Sequencing", IEEE ISCAS 2002 Proceedings, Circuits and Systems, vol. 4, 2002, pp. IV-169-IV-172.
Rodriguez-Villegas, E., "Solution to trapped charge in FGMOS transistors", Electronics Letters, vol. 39(19), 2003.
Sakata, T. et al., "Cell-based field effect devices for cell adhesion analysis", Intl. Conf. on Microtechnologies in Medicine and Biology, May 9-12, 2006, Okinawa, Japan, pp. 177-179.
Sakata, T. et al., "Detection of DNA recognition events using multi-well field effect transistor", Biosensors and Bioelectronics vol. 21, 2005, pp. 827-832.
Sakata, T. et al., "Detection sensitivity of genetic field effect transistor combined with charged nanoparticle-DNA conjugate", Proc. of 2006 Intl. Conf. on Microtechnologies in Medicine and Biology, May 9-12, 2006, Okinawa, Japan, pp. 97-100.
Sakata, T. et al., "Direct detection of single nucleotide polymorphism using genetic field effect transistor", Digest of Papers Microprocesses and Nanotechnology 2004, Osaka, Japan, 2004 International Microprocesses and Nanotechnology Conference, 2004, pp. 226-227.
Sakata, T. et al., "Direct Detection of Single-Base Extension Reaction Using Genetic Field Effect Transistor", Proc. of 3rd Ann. Intl. IEEE EMBS Special Topic Conf. on Microtechnologies in Medicine and Biology, Kahuku, Oahu, HI, May 12-15, 2005, pp. 219-222.
Sakata, T. et al., "Direct transduction of allele-specific primer extension into electrical signal using genetic field effect transistor", Biosensors and Bioelectronics, vol. 22, 2007, pp. 1311-1316.
Sakata, T. et al., "DNA Analysis Chip Based on Field-Effect Transistors", Japanese Journal of Applied Physics, vol. 44(4B), 2005, pp. 2854-2859.
Sakata, T. et al., "DNA Sequencing Based on Intrinsic Molecular Charges", Angewandte Chemie International Edition 2006, vol. 118, 2006, pp. 2283-2286.
Sakata, T. et al., "DNA Sequencing Based on Intrinsic Molecular Charges", Angewandte Chemie International Edition 2006, vol. 45, 2006, pp. 2225-2228.
Sakata, T. et al., "DNA Sequencing Using Genetic Field Effect Transistor", Solid-State Sensors, Actuators and Microsystems, vol. 2, 2005, pp. 1676-1679.
Sakata, T. et al., "Immobilization of oligonucleotide probes on Si3N4 surface and its application to genetic field effect transistor", Materials Science and Engineering: C, vol. 24, 2004, pp. 827-832.

(56) References Cited

OTHER PUBLICATIONS

Sakata, T. et al., "Potential Behavior of Biochemically Modified Gold Electrode for Extended-Gate Field-Effect Transistor", Japanese Journal of Applied Physics, vol. 44(4B), 2005, pp. 2860-2863.

Sakata, T. et al., "Potential Response of Genetic Field Effect Transistor to Charged Nanoparticle-DNA Conjugate", Digest of Papers Microprocesses and Nanotechnology 2005, Tokyo, Japan, 2005 Intl Microprocesses and Nanotech Conf., Hotel Bellclassic, 2005, pp. 42-43.

Sakata, T. et al., "Potentiometric Detection of Allele Specific Oligonucleotide Hybridization Using Genetic Field Effect Transistor", Micro Total Analysis Systems, 8th Intl. Conf. on Miniaturized Systems for Chemistry and Life Sciences, 2004, pp. 300-302.

Sakata, T. et al., "Potentiometric detection of DNA molecules hybridization using gene field effect transistor and intercalator" Materials Research Society Symposium Proceedings, vol. 782, 2004, pp. 393-400.

Sakata, T. et al., "Potentiometric Detection of DNA Using Genetic Transistor", Denki Gakkai Kenkyukai Shiryo Chemical Sensor Kenkyukai, CHS-03-51-55, 2003, pp. 1-5.

Sakata, T. et al., "Potentiometric Detection of Single Nucleotide Polymorphism by Using a Genetic Field-effect transistor", ChemBioChem, vol. 6, 2005, pp. 703-710.

Sakurai, T. et al., "Real-Time Monitoring of DNA Polymerase Reactions by a Micro ISFET pH Sensor", Anal Chem, vol. 64(17), 1992, pp. 1996-1997.

Salama, K., "CMOS luminescence detection lab-on-chip: modeling, design, and characterization", Thesis, Presented at Stanford University, 2005, pp. ii-78.

Salama, K., "Modeling and simulation of luminescence detection platforms", Biosensors & Bioelectronics, 2004, pp. 1377-1386.

Sawada, K. et al., "A novel fused sensor for photo- and ion-sensing", Sensors Actuators B, vol. 106, 2005, pp. 614-618.

Sawada, K. et al., "Highly sensitive ion sensors using charge transfer technique", Sensors Actuators B, vol. 98, 2004, pp. 69-72.

Schasfoort, R. et al., "A new approach to immunoFET operation", Biosensors & Bioelectronics, vol. 5, 1990, pp. 103-124.

Schasfoort, R. et al., "Field-effect flow control for microfabricated fluidic networks", Science, vol. 286(5441), 1999, pp. 942-945.

Schoning, M. et al., "Bio FEDs (Field-Effect Devices): State-of-the-Art and New Directions", Electroanalysis, vol. 18(19-20), 2006, pp. 1893-1900.

SG200903992-6 Search and Examination Report Mailed Jan. 20, 2011.

Shah, N., "Microfabrication of a parellel-array DNA pyrosequencing chip", NNIN REU Research Accomplishments, 2005, pp. 130-131.

Shepherd, L. et al., "A biochemical translinear principle with weak inversion ISFETs", IEEE Trans Circuits Syst-I, vol. 52(12), 2005, pp. 2614-2619.

Shepherd, L. et al., "A novel voltage-clamped CMOS ISFET sensor interface", IEEE, 2007, pp. 3331-3334.

Shepherd, L. et al., "Towards direct biochemical analysis with weak inversion ISFETS", Intl Workshop on Biomedical, 2004, S1.5-5-S1.5-8.

Shepherd, L. et al., "Weak inversion ISFETs for ultra-low power biochemical sensing and real-time analysis", Sensors Actuators B, vol. 107, 2005, pp. 468-473.

Shi, Y. et al., "Radical Capillary Array Electrophoresis Microplace and Scanner for High-Performance Nucleic Acid Analysis", Anal. Chem., vol. 71(23), 1999, pp. 5354-5361.

Simonian, A. L. et al., "FET based biosensors for the direct detection of organophosphate neurotoxins", Electroanalysis, vol. 16(22), 2004, pp. 1896-1906.

Souteyrand, E. et al., "Direct detection of the hybridization of synthetic homo-oligomer DNA sequences by field effect", J Phys Chem B, vol. 101(15), 1997, pp. 2980-2985.

Starodub, N. et al., "Immunosensor for the determination of the herbicide simazine based on an ion-selective field-effect transistor", Analytica Chimica Acta, vol. 424, 2000, pp. 37-43.

Takenaka, S. et al., "DNA Sensing on a DNA Probe-Modified Electrode Using Ferrocenylnaphthalene Dimide as the Electrochemically Active Ligand", Anal. Chem., vol. 72(6), 2000, pp. 1334-1341.

Tomaszewski, D. et al., "Electrical characterization of ISFETs", J Telecomm Info Technol, 2007, pp. 55-60.

Toumazou, C. et al., "Using transistors to linearase biochemistry", Elect Let, vol. 43(2), 2007, p. 3.

Truman, P. et al. "Monitoring liquid transport and chemical composition in lab on a chip systems using ion sensitive FET devices", Lab on a Chip, vol. 6, 2006, pp. 1220-1228.

Uslu, F. et al., "Labelfree fully electronic nucleic acid detection system based on a field-effect transistor device", Biosens & Bioelectron, vol. 19(12), 2004, pp. 1723-1731.

Van Der Wouden, E. et al., "Directional flow induced by synchronized longitudinal and zeta-potential controlling AC-electrical fields", Lab Chip, vol. 6(10), 2006, pp. 1300-1305.

Van Hal, R.E.G. et al., "A general model to describe the electrostatic potential at electrolyte oxide interfaces", Advances in Colloid and Interface Science, vol. 69, 1996, pp. 31-62.

Van Kerkhof, J. et al., "ISFET Responses on a stepwise change in electrolyte concentration at constant pH", Sensors Actuators B: Chemical, vol. 18-19, 1994, pp. 56-59.

Van Kerkhof, J. et al., "The ISFET based heparin sensor with a monolayer of protamine as affinity ligand", Biosensors & Bioelectronics, vol. 10(3), 1995, pp. 269-282.

Van Kerkhof, J., "Development of an ISFET based heparin sensor using the ion-step measuring method", Biosensors and Bioelectronics, 8 (9-10). pp. 463-472.

Wagner, T. et al., "'All-in-one solid-state device based on a light-addressable potentiometric sensor platform", Sensors and Actuators B, vol. 117, 2006, pp. 472-479.

Wang, W. et al., "Label-free detection of small-molecule-protein interactions by using nanowire nanosensors", Proc. of the Natl. Acad. of Sciences (PNAS), vol. 102(9), 2005, pp. 3208-3212.

Woias, P. et al., "Slow pH response effects of silicon nitride ISFET sensors", Sensors and Actuators B, vol. 48, 1998, pp. 501-504.

Woias, P., "Modeling the short time response of ISFET sensors", Sensors and Actuators B, vol. 24-25, 1995, pp. 211-217.

Wu, P. et al., "DNA and protein microarray printing on silicon nitride waveguide surfaces", Biosensors Bioelectron, vol. 21(7), 2006, pp. 1252-1263.

Xu, J. et al., "Analytical Aspects of FET-Based Biosensors", Frontiers in Bioscience, vol. 10, 2005, pp. 420-430.

Yeow, T.C.W. et al., "A very large integrated pH-ISFET sensor array chip compatible with standard CMOS processes", Sensor and Actuators B, vol. 44, 1997, pp. 434-440.

Yuqing, M. et al., "Ion sensitive field effect transducer-based biosensors", Biotechnology Advances, vol. 21, 2003, pp. 527-534.

Zhang, X. et al., "32-Channel Full Customized CMOS Biosensor Chip for Extracellular neural Signal Recording", Proc. of the 2nd Intl. IEEE EMBs Conf. on Neural Engineering, Arlington, Virginia, 2005, pp. v-viii.

Zhou, G. et al., "Quantitative detection of single nucleotide polymorphisms for a pooled sample by a bioluminometric assay coupled with modified primer extension reactions (BAMPER)", Nuc. Acids Res., vol. 29(19), e93, 2001, pp. 1-11.

Chan, Wai P. et al., "An Integrated ISFETs Instrumentation System in Standard CMOS Technology", IEEE Journal of Solid-State Circuits, vol. 45, No. 9, 2010, pp. 1923-1934.

Chinese Patent Application 200780051353.2 Second Office Action Mailed Mar. 5, 2013.

Chung, W-Y. et al., "New ISFET Interface Circuit Design with Temperature Compensation", Microelectronics Journal, vol. 37(10), 2006, pp. 1105-1114.

Chung, W-Y. et al., "Temperature Compensation Electronics for ISFET Readout Applications", Biomedical Circuits and Systems, IEEE International Workshop Singapore, 2004, pp. 305-308.

EP7867780.4 Examination Report Mailed Jul. 3, 2012.

Krause, M. et al., "Extended Gate Electrode Arrays for Extracellular Signal Recordings", Sensors and Actuators B, vol. 70, 2000, pp. 101-107.

(56) References Cited

OTHER PUBLICATIONS

Park, K-Y. et al., "ISFET Glucose Sensor System With Fast Recovery Characteristics by Employing Electrolysis", Sensors and Actuators B: Chemical, vol. 83 (1-3), 2002, pp. 90-97.

PCT/US2011/042668 International Preliminary Report on Patentability Mailed Mar. 26, 2013.

PCT/US2011/042668 International Search Report Mailed Oct. 28, 2011.

PCT/US2012/058996 International Search Report and Written Opinion Mailed Jan. 22, 2013.

PCT/US2012/071471 International Search Report and Written Opinion Mailed Apr. 24, 2013.

PCT/US2012/071482 International Search Report and Written Opinion Mailed May 23, 2013.

PCT/US2013/022140 International Search Report and Written Opinion Mailed May 2, 2013.

Pollack, J. et al., "Genome-Wide Analysis of DNA copy-number changes using cDNA Microarrays", Nature Genetics, vol. 23, 1999, pp. 41-46.

EP09798251.6 Extended European Search Report dated Aug. 27, 2013.

EP13161312.7 Extended European Search Report dated Oct. 15, 2013.

EP13163995.7 First Office Action dated Aug. 30, 2013.

EP13164768.7 Extended European Search Report dated Aug. 20, 2013.

EP13164768.7 First Office Action dated Aug. 30, 2013.

Hanshaw, R. et al., "An indicator displacement system for fluorescent detection of phosphate oxyanions under physiological conditions" Science Direct, Tetrahedron Ltrs., vol. 45, 2004, pp. 8721-8724.

JP20120246413 First Office Action dated Jun. 28, 2013.

Maki, W et al., "Nanowire-transistor based ultra-sensitive DNA methylation detection", Biosensors & Bioelectronics, vol. 23, 2008, pp. 780-787.

PCT/US2013/022129 International Search Report and Written Opinion dated Aug. 9, 2013.

Rothberg, J. et al., "An integrated semiconductor device enabling non-optical genome sequencing" Nature, vol. 475, No. 7356. 2011, pp. 348-352.

Dazhong, Z. et al. "Research of CMOS Biosensor IC for Extracellular Electrophysiological Signal Recording and pH value Measuring" Solid-State and Integrated Circuit Technology, 9th International Conference, Oct. 20, 2008, pp. 2557-2560.

EP11801437.2 Extended European Search Report dated Jul. 25, 2013.

EP11804218.3 Extended European Search Report dated Jul. 11, 2013.

EP11804218.3 First Office Action dated Jul. 29, 2013.

EP11827128.7 European Search Report dated Aug. 1, 2013.

EP13163995.7 Extended European Search Report dated Aug. 20, 2013.

Eriksson, J. et al. "Pyrosequencing Technology at Elevated Temperature" Electrophoresis, vol. 25, 2004, pp. 20-27.

Hizawa, et al. "Sensing Characteristics of Charge Transfer Type pH Sensor by Accumulative Operation" IEEE Sensors, EXCO, Daegu, Korea, 2006, pp. 144-147.

Lee, S. et al. "An Enhanced Glucose Biosensor Using Charge Transfer Techniques" Biosensors and Bioelectronics, vol. 24, 2008, pp. 650-656.

Matsuo, J. et al. "Charge Transfer Type pH Sensor with Super High Sensitivity" 14th International Conference on Solid-State Sensors Actuators and Microsystems, France, Jun. 10-14, 2007, pp. 1881-1884.

Milgrew, M. et al. "A Proton Camera Array Technology for Direct Extracellular Ion Imaging" IEEE International Symposium on Industrial Electronics, 2008, pp. 2051-2255.

Milgrew, M.J. et al., "The Development of Scalable Sensor Arrays Using Standard CMOS Technology" ScienceDirect, Sensors and Actuators, vol. 103, 2004, pp. 37-42.

PCT/US2011/042683 International Preliminary Report on Patentability Mailed Jun. 4, 2013.

Premanode, B. et al. "Drift Reduction in Ion-Sensitive FETs Using Correlated Double Sampling", Electronics Letters, IEEE Stevenage, GB, vol. 43 (16) Aug. 2, 2007.

Seong-Jin, K. et al. "Label-Free CMOS DNA Quantification With On-Chip Noise Reduction Schemes" Solid-State Sensors, Actuators and Microsystems Conference, IEEE, Jun. 10, 2013, pp. 947-950.

Voigt, H. et al. "Diamond-like carbon-gate pH-ISFET" Sensors and Actuators B., vol. 44, 1997, pp. 441-445.

\* cited by examiner

FIG. 10A  FIG. 10B

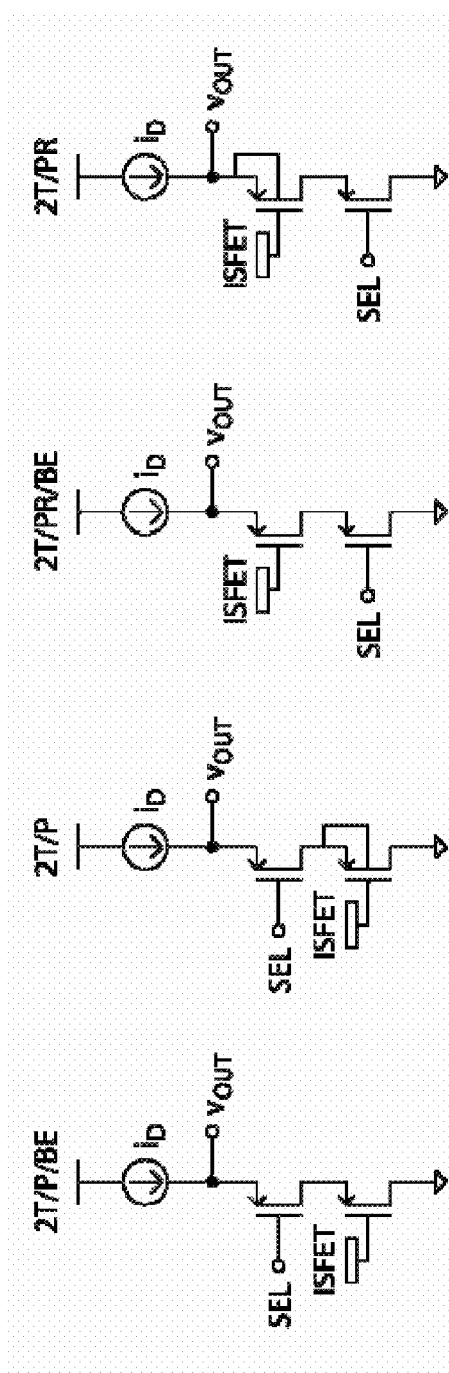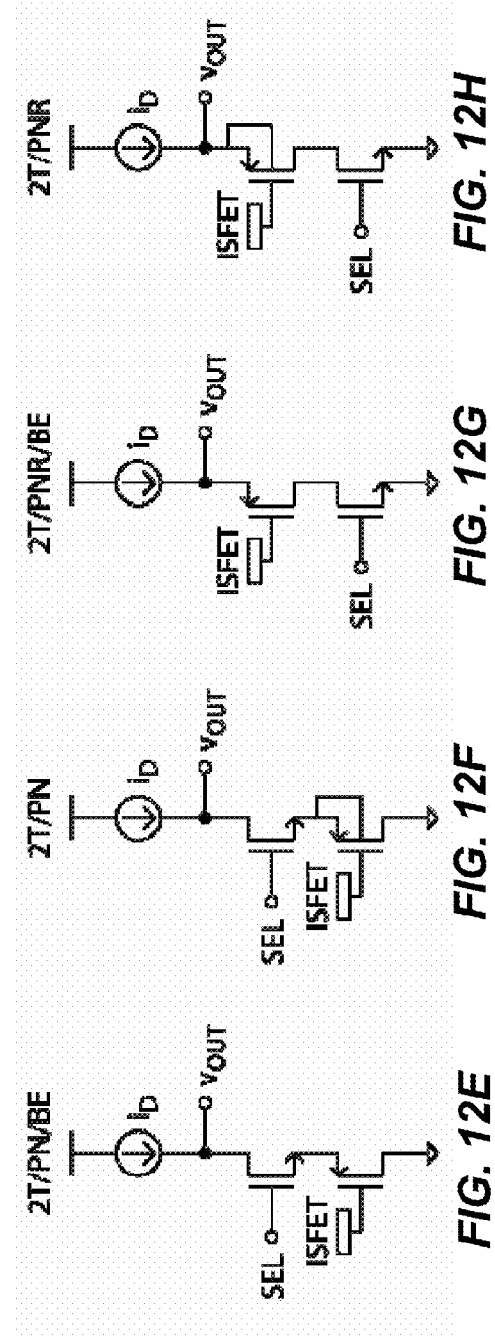

TWO-TRANSISTOR PIXEL ARRAY

RELATED APPLICATIONS

This application is a continuation of U.S. application Ser. No. 13/174,222 filed Jun. 30, 2011, which claims the benefit of priority to previously filed U.S. provisional patent application Ser. No. 61/360,493 filed Jun. 30, 2010, U.S. provisional application Ser. No. 61/360,495 filed Jul. 1, 2010, U.S. provisional application Ser. No. 61/361,403 filed Jul. 3, 2010, and U.S. provisional application Ser. No. 61/365,327 filed Jul. 17, 2010, the disclosures of all of which are incorporated herein by reference in their entireties.

BACKGROUND

Electronic devices and components have found numerous applications in chemistry and biology (more generally, "life sciences"), especially for detection and measurement of various chemical and biological reactions and identification, detection and measurement of various compounds. One such electronic device is referred to as an ion-sensitive field effect transistor, often denoted in the relevant literature as an "ISFET" (or pHFET). ISFETs conventionally have been explored, primarily in the academic and research community, to facilitate measurement of the hydrogen ion concentration of a solution (commonly denoted as "pH").

More specifically, an ISFET is an impedance transformation device that operates in a manner similar to that of a MOSFET (Metal Oxide Semiconductor Field Effect Transistor), and is particularly configured to selectively measure ion activity in a solution (e.g., hydrogen ions in the solution are the "analytes"). A detailed theory of operation of an ISFET is given in "Thirty years of ISFETOLOGY: what happened in the past 30 years and what may happen in the next 30 years," P. Bergveld, Sens. Actuators, 88 (2003), pp. 1-20 ("Bergveld"), which publication is hereby incorporated herein by reference in its entirety.

Details of fabricating an ISFET using a conventional CMOS (Complementary Metal Oxide Semiconductor) process may be found in Rothberg, et al., U.S. Patent Publication No. 2010/0301398, Rothberg, et al., U.S. Patent Publication No. 2010/0282617, and Rothberg et al, U.S. Patent Publication 2009/0026082; these patent publications are collectively referred to as "Rothberg", and are all incorporated herein by reference in their entirety. In addition to CMOS, however, biCMOS (i.e., bipolar and CMOS) processing may also be used, such as a process that would include a PMOS FET array with bipolar structures on the periphery. Alternatively, other technologies may be employed wherein a sensing element can be made with a three-terminal devices in which a sensed ion leads to the development of a signal that controls one of the three terminals; such technologies may also include, for example, GaAs and carbon nanotube technologies.

Taking a CMOS example, a P-type ISFET fabrication is based on a P-type silicon substrate, in which an N-type well forming a transistor "body" is formed. Highly doped P-type (P+) regions S and D, constituting a source and a drain of the ISFET, are formed within the N-type well. A highly doped N-type (N+) region B may also be formed within the N-type well to provide a conductive body (or "bulk") connection to the N-type well. An oxide layer may be disposed above the source, drain and body connection regions, through which openings are made to provide electrical connections (via electrical conductors) to these regions. A polysilicon gate may be formed above the oxide layer at a location above a region of the N-type well, between the source and the drain. Because it is disposed between the polysilicon gate and the transistor body (i.e., the N-type well), the oxide layer often is referred to as the "gate oxide."

Like a MOSFET, the operation of an ISFET is based on the modulation of charge concentration (and thus channel conductance) caused by a MOS (Metal-Oxide-Semiconductor) capacitance. This capacitance is constituted by a polysilicon gate, a gate oxide and a region of the well (e.g., N-type well) between the source and the drain. When a negative voltage is applied across the gate and source regions, a channel is created at the interface of the region and the gate oxide by depleting this area of electrons. For an N-well, the channel would be a P-channel (and vice-versa). In the case of an N-well, the P-channel would extend between the source and the drain, and electric current is conducted through the P-channel when the gate-source potential is negative enough to attract holes from the source into the channel. The gate-source potential at which the channel begins to conduct current is referred to as the transistor's threshold voltage VTH (the transistor conducts when VGS has an absolute value greater than the threshold voltage VTH). The source is so named because it is the source of the charge carriers (holes for a P-channel) that flow through the channel; similarly, the drain is where the charge carriers leave the channel.

As described in Rothberg, an ISFET may be fabricated with a floating gate structure, formed by coupling a polysilicon gate to multiple metal layers disposed within one or more additional oxide layers disposed above the gate oxide. The floating gate structure is so named because it is electrically isolated from other conductors associated with the ISFET; namely, it is sandwiched between the gate oxide and a passivation layer that is disposed over a metal layer (e.g., top metal layer) of the floating gage.

As further described in Rothberg, the ISFET passivation layer constitutes an ion-sensitive membrane that gives rise to the ion-sensitivity of the device. The presence of analytes such as ions in an analyte solution (i.e., a solution containing analytes (including ions) of interest or being tested for the presence of analytes of interest), in contact with the passivation layer, particularly in a sensitive area that may lie above the floating gate structure, alters the electrical characteristics of the ISFET so as to modulate a current flowing through the channel between the source and the drain of the ISFET. The passivation layer may comprise any one of a variety of different materials to facilitate sensitivity to particular ions; for example, passivation layers comprising silicon nitride or silicon oxynitride, as well as metal oxides such as silicon, aluminum or tantalum oxides, generally provide sensitivity to hydrogen ion concentration (pH) in an analyte solution, whereas passivation layers comprising polyvinyl chloride containing valinomycin provide sensitivity to potassium ion concentration in an analyte solution. Materials suitable for passivation layers and sensitive to other ions such as sodium, silver, iron, bromine, iodine, calcium, and nitrate, for example, are known, and passivation layers may comprise various materials (e.g., metal oxides, metal nitrides, metal oxynitrides). Regarding the chemical reactions at the analyte solution/passivation layer interface, the surface of a given material employed for the passivation layer of the ISFET may include chemical groups that may donate protons to or accept protons from the analyte solution, leaving at any given time negatively charged, positively charged, and neutral sites on the surface of the passivation layer at the interface with the analyte solution.

With respect to ion sensitivity, an electric potential difference, commonly referred to as a "surface potential," arises at the solid/liquid interface of the passivation layer and the analyte solution as a function of the ion concentration in the sensitive area due to a chemical reaction (e.g., usually involving the dissociation of oxide surface groups by the ions in the analyte solution in proximity to the sensitive area). This surface potential in turn affects the threshold voltage of the ISFET; thus, it is the threshold voltage of the ISFET that varies with changes in ion concentration in the analyte solution in proximity to the sensitive area. As described in Rothberg, since the threshold voltage VTH of the ISFET is sensitive to ion concentration, the source voltage VS provides a signal that is directly related to the ion concentration in the analyte solution in proximity to the sensitive area of the ISFET.

Arrays of chemically-sensitive FETs ("chemFETs"), or more specifically ISFETs, may be used for monitoring reactions—including, for example, nucleic acid (e.g., DNA) sequencing reactions, based on monitoring analytes present, generated or used during a reaction. More generally, arrays including large arrays of chemFETs may be employed to detect and measure static and/or dynamic amounts or concentrations of a variety of analytes (e.g., hydrogen ions, other ions, non-ionic molecules or compounds, etc.) in a variety of chemical and/or biological processes (e.g., biological or chemical reactions, cell or tissue cultures or monitoring, neural activity, nucleic acid sequencing, etc.) in which valuable information may be obtained based on such analyte measurements. Such chemFET arrays may be employed in methods that detect analytes and/or methods that monitor biological or chemical processes via changes in charge at the chemFET surface. Such use of ChemFET (or ISFET) arrays involves detection of analytes in solution and/or detection of change in charge bound to the chemFET surface (e.g. ISFET passivation layer).

Research concerning ISFET array fabrication is reported in the publications "A large transistor-based sensor array chip for direct extracellular imaging," M. J. Milgrew, M. O. Riehle, and D. R. S. Cumming, Sensors and Actuators, B: Chemical, 111-112, (2005), pp. 347-353, and "The development of scalable sensor arrays using standard CMOS technology," M. J. Milgrew, P. A. Hammond, and D. R. S. Cumming, Sensors and Actuators, B: Chemical, 103, (2004), pp. 37-42, which publications are incorporated herein by reference and collectively referred to hereafter as "Milgrew et al." Descriptions of fabricating and using ChemFET or ISFET arrays for chemical detection, including detection of ions in connection with DNA sequencing, are contained in Rothberg. More specifically, Rothberg describes using a chemFET array (in particular ISFETs) for sequencing a nucleic acid involving incorporating known nucleotides into a plurality of identical nucleic acids in a reaction chamber in contact with or capacitively coupled to chemFET, wherein the nucleic acids are bound to a single bead in the reaction chamber, and detecting a signal at the chemFET, wherein detection of the signal indicates release of one or more hydrogen ions resulting from incorporation of the known nucleotide triphosphate into the synthesized nucleic acid.

However, traditionally, ion concentration in the analyte solution is measured by measuring an instantaneous voltage at an output of the ISFET. The signal-to-noise ratio provided by the instantaneous voltage may not be as high as desired in a lot of situations. Further, with the scaling of ISFET sensor array designs, more ISFET sensors are packed on a chip. Thus, there is a need in the art to provide a better SNR than the instantaneous voltage measurement and also a need for on-chip data compression.

Moreover, with the scaling of ISFET sensor array designs, more and more ISFET sensors are packed on a chip. Thus, there is a need in the art to provide a readout scheme to output measured data from a chip at a high speed.

BRIEF DESCRIPTION OF THE DRAWING FIGURES

FIG. 12A to 12H illustrate 2T pixel configurations according to embodiments of the present invention.

FIG. 20A-P show surface potential diagrams for basic charge accumulation according to an embodiment of the present invention.

Figure 21:
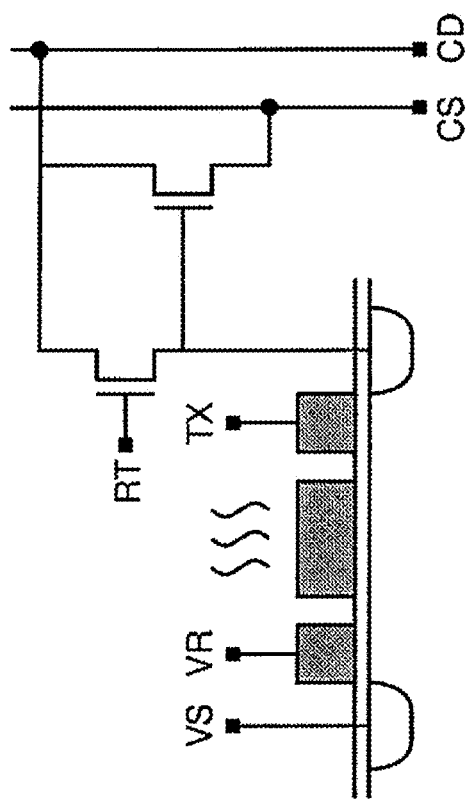
Figure 22:
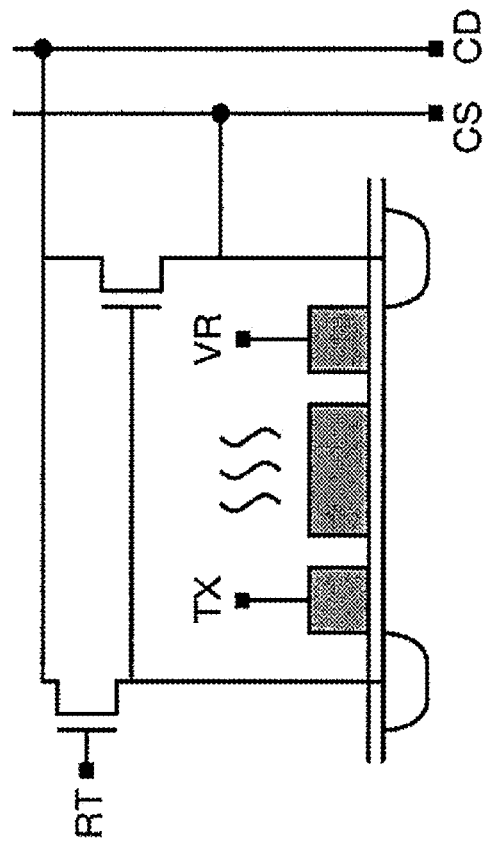

FIGS. 21 and 22 show an IS accumulation pixel with 2 transistors according to an embodiment of the present invention.

Figure 23:
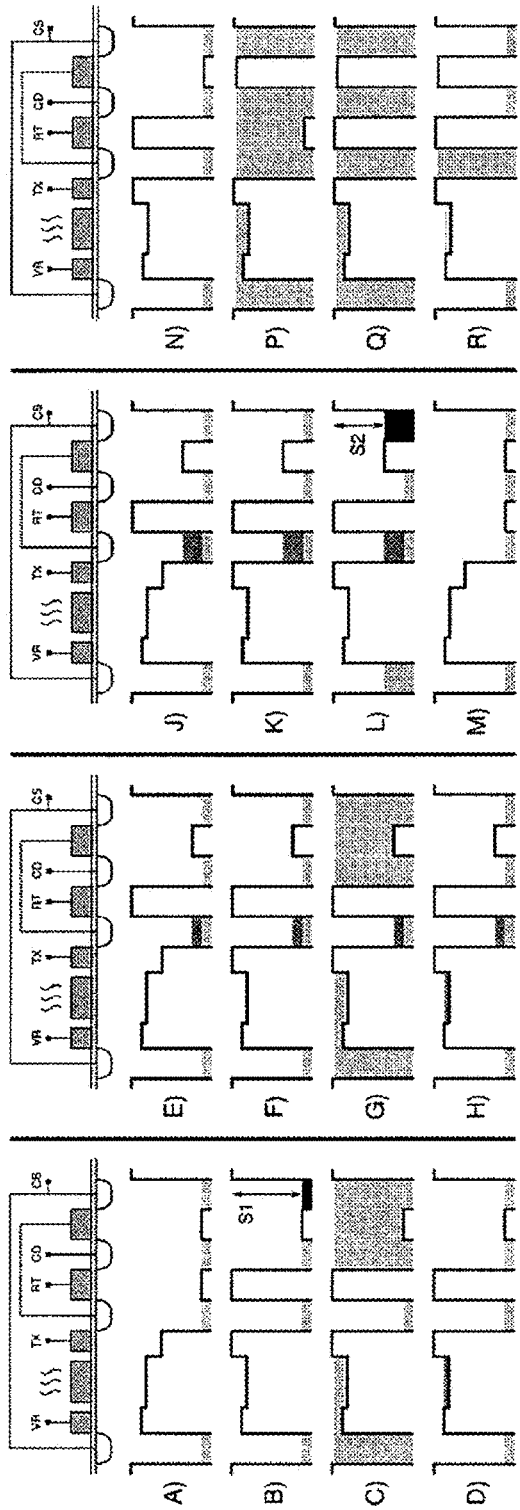

FIG. 23 shows surface potential diagrams for the pixel of FIG. 22 according to an embodiment of the present invention.

Figure 24:
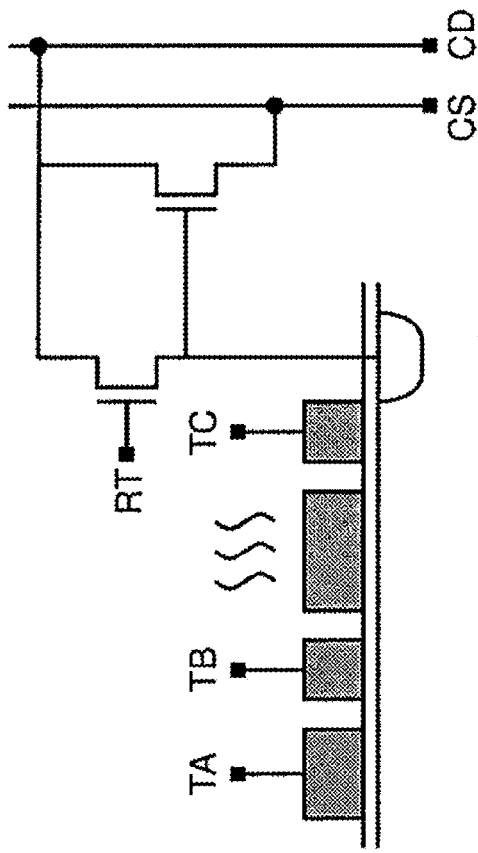

FIG. 24 shows an IS accumulation pixel with 2 transistors and 4 electrodes according to an embodiment of the present invention.

Figure 25:
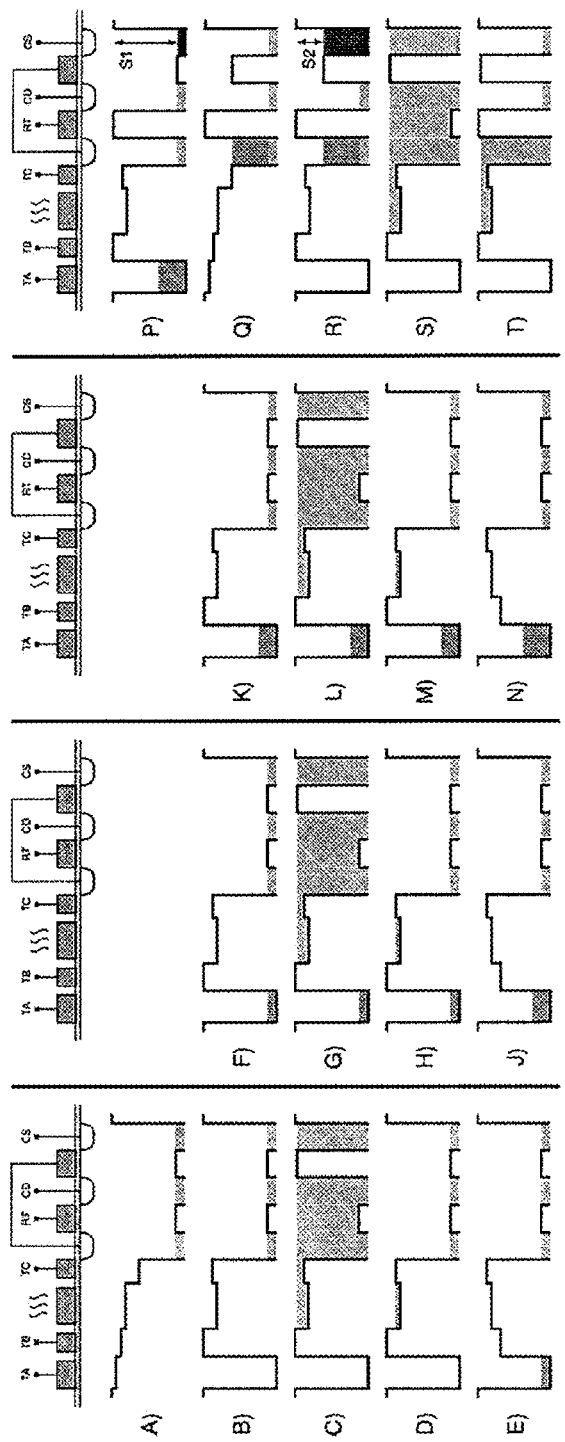

FIG. 25 shows the surface potential diagrams for the pixel of FIG. 24 according to an embodiment of the present invention.

Figure 26:
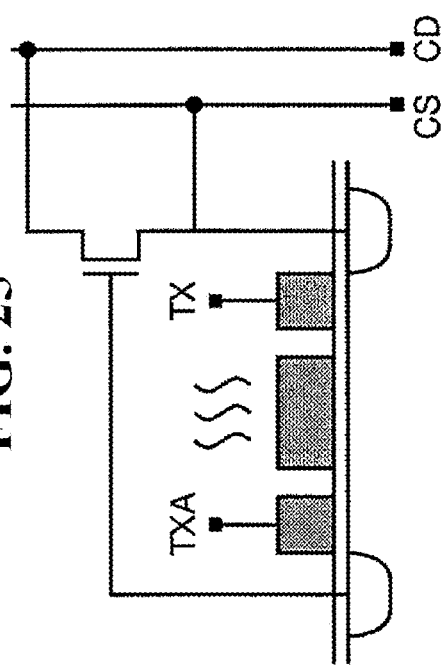

FIG. 26 shows an IS accumulation pixel with 1 transistor and 3 electrodes according to an embodiment of the present invention.

Figure 27:
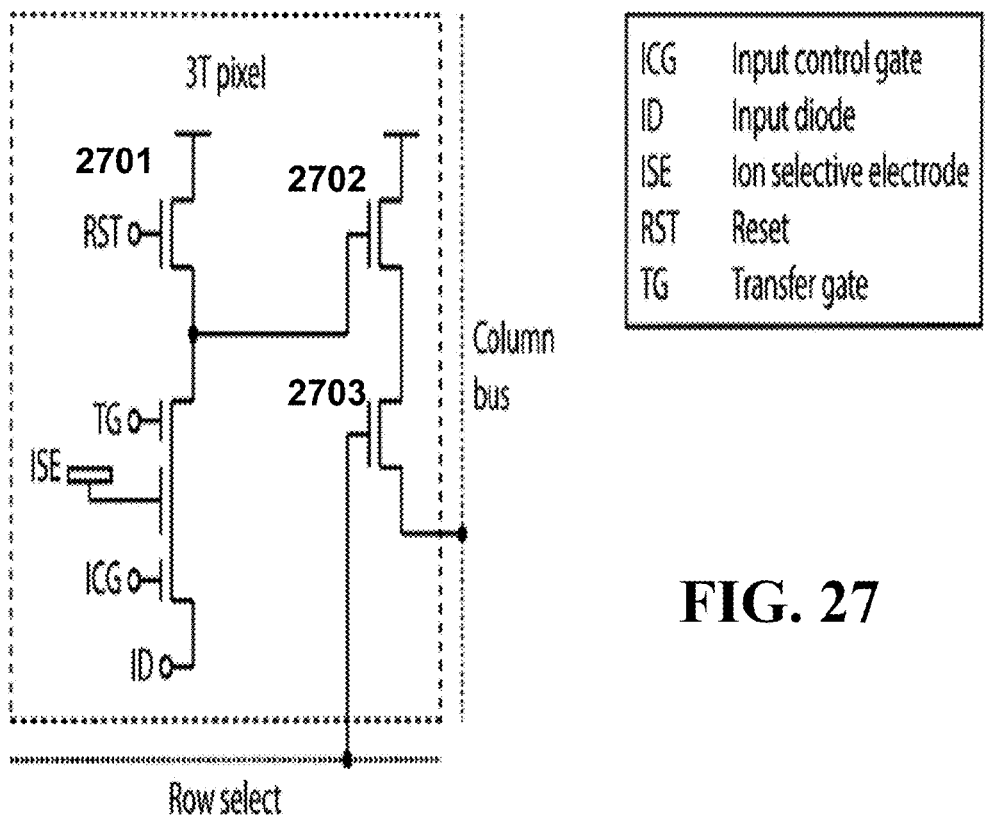

FIG. 27 shows a three transistor (3T) active pixel sensor according to an embodiment of the present invention.

Figure 28:
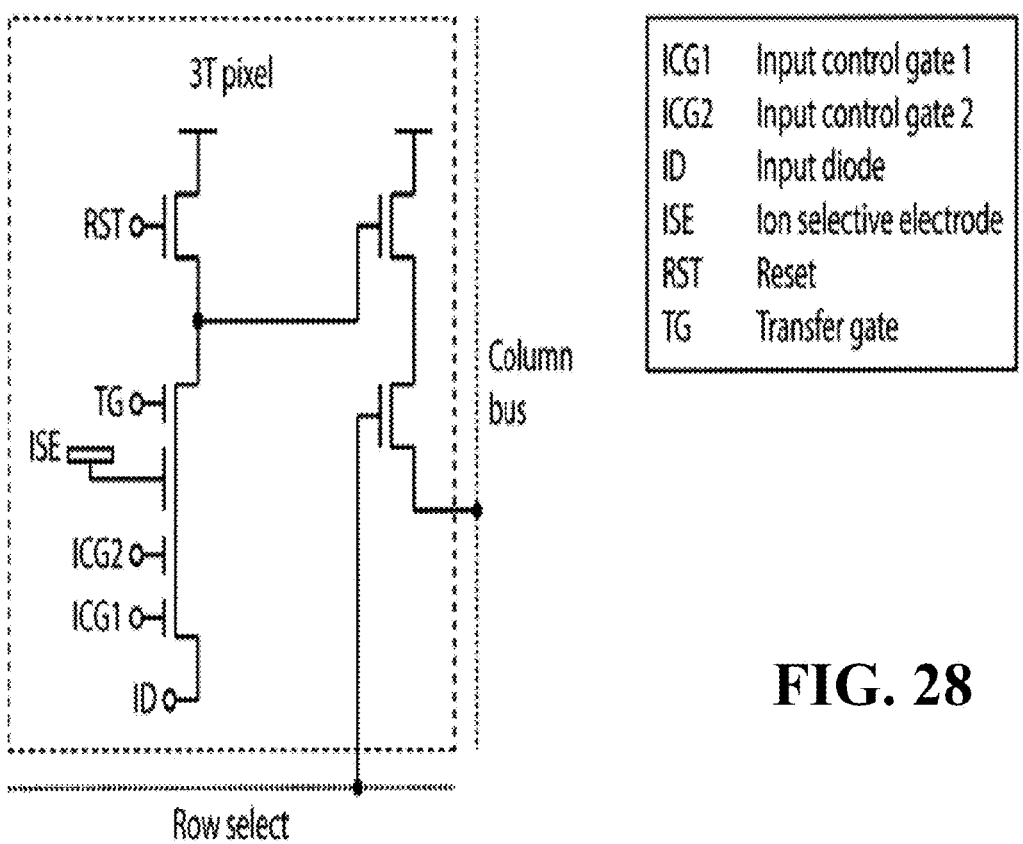

FIG. 28 shows an alternate embodiment of a 3T active pixel sensor.

Figure 29:
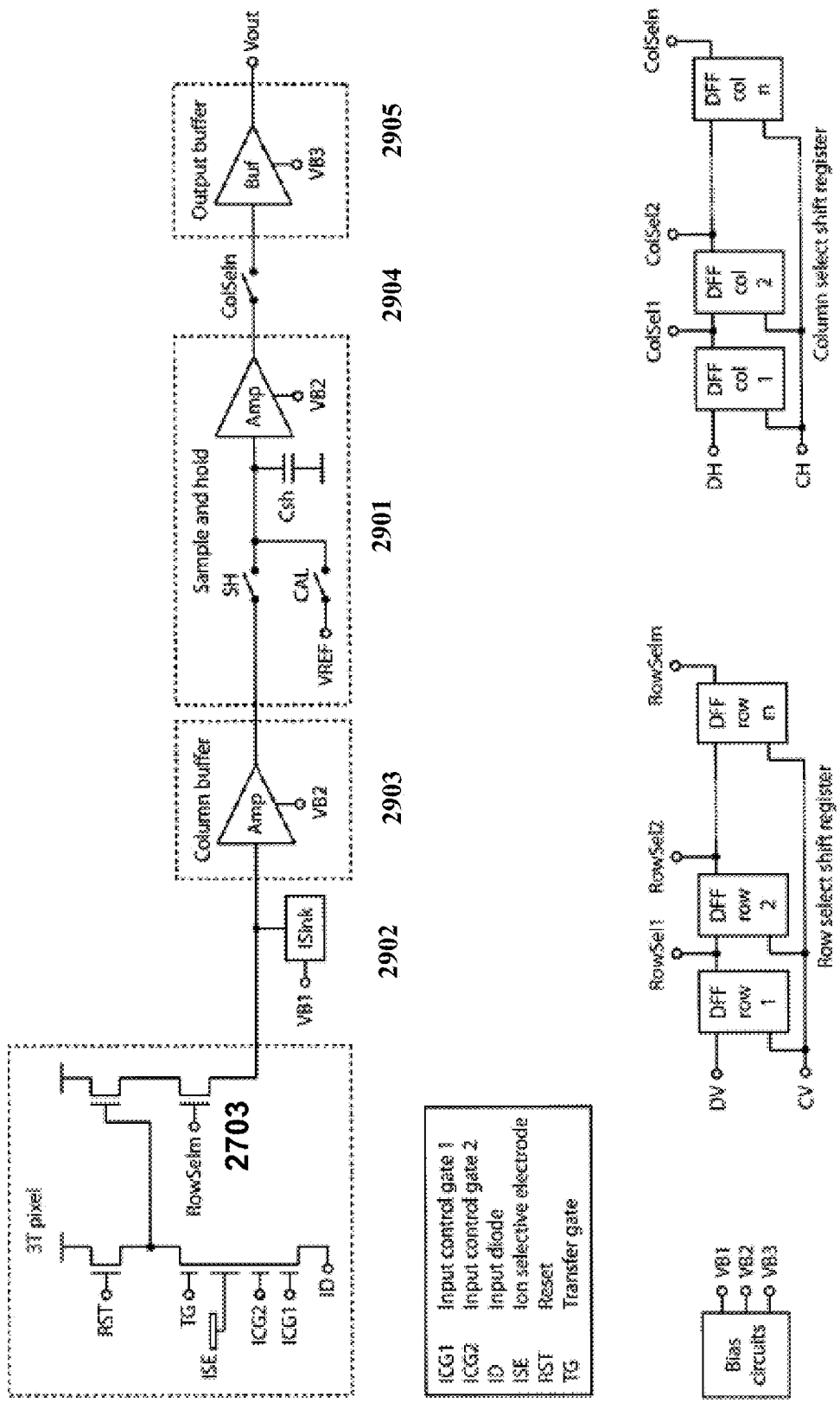

FIG. 29 shows a 3T active pixel sensor with a sample and hold circuit according to an embodiment of the present invention.

Figure 30:
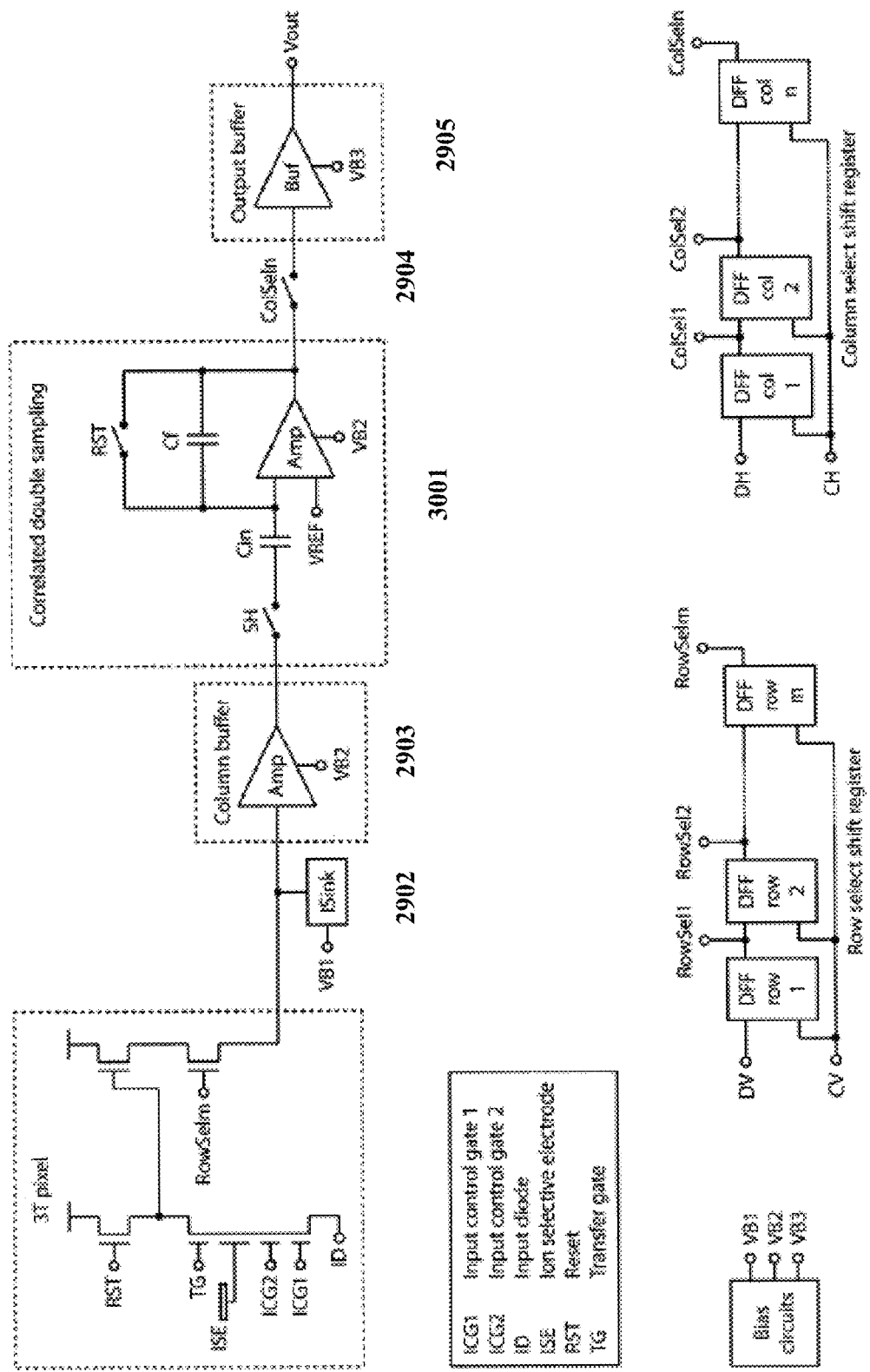

FIG. 30 shows a 3T active pixel sensor with a correlated double sampling circuit according to an embodiment of the present invention.

Figure 31:
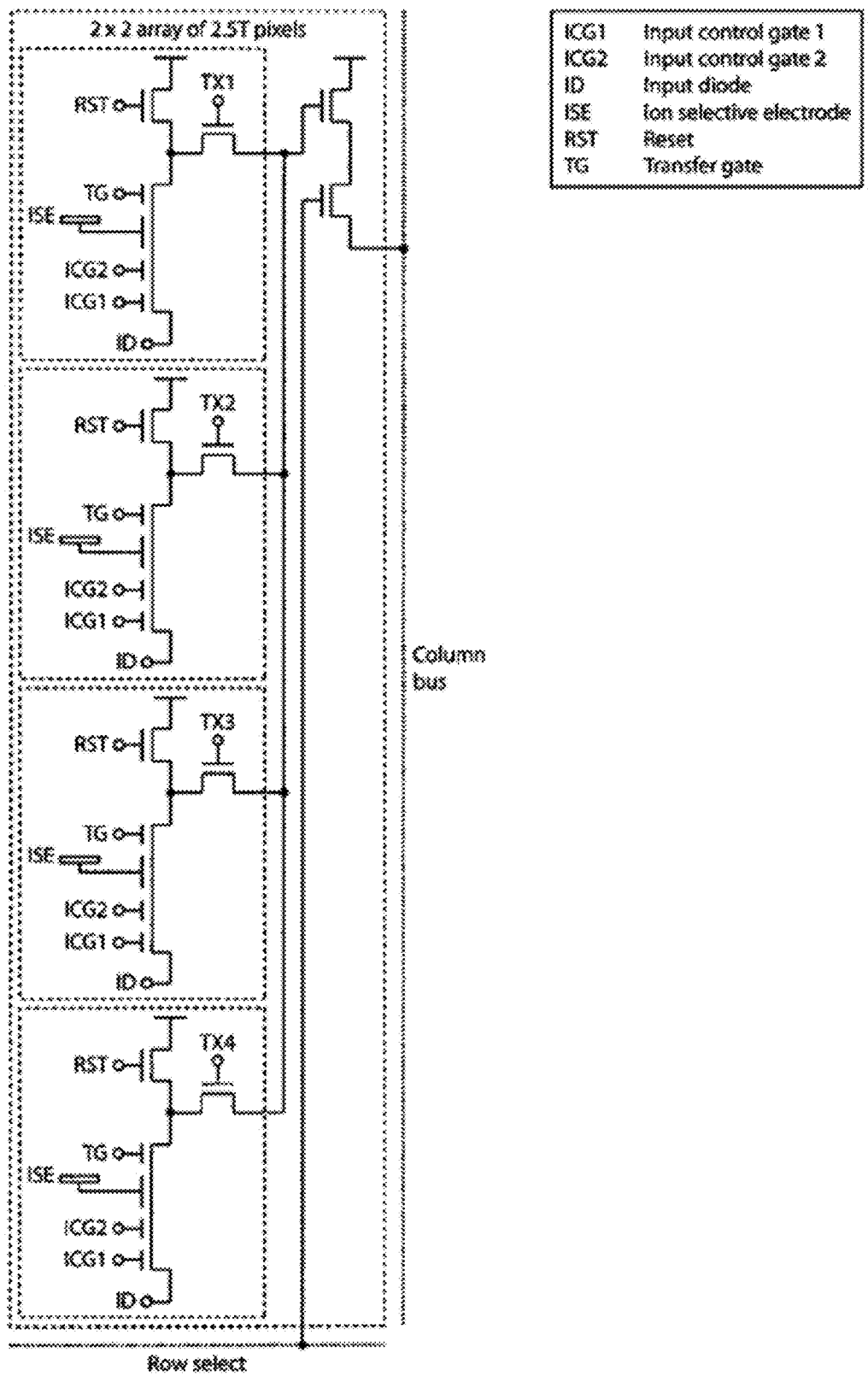

FIG. 31 shows a 2.5T active pixel sensor array according to an embodiment of the present invention.

Figure 32:
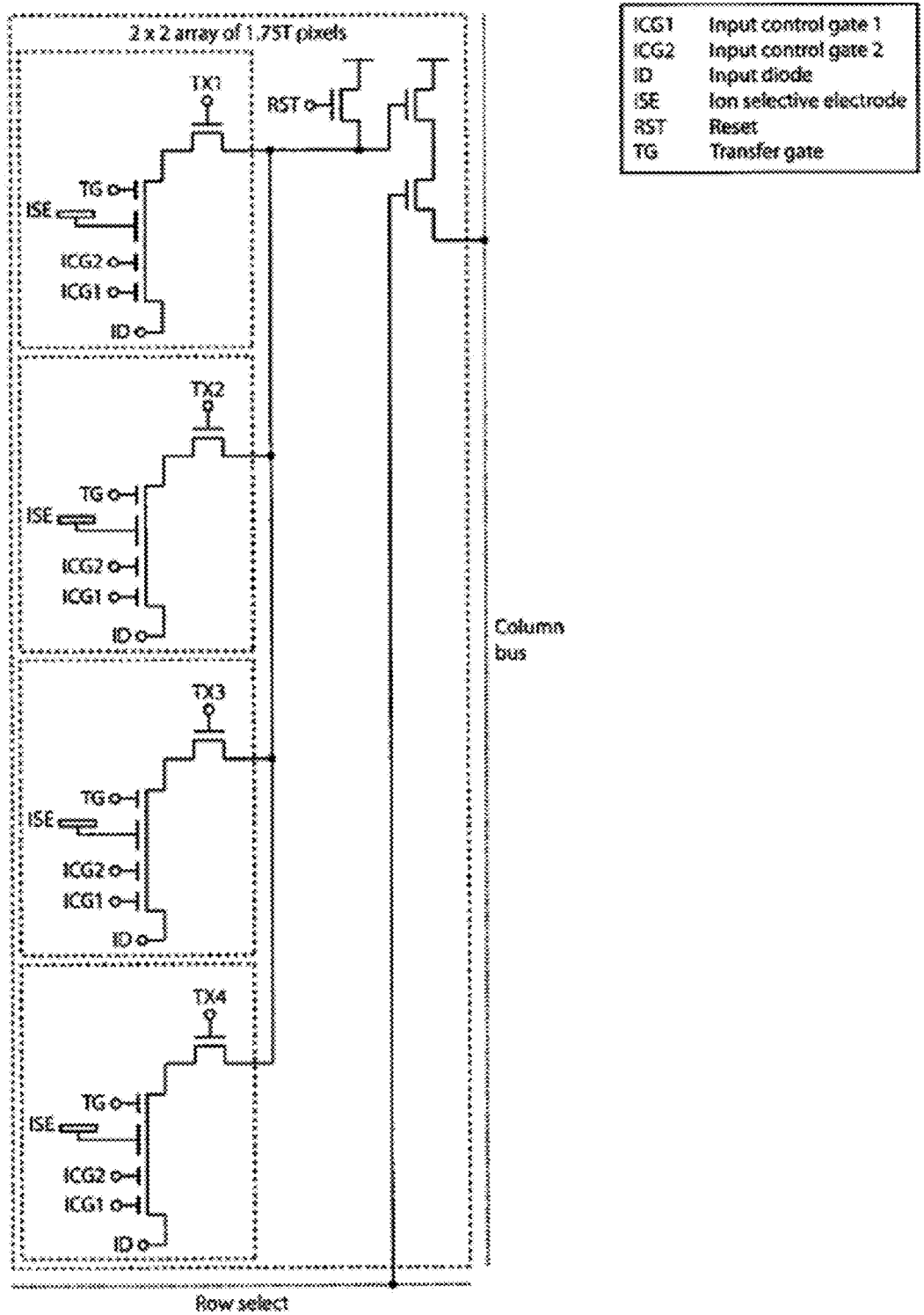

FIG. 32 shows a 1.75T active pixel sensor array according to an embodiment of the present invention.

DETAILED DESCRIPTION

One-Transistor Pixel Array

A floating gate (FG) transistor may be used to detect ions in close proximity to the gate electrode. The transistor may be configured with other transistors to form a pixel that can be placed into an array for addressable readout. In the simplest form, the ancillary transistors are used solely to isolate and select the floating gate transistor for readout in an array. The floating gate transistor may be a chemically-sensitive transistor, and more specifically, a chemically-sensitive field effect transistor (ChemFET). The ChemFET may be designed with a metal-oxide-semiconductor field-effect transistor (MOSFET) containing self-aligned source and drain implants fabricated using standard complementary metal-oxide-semiconductor (CMOS) processing. The ChemFET may be an ion sensitive FET (ISFET), and may be a PMOS or an NMOS device.

To reduce the pixel size to the smallest dimensions and simplest form of operation, the ancillary transistors may be eliminated to form an ion sensitive field-effect transistor (ISFET) using one transistor. This one-transistor, or 1T, pixel can provide gain by converting the drain current to voltage in the column. Parasitic overlap capacitance between terminals of the transistor limits the gain. The capacitance ratios also allow consistent pixel-to-pixel gain matching and relatively constant current operation which justifies the use of a row selection line which can sink the necessary current without causing unacceptable variation. Derivatives of this allow for increased programmable gain through a cascoded transistor enabled during readout. Configurable pixels can be created to allow both common source read out as well as source follower read out.

Figure 1:
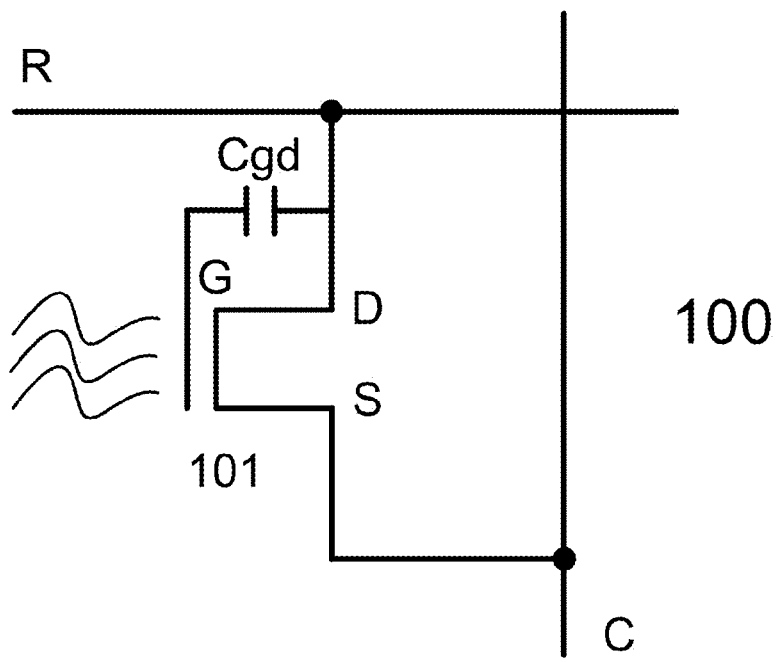
FIG. 1 illustrates a 1T ion sensitive pixel according to an embodiment of the present invention.

FIG. 1 illustrates a 1T ion sensitive pixel according to one embodiment of the present invention. As shown, the pixel 100 may have one and only one transistor 101, one and only one row line R and one and only one column line C. The transistor 101 is shown as an n-channel MOSFET (NMOS) transistor in a p-type epitaxial substrate available using standard CMOS processes in this embodiment. It should be understood that NMOS is only used as an example in the present invention, and the transistor 101 may be a PMOS as well. The selection of NMOS or PMOS as a preferred device depends on which device does not require a top-side bulk contact for a given process. Typically NMOS is preferred when using a P+ wafer with P− epitaxy layer (called an epi-wafer) because the underlying P+ substrate biases the bulk on an array of pixels without the need to wire in a bulk contact at each pixel location. Therefore, a global bulk contact is an attractive combination for use with a 1T pixel where a small pixel pitch is required. The floating gate G of the transistor 101 may contain trapped charge, which may be properly discharged such that the electrode is at approximately the same potential as the substrate when all other terminals are also biased to the substrate potential. The row line R may be capacitively coupled to the drain D of the transistor 101, and the column line may be coupled to the source S of the transistor 101. A gate to drain overlap capacitance Cgd may form between the gate G and the drain D. The pixel 100 may be addressable from the row line R, which supplies the column current (i.e., drain-to-source current of the transistor 101) and boosts the potential at the floating gate.

Figure 3:
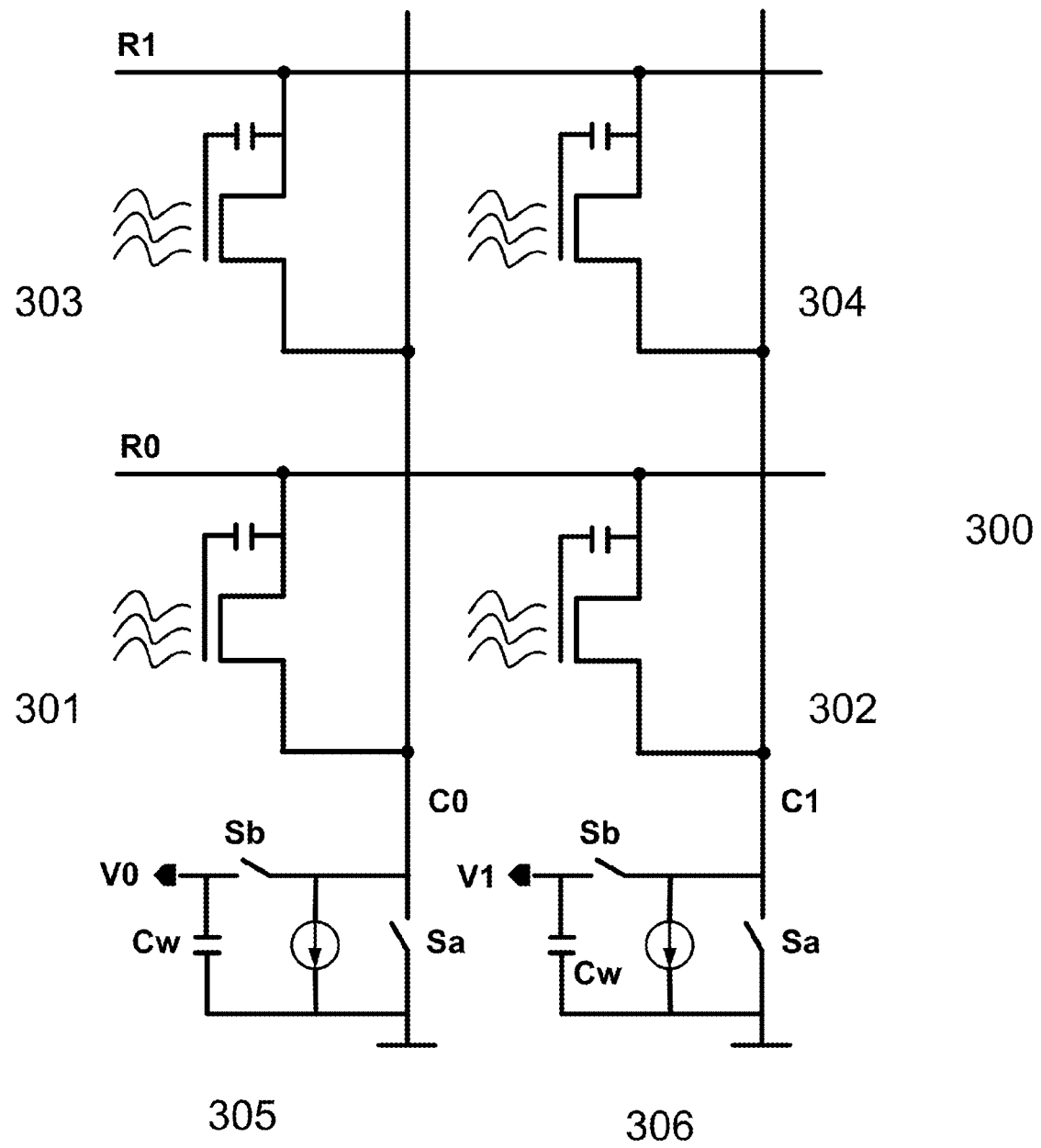
FIG. 3 shows the schematic of an array of pixels with column readout switches according to an embodiment of the present invention.

In a one-transistor pixel array, such as the one shown in FIG. 3, row selection may be facilitated by boosting the FG nodes for a particular row. In one embodiment, the readout of the pixel is a winner-take-all circuit, which will be described below.

Figure 2:
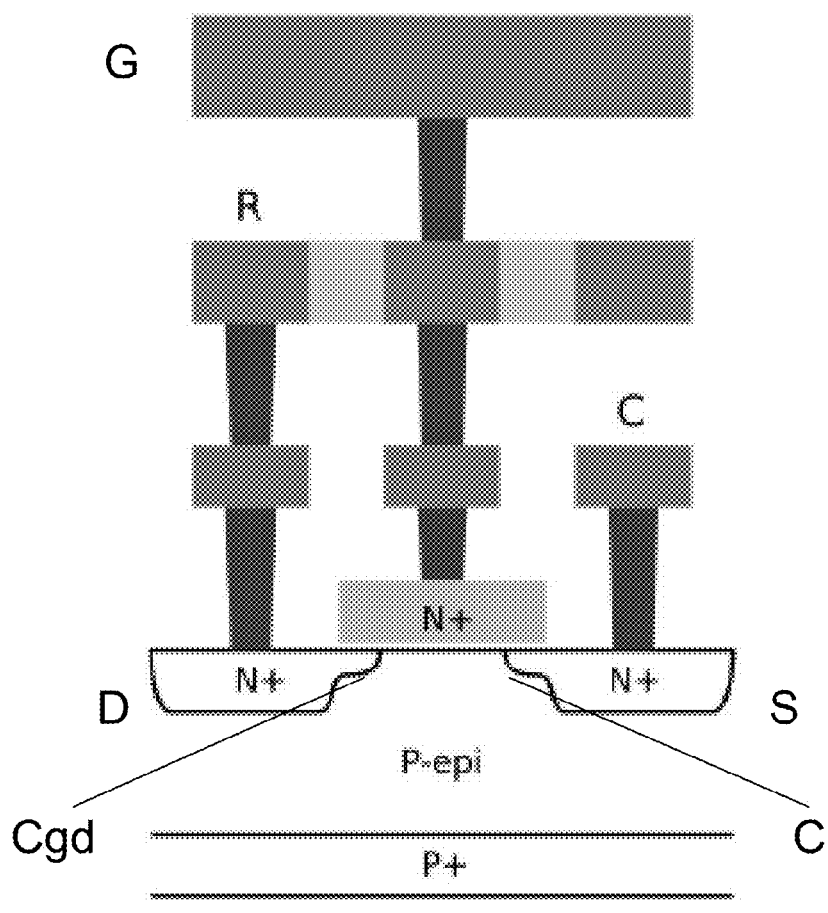
FIG. 2 illustrates the cross section of a 1T pixel according to an embodiment of the present invention.

FIG. 2 illustrates the cross section of a 1T pixel according to one embodiment of the present invention. The transistor in the 1T pixel may be formed using an n-channel FET device by having a drain D and a source S formed using n-type implants within a p-type semiconductor. As shown, the transistor may have a floating gate G, the drain D and the source S. The source S may be coupled to the column line C and the drain D may be coupled to the row line R. Lightly doped drain (LDD) regions may create a gate to drain overlap capacitance Cgd and/or a gate to source overlap capacitance Cgs.

In one embodiment, the 1T ion pixel 100 may work by boot-strapping the row selection line R to the floating gate G while at the same time providing a source of current for the column line bias. In the simplest form, this bootstrapping occurs without adding any extra capacitors. The gate to drain overlap capacitance Cgd, as shown in FIGS. 1 and 2, may naturally form the necessary capacitive coupling. To increase capacitive coupling, if desired, the row selection metal line can form an extra metal capacitor to the floating metal electrode or more significant source and drain extensions can be made with ion implantation.

FIG. 3 shows the schematic of an array of pixels with column readout switches according to one embodiment of the present invention. For illustrative purposes, four 1T pixels 301, 302, 303 and 304 of an array 300 are shown arranged into two rows and two columns, though the array 300 could extend to an array of any size of 1T pixels. The 1T pixel may be similar to the one shown in FIG. 1. The drains of pixels 301 and 302 are coupled to a row line R0, and the sources of pixels 301 and 302 are coupled to column lines C0 and C1 respectively. The drains of pixels 303 and 304 are coupled to a row line R1, and the sources of pixels 303 and 304 are coupled to column lines C0 and C1 respectively. The pixel array can be loaded with a current source but the simplest implementation makes use of just a single switch that precharges the column line to a low potential such as the substrate potential. A column readout switch 305 is coupled to the column line C0 and a column readout switch 306 is coupled to the column line C1. The column readout switch 305 comprises a switch Sa, a switch Sb, a current source Isource and a capacitor Cw. The switch Sa is used for precharging the column line and to initialize the column line quickly between samples. The switch Sb is used to sample and hold the analog value that is read on the column line. In some cases, neither a sampling capacitor nor a switch Sb are required if the pixel is converted to digital through and analog to digital converter while the pixel is held under bias. The switch Sa is used to ground the column line C0. After the column line switch Sb is open the sample is held in the capacitor, the final value on the column line, as sampled by the capacitor, will be determined almost entirely by the active row because the circuit operates according to "a winner take-all" mode (i.e., the resulting voltage represents the largest voltage of the ISFETs coupled to the readout circuit). The column readout circuit 306 functions similarly.

The operation of this pixel depends on the fact that the signal range of any given pixel is small compared to the supply voltage or read range of the source follower. For example, the useful signal range may be only 100 mV and the supply voltage may be 3.3V. When a row is selected, the R line is driven to an active high voltage VH, while all other row lines are held at an active low voltage VL. The voltage VL is selected to be approximately equal to the nominal voltage on the column line C during the readout of any given pixel. Because the signal range is small, this voltage is known to within 100 mV in this example. Therefore, the drain to source voltage of all inactive pixels is always held to small values. This point is only critical if the gate to source voltage of inactive pixels is near the threshold of the device. For the row driven to VH, the FG voltages for that row are significantly higher than the other rows because of the bootstrapping that occurs when the row line transitions to VH. After the column line switch Sb is open, the final value on the column line will be determined almost entirely by the active row because the circuit operates according to the winner take-all mode.

There are two sources of current from other rows that can distort the signal value (one that adds current and one that takes away current) and there must be enough bootstrapping available to successfully read pixels without significant interaction from the other rows that produce these sources. The analysis to determine how much bootstrapping is needed is as follows. By the time the pixel is sampled, the device has entered the subthreshold region of operation which has a transconductance slope, for example, of approximately 100 mV/decade. This means that for every 100 mV of change in gate voltage, the current changes by 10 times. In order to effectively read a single pixel, a criteria is set so that 99% of the current on the column line is attributable to the active row and only 1% is attributable to the inactive rows (distortion current). From here it can be determined how much bootstrapping is necessary. With only 2 rows in the pixel array, a 200 mV difference in the floating gate voltages is needed according to the subthreshold slope. Since a signal range of about 100 mV is also needed to be accounted for, the total requirement is about 300 mV. If there are 10 rows, there may be 10 times more contribution from inactive rows. Therefore an extra 100 mV is needed. If the array is increased to 100 rows, another 100 mV is needed. If the array is increased to $10^n$ rows, 300+100*n mV is needed. As an example, a 10000 ($10^4$) row pixel array only requires a total of 700 mV (300+100*4) of bootstrapping. This amount of bootstrapping can be achieved from the overlap capacitance of the gate and drain. If more capacitance is needed, extra coupling can be facilitated in the mask layout. The above analysis only applies to pixels contributing to the readout current.

Pixels can also take current away from the column line and sink it through the deactivated row lines. Since the deactivated row line is set to approximately the level of the column line, this current draw will be minimal but it must still be quantified and controlled. To accomplish this, the final current on the column line should not be allowed to diminish beyond a certain level. This is ensured by loading the column with a small current sink such as 1 uA. For a W/L (width to length) ratio of 1, a transistor biased at its threshold will have a saturation current of about 0.1 uA. This current decreases by a factor of 10 for every 100 mV of reduction in gate to source voltage. If less than 1% contribution of current is required, the VGS of inactive pixels needs to be kept to 100+100*n mV below the threshold voltage where $10^n$ is the number of pixels in the row. Thus, for a 10000 row pixel array, VGS needs to be kept to 500 mV below threshold. A typical 3.3V NMOS transistor has a VT of 600 mV. Therefore, VGS should be less than 100 mV for inactive pixels. Assuming that the FG has a nominal voltage of 0V when the row (R) and column (C) lines are at 0V, this condition is met even as R and C couple to the FG. If the FG has a larger nominal voltage than 0V (for example, due to the trapped charge), more bootstrapping is necessary to cause the column line to reach a level within 100 mV of the FG. As long as the nominal FG voltage is sufficiently low, the second criteria for minimizing distortion current is not a limiting factor. Finally, enough bootstrapping is needed to produce a current on the column line that matches the bleeding current so that the pixel can produce a measurable voltage on the column line. If VG is nominally 0 v, then 700 mV is needed for bootstrapping. Therefore, for an NMOS with VT as large as 600 mV, the amount of bootstrapping required is simply limited by the VT. In order to readout the pixel with margin, a good target for bootstrapping is 1V. This leaves 300 mV of range for variation. Achieving 1V of bootstrapping is practical within a 3.3V supply.

All the current from the column readout is distributed through the row line. This causes significant droop in the voltage of the row line if the column current is also significant. The voltage droop affects the bootstrapping level but is not detrimental to the readout of the source follower because variation in drain voltage has only a second order effect. Since pixels are read out with multiple samples, offsets are canceled such that the droop does not affect the sensitivity of the pixels.

It should be noted that the same layout can be used for both source follower readout and common source readout as long as optimizations are not made for either. Only accommodations that need to be made are in the column circuits. This makes for a flexible readout architecture and either readout method may be used depending on the necessary signal range. If the signal needs a high gain, the common source mode should be used. Otherwise, the source follower mode may be used.

Figure 4:
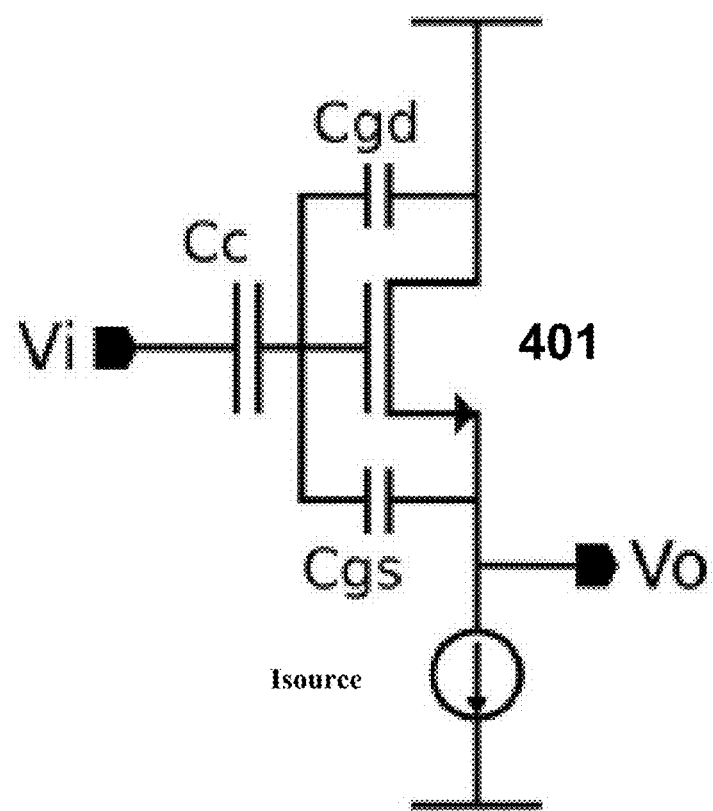
FIG. 4 shows the source follower configuration of the 1T pixel according to an embodiment of the present invention.

FIG. 4 shows the source follower configuration of the 1T pixel according to one embodiment of the present invention. The source follower mode has a buffered readout and operates in a voltage mode, and has a gain less than 1. As shown, the sole transistor 401 may be coupled to an input voltage Vi at its gate G and to a fixed voltage at its drain D. The source S of the transistor 401 may be grounded via a current source Isource. The output voltage Vo may be taken from the source of the transistor 401. A coupling capacitance Cc may exist between the input and the gate of the transistor 401, a parasitic capacitor Cgd may exist between the gate G and the drain D of the transistor 401, and a parasitic capacitor Cgs may exist between the gate and the source S of the transistor 401.

The following analysis is given for the gain of the source follower readout. Referring to FIG. 4, the gain of the circuit (G) may be defined as Vo/Vi. Using reference pixels the electrode of the system may be swept to measure the gain such that Vo/Vi=G. Using the measured value of a parameter G, which is 0.65 in this example, the ratio of Cc to Cgd may be determined. As will be discussed later, it is this ratio that will determine the gain in the common source mode. The input capacitance of the source follower is Ci=Cgd+Cgs(I–Asf), wherein Asf is the gain of source follower. Due to the body effect, Asf is approximately 0.85. The capacitive divider relating to the input voltage on the FET is Cc/(Ci+Cc) and therefore, Cc/(Ci+Cc)=G/Asf. Since Cgs is about 3-5 times larger than Cgd and Asf is about 0.85, Ci is approximately 2 Cgd. Therefore, Cc=2 Cgd(G/(Asf–G)). In this example, the ratio of Cc to Cgd is about 6.5.

In one embodiment, the present invention obtains voltage gain by reading out with the common source configuration. It is desirable to achieve both a reduction in pixel size as well as an increase in signal level. The present invention eliminates the ancillary transistors in other pixel designs (e.g., 2T and 3T discussed below) and uses the source of the ISFET as the selection line to achieve both of these goals. The common source mode is a gain mode and a current mode.

Figure 5A:
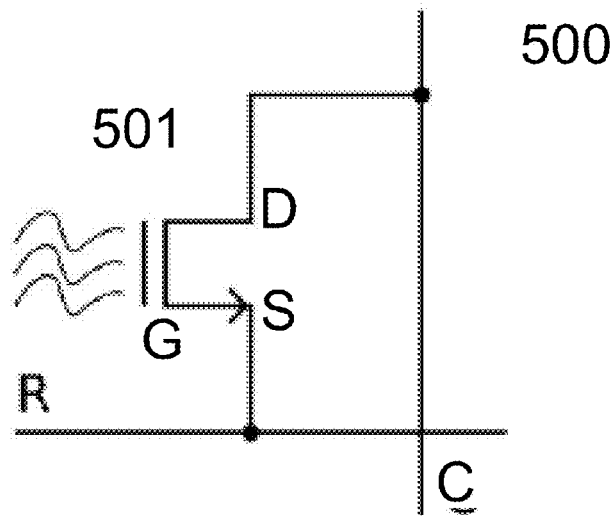
FIG. 5A shows a 1T common source ion sensitive pixel according to an embodiment of the present invention.

FIG. 5A shows a 1T common source ion sensitive pixel according to one embodiment of the present invention. As shown, the pixel 500 may have one and only one transistor 501, one and only one row line R and one and only one column line C. The transistor 501 is shown as an n-channel MOSFET (NMOS) transistor in a p-type epitaxial substrate available using standard CMOS processes in this embodiment, although it may be a p-channel MOSFET as well. An NMOS device is typically preferred in use with a P+ epi wafer that requires no front side bulk contacts. Technically a PMOS could be use with a N+ epi wafer, but this configuration is not as commonly produced in standard CMOS processes. The row line R may be coupled to the source S of the transistor 501, and the column line may be coupled to the drain D of the transistor 501. The row selection is facilitated by switching on a path for the source voltage, and the readout of the pixel is through the drain.

Figure 6:
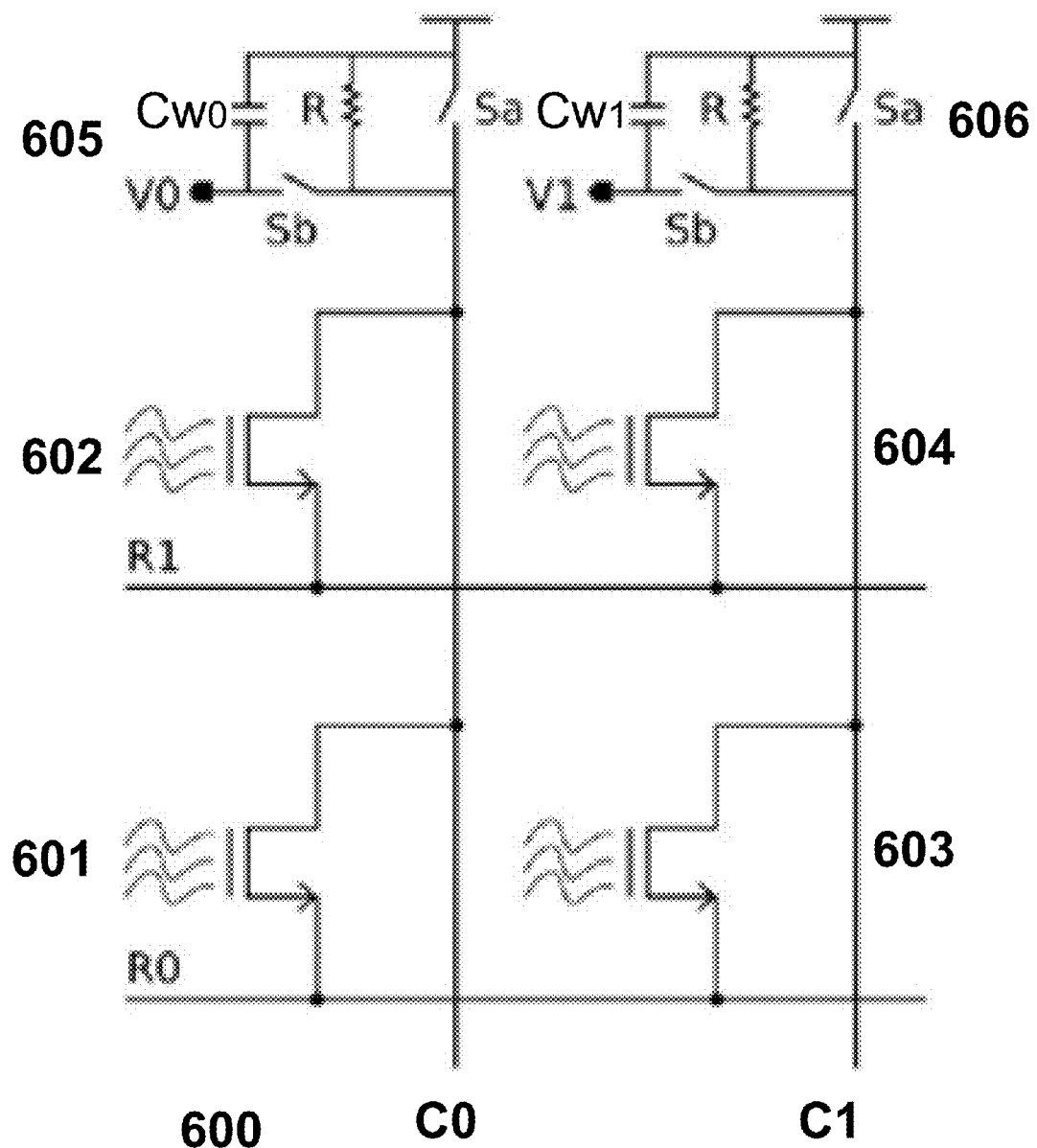
FIG. 6 shows a schematic of an array of pixels with column readout switches according to an embodiment of the present invention.

The schematic of an array of pixels with column readout switches according to one embodiment of the present invention is shown in FIG. 6. The array 600 has four 1T common source pixels 601, 602, 603 and 604. The 1T pixel may be similar to the one shown in FIG. 5A. In this example, pixels are arranged into two rows and two columns. The drains of pixels 601 and 602 are coupled to a column line C0, and the sources of pixels 601 and 602 are coupled to row lines R0 and R1 respectively. The drains of pixels 603 and 604 are coupled to a column line C1, and the sources of pixels 603 and 604 are coupled to row lines R0 and R1 respectively. A column readout switch 605 is coupled to the column line C0 and a column readout switch 606 is coupled to the column line C1. The column readout switch 605 comprises a switch Sa, a switch Sb, a resistor R and a capacitor $C_{w0}$. The column readout switch 606 comprises a switch Sa, a switch Sb, a resistor R and a capacitor $C_{w1}$. The switch Sa may pull the voltage on the column line to a fixed voltage, for example, to a 3.3V supply. When the column line switch Sb is open, the final value on the column line will be determined by the active row since the switch Sb, along with the capacitor $C_{w0}$, acts as a sample and hold circuit.

The pixel array can be loaded with a current source with finite output resistance or another load device such as a resistor. Normally the row selection lines will be held at an active high voltage VH. When a row is selected for readout, its row selection line is pulled low to VL. The value of VL is set such that the nominal current level is about 1 uA. If the FG has a value of 100 mV higher than the norm, 10 times this current will result on the column line. If the value of FG is 100 mV lower than the norm, the current will be 10 times lower. The settling time of the signal on the column line will be signal dependent. The voltage gain is achieved with the selection of the value of R and it can be configurable to achieve programmable gain. For example, if R is 100 k ohms, then the 100 mV, translates to 1V at the output.

The actual circuit is more complicated than just a simple common source amplifier because of the parasitic capacitance involved. Since the FG node is not driven, but rather capacitively coupled to the output, there is a feedback mechanism that limits the gain. This limit is roughly equal to the total capacitance at the FG node to the gate to drain capacitance. This ratio may be about 3. It could be designed to achieve higher gain such as 10 times with careful mask operations to reduce source and drain extensions.

Figure 7A:
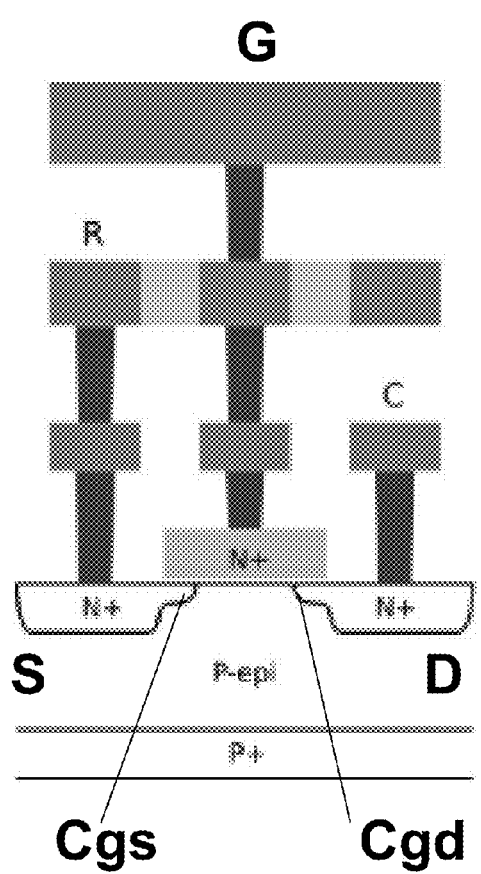
FIG. 7A shows a cross section of a 1T common source pixel according to an embodiment of the present invention.

FIG. 7A shows the cross section of a 1T common source pixel according to one embodiment of the present invention. The transistor in the 1T pixel may be formed using an n-channel FET device by having a drain D and source S be formed using n-type implants within a p-type semiconductor. As shown, the transistor may have a floating gate G, the drain D and the source S. The source S may be coupled to the row line R and the drain D may be coupled to the column line C. Lightly doped drain (LDD) regions may create a gate to source overlap capacitance Cgs and a gate to drain overlap capacitance Cgd.

Figure 7B:
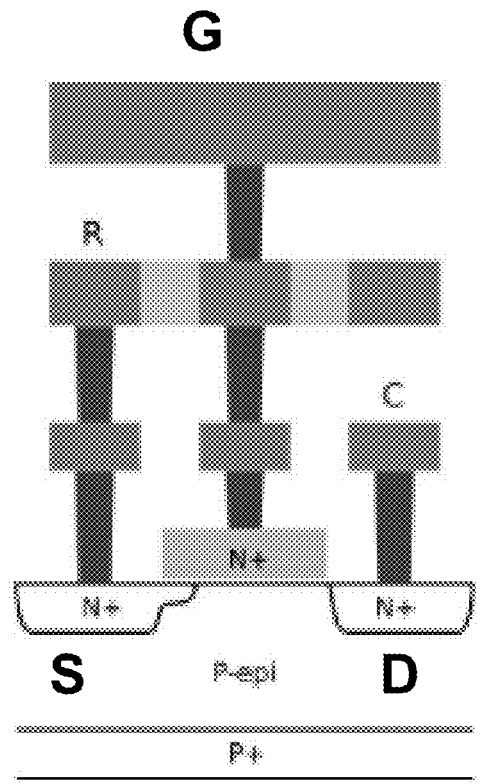
FIG. 7B shows a cross section of a 1T common source pixel according to an embodiment of the present invention.

The overlap capacitance created by the LDD regions can be reduced by skipping the LDD implants at the drain for the device. FIG. 7B shows the cross section of a 1T common source pixel according to one embodiment of the present invention. FIG. 7B shows a drain node with a missing LDD region. This missing region reduces the capacitance and increases gain. This can be achieved through masking out the LDD implants and can be implemented in standard CMOS processing.

Figure 10:
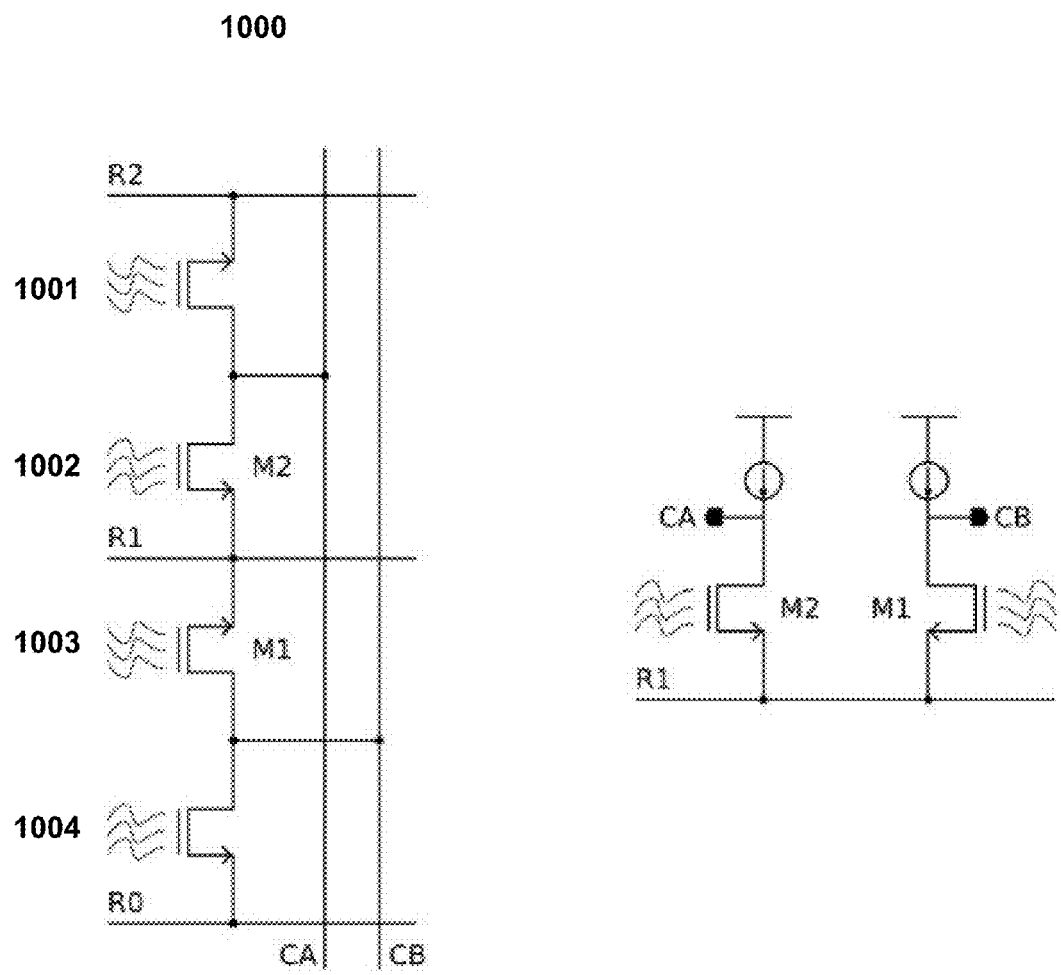
FIGS. 10A and 10B show a one-transistor pixel array according to an embodiment of the present invention.

In the 1T pixel shown in FIG. 5A, since the source current must be supplied from the row selection line, variations in current due to variations in signal will create variations in voltage. These variations can distort the measurements. Therefore the row selection line should be low resistance and the driver for that line should also supply a steady source voltage independent of the current load. Where this is not possible, the current can be supplied from the column line and a second selection transistor can be added to form a 2T pixel for common source read out, as shown in FIG. 10A described below. Since the gain is limited by the parasitic overlap capacitance, it is expected that the best load to use is a current source implemented with transistors of high output resistance. In this case, relatively constant current will be maintained in all devices since the gain is achieved through capacitor ratios. This makes the 1T configuration feasible since voltage variation at the source is minimal, even with a single row selection line that carries all the current.

Figure 5B:
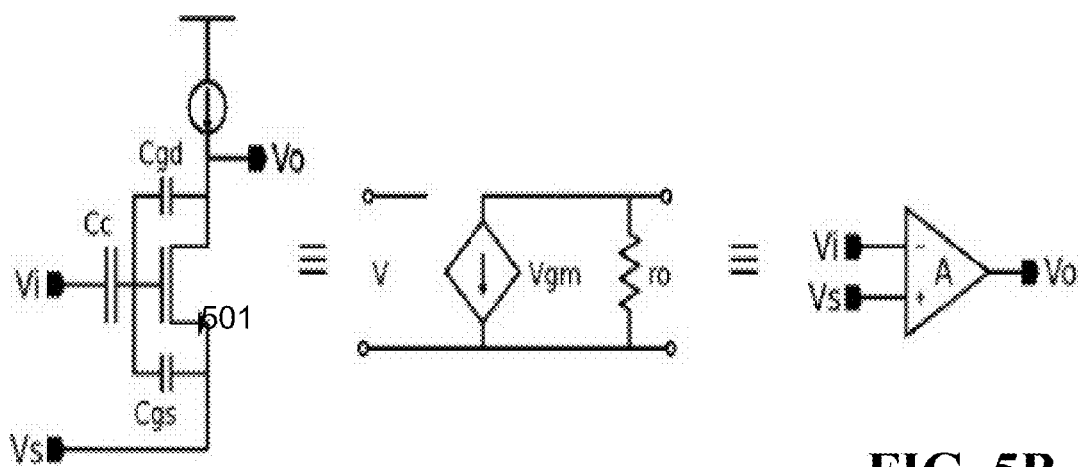
FIG. 5B shows the pixel in a common source readout configuration according to an embodiment of the present invention.
Figure 5C:
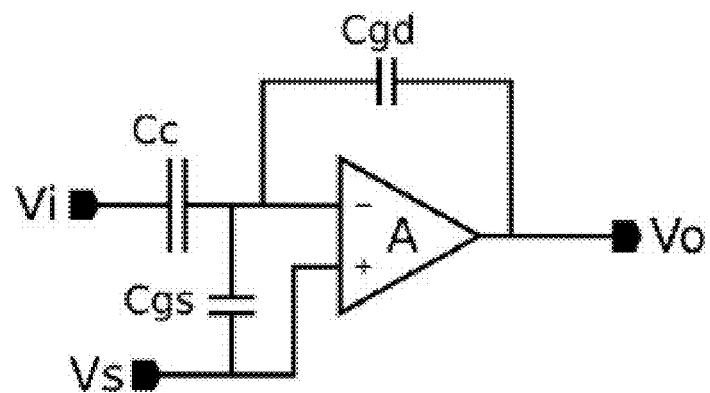
FIG. 5C shows a common source equivalent circuit according to an embodiment of the present invention.

The pixel in common source readout configuration is shown in FIG. 5B. The transistor forms an amplifier with negative voltage gain. This negative voltage gain forms a natural feedback loop with the parasitic capacitors in order to control the gain. The open loop gain of the amplifier is A=gm (ro), wherein gm is a transconductance. The value A is typically larger than 100 for a given bias condition and process technology. As shown in FIG. 5C, the common source equivalent circuit has a feedback capacitance Cgd, a coupling capacitance Cc, and Cgs.

Since A is large compared to the loop gain, the negative input terminal may be considered as a virtual ground node and the gain of the circuit may be determined as Vo/Vi=–Cc/Cgd. Since this ratio is known from the analysis or measured values of the source follower configuration, the gain may be determined to be about 6.5. However compared to the source follower, the gain is Vo/Vi=2/(Asf−G). In this example, a gain of 10 is realized over the source follower configuration. A lower bound on this gain is given by assuming that the input capacitance of the source follower is solely due to Cgd and that the Asf is equal to 1. In this case the gain is about 3. Since neither of these conditions is realistic, the gain is expected to always exceed this number. Thus, if the gain of the source follower configuration of a pixel is known, the gain of the common source configuration of this pixel is also known. In addition, the higher the gain, the more sensitive the pixel is. This makes the common source configuration preferable.

Flicker noise can be reduced by using a channel doping of the same type as the minority carrier. For example, an NMOS with a n-type implant produces a buried channel transistor. To shift the workfunction of the device, a P+ gate electrode can be used.

One-Transistor Pixel Array with Cascoded Column Circuit

One derivative of the one-transistor pixel allows for increased programmable gain through a cascoded transistor enabled during readout.

Figure 8:
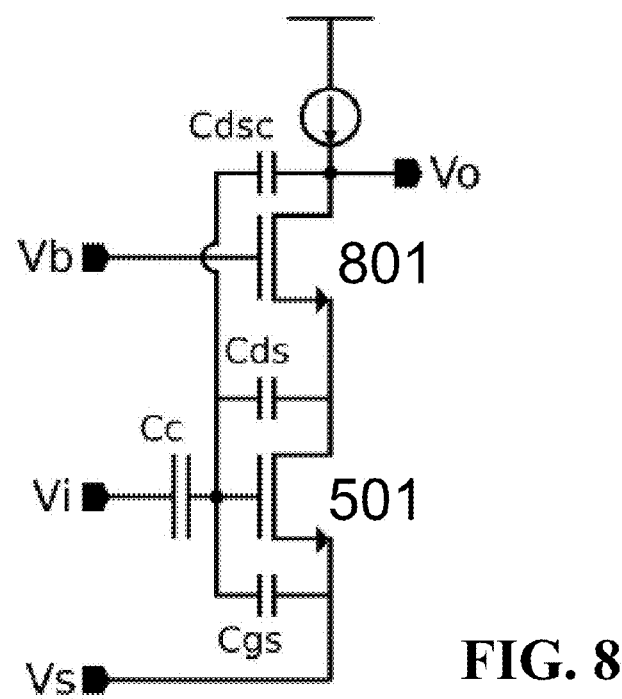
FIG. 8 shows a common source pixel with a cascoded row selection device according to an embodiment of the present invention.

Since the gain of the common source readout is limited by the Cgd capacitance, as shown in FIG. 5B, lowering this capacitance can increase the gain. FIG. 8 shows a common source pixel with a cascoded row selection device. As shown, a transistor 801 may be added to a common source pixel, e.g., the circuit shown in FIG. 5B. The gate of the transistor 801 may be coupled to a voltage Vb, and the source of the transistor 801 may be coupled to the drain of the transistor 501. The output voltage Vo may be taken from the drain of the transistor 801. The cascode effectively removes the Cgd capacitance from the feedback loop and replaces it with Cds which is much smaller. Gain on the order of the loop gain is then achievable, which may exceed 100.

Figure 9:
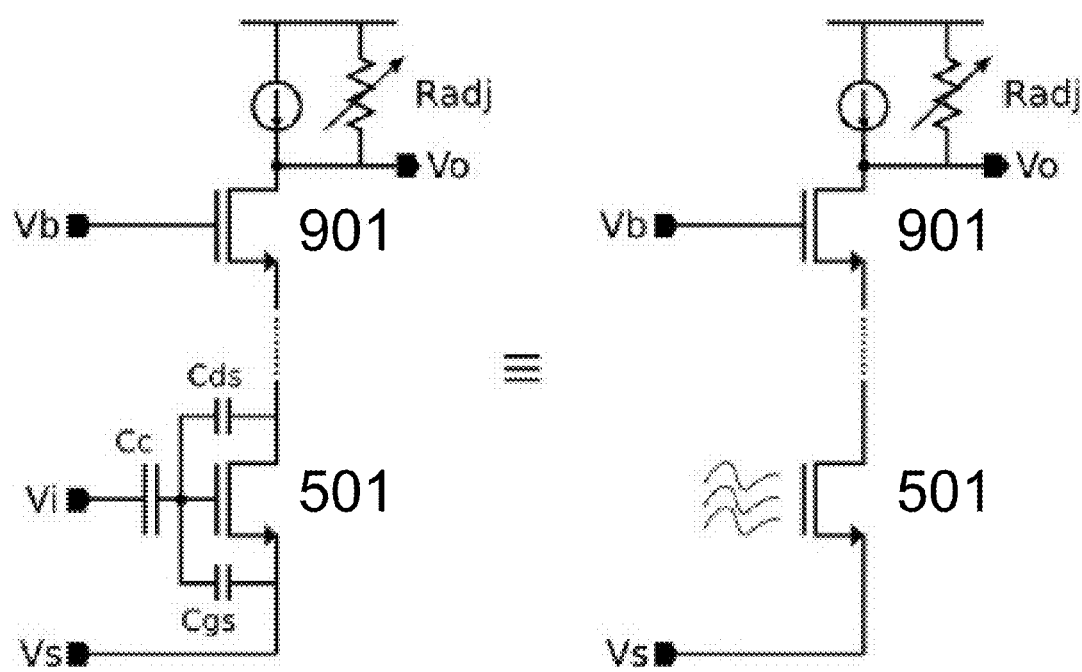
FIG. 9 shows a one-transistor pixel array with cascoded column circuit according to an embodiment of the present invention.

Higher gain and variable gain may be produced in the 1T configuration by bringing the cascode device outside the pixel to the column line. FIG. 9 shows a one-transistor pixel array with cascoded column circuit. This allows high gain and yet still allows the pixel pitch to be minimized with only 1 transistor per pixel. The shown pixel array is a column having a number of one-transistor pixels (e.g., 500) connected in series, and has a cascode device at the base of the array. The cascode device may comprise a transistor 901. The gate of the transistor 901 may be coupled to a bias voltage Vb, the source of the transistor 901 may be coupled to the drain of the transistor 501, and the drain of the transistor 901 may be coupled to a fixed voltage via a current source. The output voltage Vo may be taken from the drain of the transistor 901. It should be understood that the array may have a number of columns.

In this case, the cascode forces the drain of the pixel to remain at a fairly steady voltage over the range of inputs. This causes the pixel to push nearly all of the change in current through the cascode device at the base of the array and into the current load. This reduces the negative feedback from Cds, which would otherwise limit the gain. Given that the current load has infinite output resistance and there is effectively no coupling capacitor to the FG node, the gain of the pixel is now −(gm1rO1+1)gm2rO2, wherein gm1 is the transconductance of the cascode device at the base of the column line and gm2 is the transconductance of the pixel and rO1 and rO2 are the small signal output resistances as seen at the drain. The value of the output resistance is determined by channel length modulation. Longer gate lengths produce higher output resistance because the effect of channel length modulation is minimized. Since this gain is so large, it can be limited and configured by variation of the current source output resistance, which is shown as Radj in FIG. 9. This allows for programmable gain at the column level while maintaining a simple 1 transistor pixel. The gain of the pixel is then set by −gm2RL, assuming that the load resistance RL is much smaller than the output resistance of the cascode configuration, where $R_L$ is the adjusted value of Radj. The gain is now configurable and programmable within the range of 1 to 100 or larger. For example, if the bias current is about 5 uA, the transconductance of the pixel is about 50 uA/V, and a load resistance of 20K ohms is needed for gain of 1. A gain of 10 is achieved with a 200K ohm load and gain of 100 with a 2M ohm load. There are many was to implement the effect of the cascode device at the column line. The main purpose of the cascode, as shown in FIG. 901 as an NMOS transistor, is that the column line is held to a potential that is largely independent of the current level in the pixel. A differential amplifier with high gain can be applied to maintain this condition more precisely. This approach would be called gain-enhanced cascoding.

Various layout choices can be made to implement a 1 T and 2T transistor. In order to reduce the size of the pixel the source and drains of adjacent pixels can be shared. In this way a single row selection line enables 2 rows at a time. This reduces the row wiring: two columns are then read out at once for a given column pitch. Such a scheme is shown in FIGS. 10A and 10B. As shown, a pixel array 1000 comprises transistors 1001, 1002, 1003 and 1004 in a column. The source of 1001 is coupled to a row line R2, and the source of 1004 is coupled to a row line R0. Transistors 1001 and 1002 may form a mirror M1, and transistors 1003 and 1004 may form a mirror M2. The drain of 1001 and 1002 are coupled to a column line CA, and the drain of 1003 and 1004 are coupled to a column line CB.

In one embodiment, the cascoded device is gain-enhanced with a differential amplifier in feedback to control a transistor that maintains a constant voltage on the column line.

Two-Transistor Pixel Array

In a pixel array, a row selection device may be used for selection and isolation. When a row selection line is activated, the row selection device (a MOSFET) forms a channel due to the gate voltage exceeding a threshold voltage and acts like a switch. When the row selection is deactivated, the channel is diminished. It is important to note that a row selection device never really completely turns "on" or "off". It only approximates a switch. When the gate is substantially lower than the source of the row selection transistor, good isolation is achieved and the pixel with the active row selection can be read effectively without input from deactivated pixels. With many rows in an array of pixels, it is necessary to achieve a given level of isolation for each row selection device. That is, the requirements for the row selection device depend on the number of rows.

Figure 11:
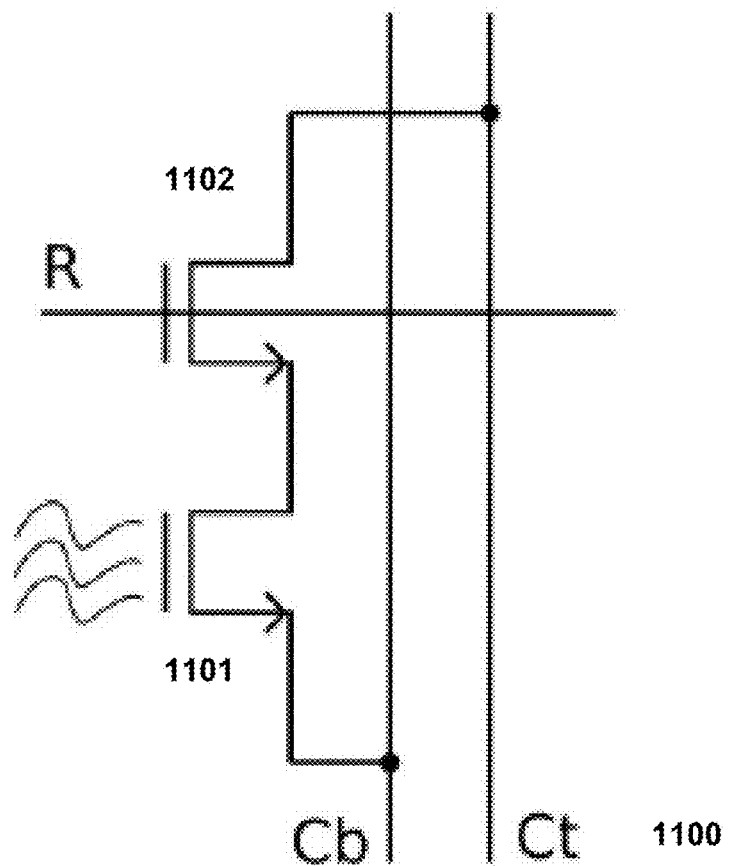
FIG. 11 shows a two-transistor (2T) pixel according to an embodiment of the present invention.

FIG. 11 shows a two-transistor (2T) pixel according to one embodiment of the present invention. As shown, the 2T pixel 1100 comprises an ISFET 1101 and a row selection device 1102. In the pixel 1100, the source of the ISFET 1101 is coupled to a column line Cb, the drain of the row selection device 1102 is coupled to a column line Ct, and the drain of the ISFET 1101 is coupled to the source of the row selection device 1102. The gate of the row selection device 1102 is coupled to a row line R.

Both ISFET 1101 and the row selection device 1102 are shown as NMOS, but other types of transistors may be used as well. The 2T pixel 1100 is configured as the source follower readout mode, although 2T pixels may be configured as the common source readout mode.

FIG. 12A to 12H illustrate more 2T pixel configurations according to embodiments of the present invention. In these Figures, "BE" stands for "with body effect", i.e. the ISFET is body-effected because the body terminal is connected to the analog supply voltage or analog ground voltage (depending on whether the ISFET transistor type is p-channel or n-channel MOS). The body effect is eliminated if the body terminal is connected to the source terminal of the transistor. "PR" stands for "PMOS devices in reversed positions", i.e. the positions of the p-channel ISFET and row selection device in the pixel circuit topology have been reversed (or switched around). "PNR" stands for "PMOS/NMOS devices in reversed positions", i.e. the positions of the p-channel ISFET and n-channel row selection device in the pixel circuit topology have been reversed (or switched around).

FIG. 12A illustrates a 2T pixel, according to one embodiment of the present invention. As shown, both the ISFET and the row selection device SEL are p-channel MOS transistors, with the source terminal of the ISFET coupled to the drain terminal of the row selection device. The drain terminal of the ISFET is connected to the analog ground voltage and the source terminal of the row selection device is connected to a current source, which provides a bias current to the pixel. The output voltage Vout is read out from the source terminal of the row selection device.

FIG. 12B illustrates a 2T pixel, according to one embodiment of the present invention. As shown, both the ISFET and the row selection device SEL are p-channel MOS transistors, with the source terminal of the ISFET connected to the body terminal to eliminate the body effect, and also connected to the drain terminal of the row selection device. The drain terminal of the ISFET is connected to the analog ground voltage and the source terminal of the row selection device is connected to a current source, which provides a bias current to the pixel. The output voltage Vout is read out from the source terminal of the row selection device.

FIG. 12C illustrates a 2T pixel, according to one embodiment of the present invention. As shown, both the ISFET and the row selection device SEL are p-channel MOS transistors, with the drain terminal of the ISFET connected to the source terminal of the row selection device. The drain terminal of the row selection device is connected to the analog ground voltage and the source terminal of the ISFET is connected to a current source. The output voltage Vout is read out from the source terminal of the ISFET.

FIG. 12D illustrates a 2T pixel, according to one embodiment of the present invention. As shown, both the ISFET and the row selection device SEL are p-channel MOS transistors, with the drain terminal of the ISFET connected to the source terminal of the row selection device. The drain of the row selection terminal is connected to the analog ground voltage and the source terminal of the ISFET is connected to a current source, which provides a bias current to the pixel. The output voltage Vout is read out from the source terminal of the ISFET. The source terminal of the ISFET is connected to the body terminal to eliminate the body effect.

FIG. 12E illustrates a 2T pixel, according to one embodiment of the present invention. As shown, the ISFET and the row selection device SEL are p-channel and n-channel MOS transistors respectively, with their source terminals connected together. The drain terminal of the ISFET is connected to the analog ground voltage and the drain of the row selection device is connected to a current source, which provides a bias current to the pixel. The output voltage Vout is read out from the drain terminal of the row selection device.

FIG. 12F illustrates a 2T pixel, according to one embodiment of the present invention. As shown, the ISFET and the row selection device SEL are p-channel and n-channel MOS transistors respectively, with their source terminals connected together. The drain terminal of the ISFET is connected to the analog ground voltage and the drain of the row selection device is connected to a current source, which provides a bias current to the pixel. The output voltage Vout is read out from the drain terminal of the row selection device. The source terminal of the ISFET is connected to the body terminal to eliminate the body effect.

FIG. 12G illustrates a 2T pixel, according to one embodiment of the present invention. As shown, the ISFET and the row selection device SEL are p-channel and n-channel MOS transistors respectively, with their drain terminals coupled together. The source terminal of the row selection device is connected to the analog ground voltage and the source terminal of the ISFET is connected to a current source, which provides a bias current to the pixel. The output voltage Vout is read out from the source terminal of the ISFET.

FIG. 12H illustrates a 2T pixel, according to one embodiment of the present invention. As shown, the ISFET and the row selection device SEL are p-channel and n-channel MOS transistors respectively, with their drain terminals coupled together. The source terminal of the row selection device is connected to the analog ground voltage and the source terminal of the ISFET is connected to a current source, which provides a bias current to the pixel. The output voltage Vout is read out from the source terminal of the ISFET. The source terminal of the ISFET is connected to the body terminal to eliminate the body effect.

Figures 13A, 13B, 13C, 13D:
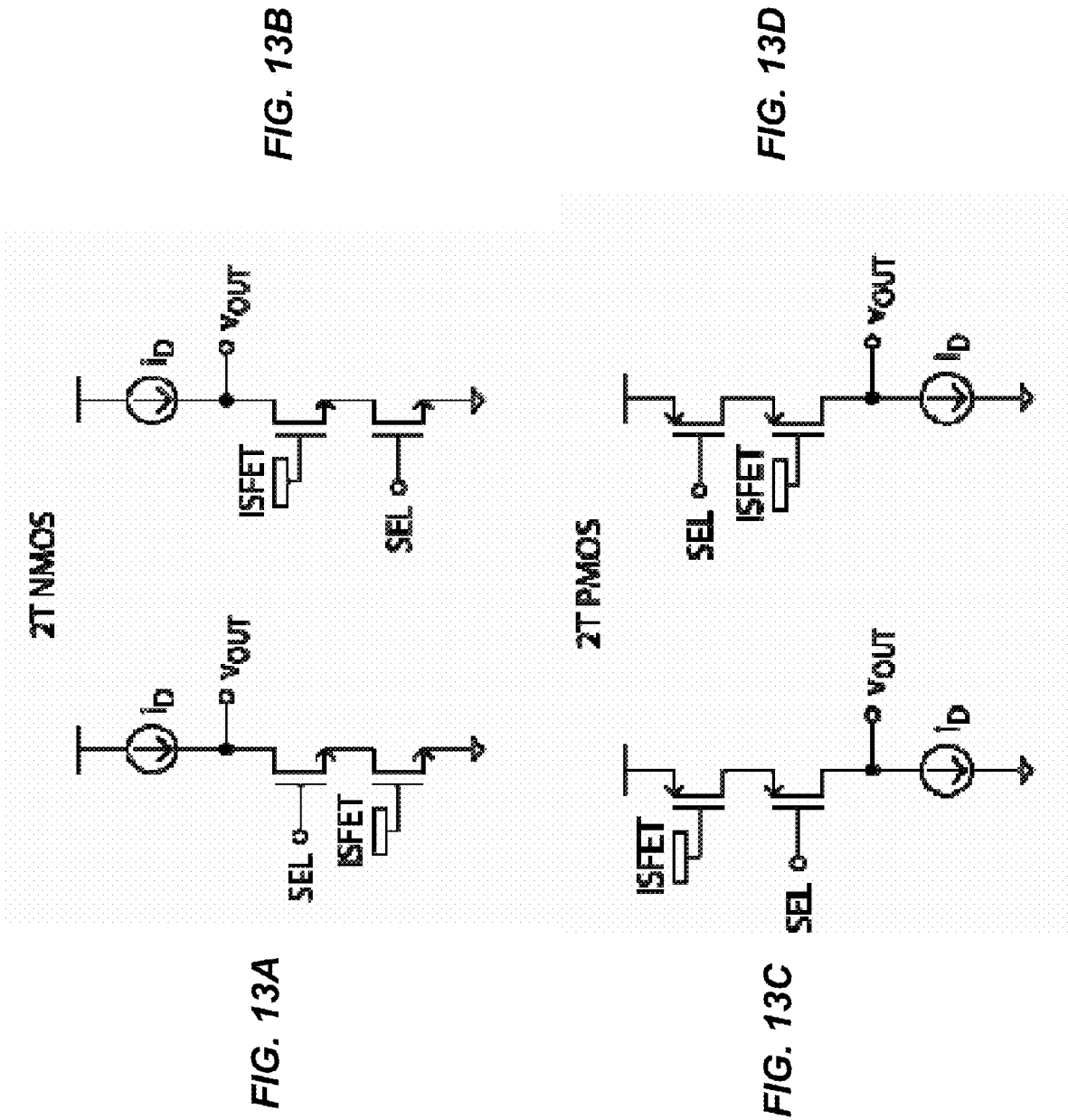
FIG. 13A to 13D illustrate common source 2T cell configurations according to embodiments of the present invention.

FIGS. 13A to 13D illustrate common source 2T cell configurations according to embodiments of the present invention. In FIGS. 13A and 13B, both the ISFET and the row selection device are n-channel MOS transistors, and in FIGS. 13C and 13D, both the ISFET and the row selection device are p-channel MOS transistors.

In FIG. 13A, the source terminal of the ISFET is connected to the analog ground supply and the drain terminal of the row selection device is connected to a current source, which provides a bias current to the pixel. The source terminal of the row selection device and the drain terminal of the ISFET are connected together. The output voltage Vout is read out from the drain terminal of the row selection device.

In FIG. 13B, the source terminal of the row selection device is connected to the analog ground supply and the drain terminal of the ISFET is connected to a current source, which provides a bias current to the pixel. The drain terminal of the row selection device and the source terminal of the ISFET are connected together. The output voltage Vout is read out from the drain terminal of the ISFET.

In FIG. 13C, the source terminal of the ISFET is connected to the analog supply voltage, and the drain terminal of the row selection device is connected to a current source, which provides a bias current to the pixel. The source terminal of the row selection device and the drain terminal of the ISFET are connected together. The output voltage Vout is read out from the drain terminal of the row selection device.

In FIG. 13D, the source terminal of the row selection device is connected to the analog supply voltage, and the drain terminal of the ISFET is connected to a current source, which provides a bias current to the pixel. The source terminal of the ISFET and the drain terminal of the row selection terminal are connected together. The output voltage Vout is read out from the drain terminal of the ISFET.

Figure 14A:
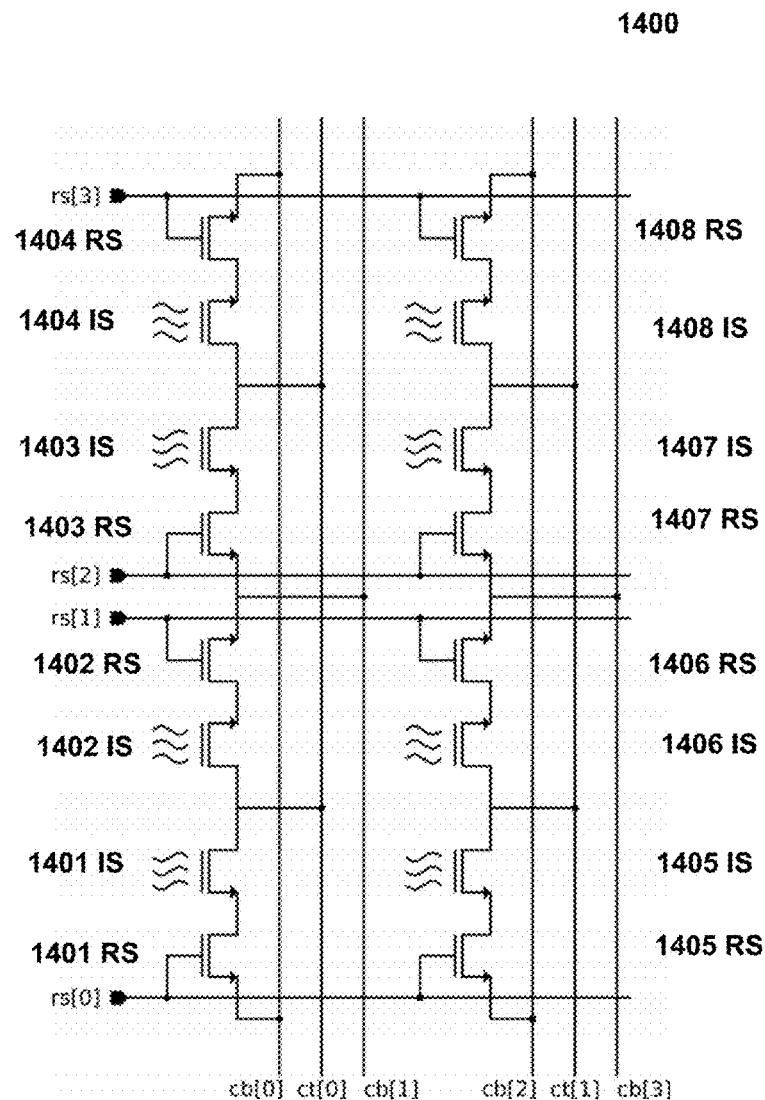
FIG. 14A shows a 2T pixel array according to an embodiment of the present invention.

FIG. 14A shows a 2T pixel array according to one embodiment of the present invention. For illustrative purposes, eight 2T pixels are shown arranged into two columns, though the 2T pixel array 1400 could extend to an array of any size of 2T pixels. Each column pitch contains three column lines cb[0], ct[0] and cb[1], The row lines rs[0], rs[1], rs[2] and rs[3], connect to all columns in parallel. A row selection device 1401RS and an ISFET 1401IS may form one 2T pixel, with the source of 1401IS connected to the drain of 1401RS. The source of 1401RS is connected to the column line cb[0], and the drain of 1401IS is connected to the column line ct[0]. The gate of 1401RS is connected to the row line rs[0). This pixel is mirrored in a pixel comprising 1402IS and 1402RS, with drains of 1401IS and 1402IS connected to the column line ct[0], and the gate of 1402RS connected to the row line rs[1]. The pixel comprising 1402IS and 1402RS is mirrored in a pixel comprising 1403IS and 1403RS, with the source of 1402RS and 1403RS connected to the row line cb[1], and the gate of 1403RS coupled to the row line rs[2]. The pixel comprising 1403IS and 1403RS is mirrored in a pixel comprising 1404IS and 1404RS, with the drains of 1403IS and 1404IS connected to the row line ct[0], the gate of 1404RS coupled to the row line rs[3], and the source of 1404RS coupled to the column line cb[0]. In the embodiment shown in FIG. 14, each of the IS devices is an ISFET and each of the RS devices is a row select device.

The right column, including a pixel consisting of 1405RS and 1405IS, a pixel consisting of 1406RS and 1406IS, a pixel consisting of 1407RS and 1407IS, and a pixel consisting of 1408RS and 1408IS, is coupled to column traces cb[2], ct[1], and cb[3] in substantially the same manner as described above.

Figures 14B, 14C:
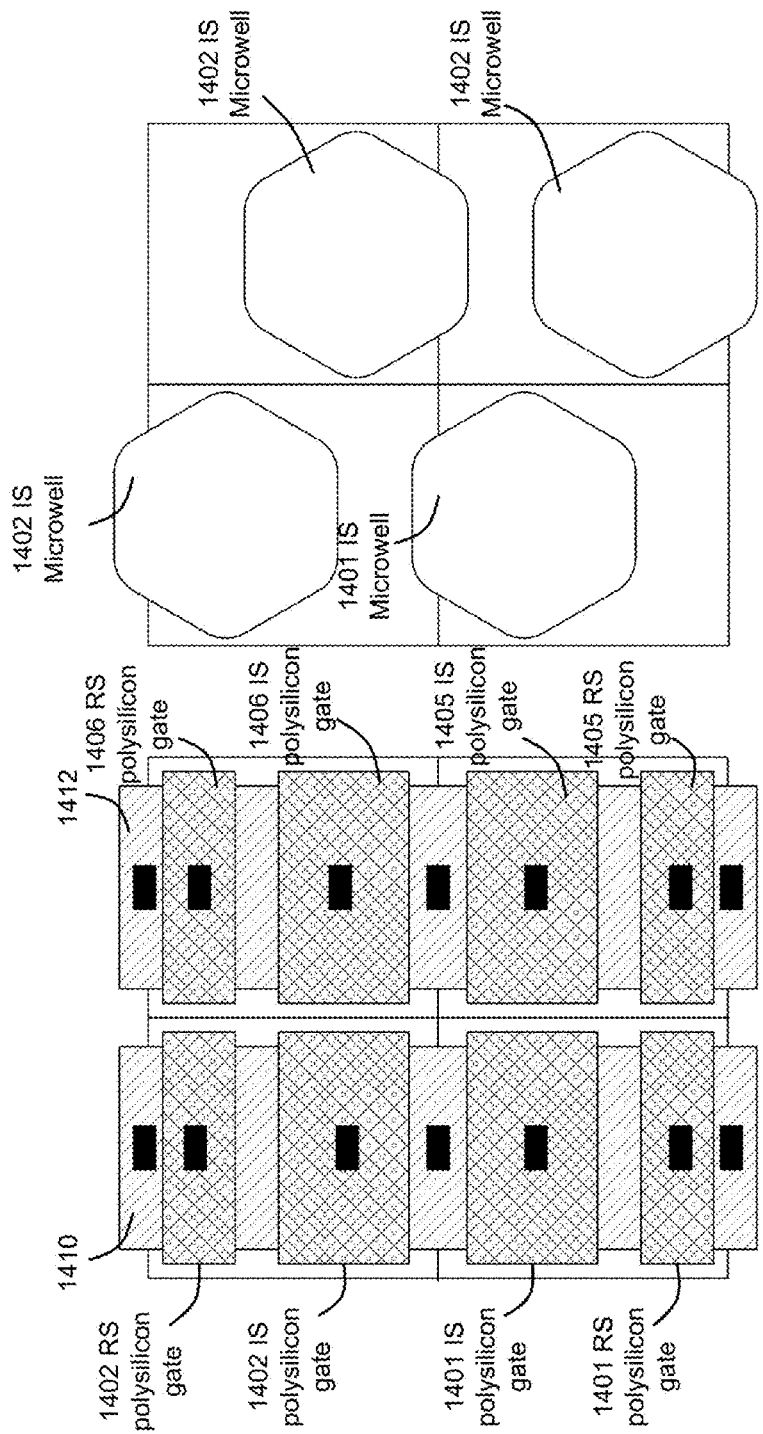
FIGS. 14B and 14C show a layout for a 2×2 2T pixel array according to an embodiment of the present invention.

FIGS. 14B and 14C show a layout for a 2×2 2T pixel array according to an embodiment of the present invention. The 2×2 2T pixel array may be part of the pixel array 1400. FIG. 14B shows that polysilicon gates for 1401RS, 1401IS, 1402RS and 1402IS may be placed on top of a continuous diffusion layer 1410 and polysilicon gates for 1405RS, 1405IS, 1406RS and 1406IS may be placed on top of a continuous diffusion layer 1412. In one embodiment, the continuous diffusion layers 1410 and 1412 may run from the top of the pixel array to the bottom of the pixel array. That is, the diffusion layer may have no discontinuities in the pixel array.

FIG. 14C shows where microwells for ISFETs 1401IS, 1402IS, 1405IS and 1406IS may be placed. The microwells may be used to hold analyte solutions that may be analyzed by the ISFETs. As shown in FIG. 14C, in one embodiment, the microwells may each have a hexagonal shape and stacked like a honeycomb. Further, in one embodiment, the contact may be placed directly on top of the gate structure. That is, the ISFETs may have a contact landed on polysilicon gate over thin oxide.

The pixel array 1400 has high density because of continuous diffusion, shared contacts, mirrored pixels, and one ct (column top) line and 2 cb (column bottom) line per physical column. A global bulk contact may be implemented by using a P+ wafer with P− epitaxy region.

The arrangement of pixel array 1400 provides for high speed operation. Row lines rs[0] and rs[1] are selected together and readout through cb[0] and cb[1]. This leads to a 4 times faster readout due to twice the number of pixels enabled for a single readout and half the parasitic load of a continuous array, allowing each column to settle twice as fast. In an embodiment, the full array is separated into a top half and a bottom half. This leads to another 4 times faster readout time due to twice the number of pixels readout at a time (both out the top and the bottom) and half the parasitic load of a continuous array. Thus, the total increase in speed over a single row selected continuous array is 16 times.

In an embodiment, both top and bottom halves of the pixel array may be enabled at the same time during readout. This can allow a multiplexing of readout between the top half and the bottom half. For example, one half can be doing a "wash" (e.g., flushing out reactants from the wells over the pixel devices) and the other half can be performing the readout. Once the other half is read, the readout for the two halves is switched.

In an embodiment, a 2T pixel design can incorporate two chemically-sensitive transistors (e.g., ISFETs) rather than one chemically-sensitive transistor and one row select device as described with respect to FIGS. 11-14. Both chemically-sensitive transistors, or ISFETs, can be NMOS or PMOS device and configured in a source follower or common source readout mode. Possible uses of such a 2T pixel may be where the first chemically-sensitive transistor has a different sensitivity to a particular analyte to that of the second chemically-sensitive transistor, allowing a local and in-pixel differential measurement to be made. Alternatively, both chemically-sensitive transistors may have the same sensitivity to a particular analyte, allowing a local and in-pixel average measurement to be made. These are among two examples of potential uses for this embodiment, and based on the description herein, a person of ordinary skill in the art will recognize other uses for the 2T pixel design that incorporate two chemically-sensitive transistors (e.g., ISFETs).

In one embodiment, a column circuit allows column lines to be swapped to a sampling circuit such that either source-side or drain-side row selection can be made in either source follower mode or common source mode.

Capacitive Charge Pump

One or more charge pumps may be used to amplify the output voltage from a chemically-sensitive pixel that comprises one or more transistors, such as those described above.

Figure 15:
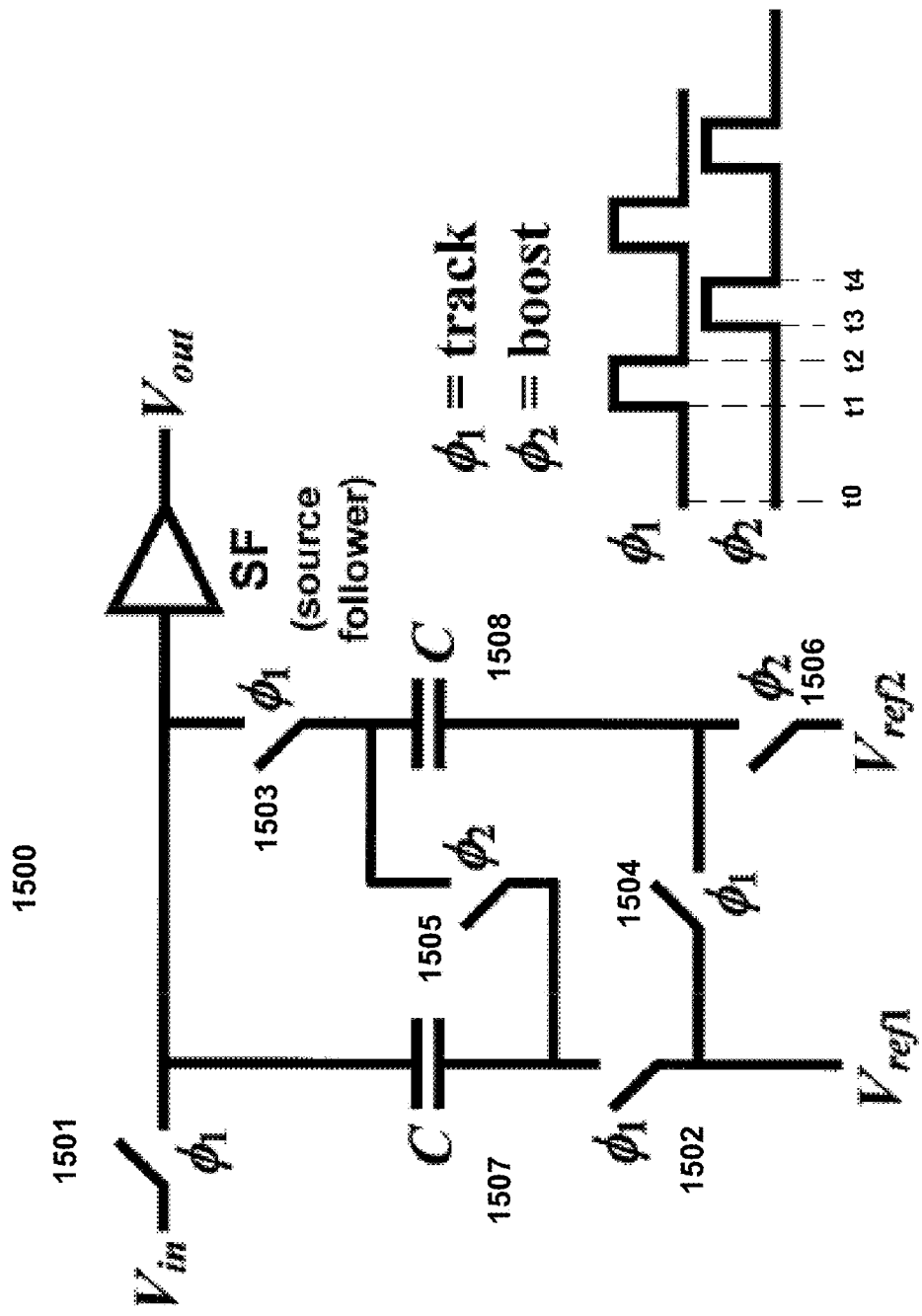
FIG. 15 shows a capacitive charge pump according to an embodiment of the present invention.

FIG. 15 shows a capacitive charge pump with a two times voltage gain according to one embodiment of the present invention. A charge pump 1500 may comprise φ1 switches 1501, 1502, 1503 and 1504, φ2 switches 1505 and 1506, and capacitors 1507 and 1508. Vref1 and Vref2 are set to obtain the desired DC offset of the output signal, and both are chosen to avoid saturation of the output during the boost phase. The operation of the charge pump may be controlled by timing signals, which may be provided by a timing circuit.

At time t0, all switches are off.

At time t1, φ1 switches 1501, 1502, 1503 and 1504 are turned on. The track phase may start. An input voltage Vin, which may be from an ion sensitive pixel, may start to charge capacitors 1507 and 1508.

At time t2, φ1 switches 1501, 1502, 1503 and 1504 are turned off, and capacitors 1507 and 1508 are charged to Vin−Vref1.

At time t3, φ2 switches 1505 and 1506 are turned on, while φ1 switches 1501, 1502, 1503 and 1504 remain off. The boost phase may start. The capacitor 1507 may start to discharge through the capacitor 1508. Since the capacitors are in parallel during the track phase and in series during the boost phase, and the total capacitance is halved during the boost phase while the total charge remains fixed, the voltage over the total capacitance must double, making Vout approximately two times Vin.

A source follower SF may be used to decouple the gain circuit from the following stage.

The charge pump 1500 may provide a two times gain without a noisy amplifier to provide a virtual ground.

Figure 16:
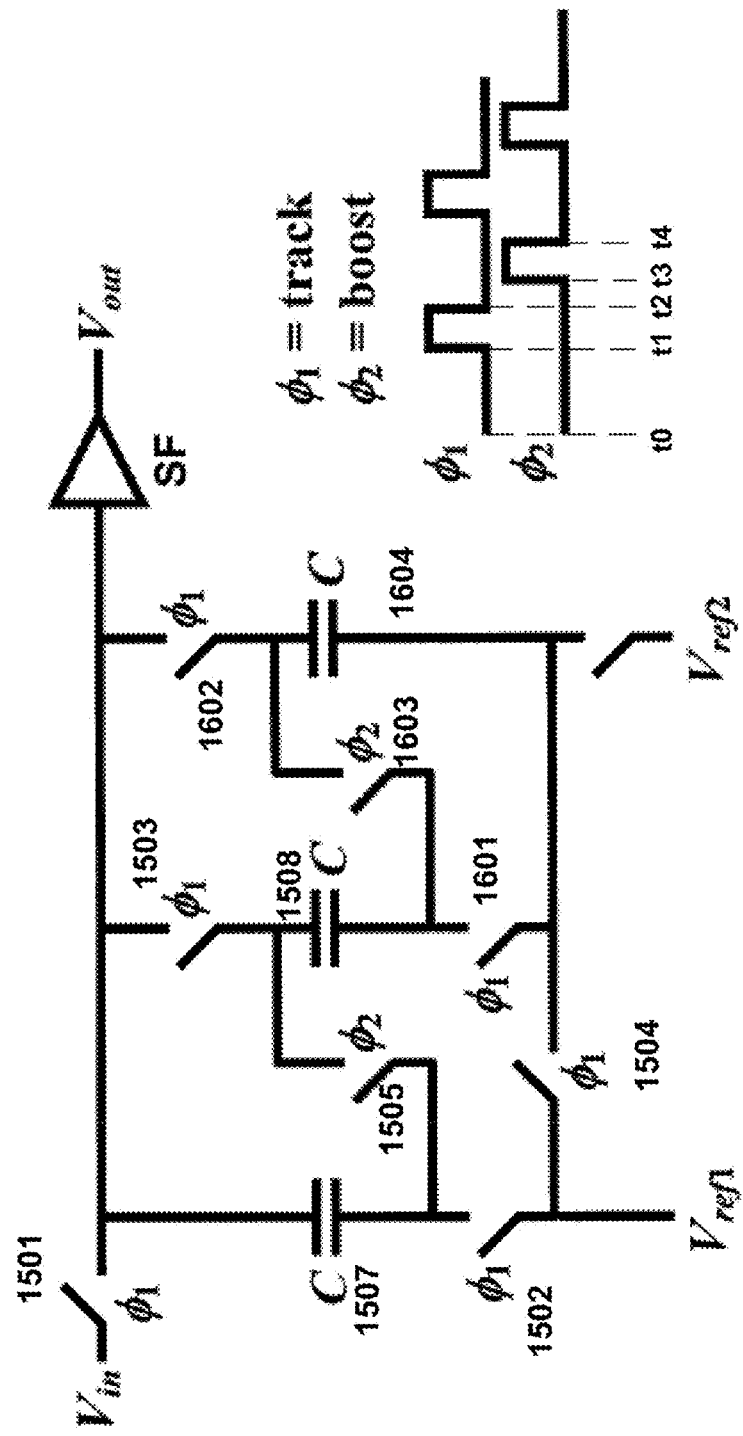
FIG. 16 shows a charge pump according to an embodiment of the present invention.

FIG. 16 shows a charge pump according to an embodiment of the present invention.

At time t0, all switches are off.

At time t1, φ1 switches 1501, 1502, 1503, 1504, 1601 and 1602 are turned on. The track phase may start. An input voltage Vin, which may be from an ion sensitive pixel, may start to charge capacitors 1507, 1508 and 1604.

At time t2, φ1 switches 1501, 1502, 1503, 1504, 1601 and 1602 are turned off, and capacitors 1507, 1508 and 1604 are charged to Vin−Vref1.

At time t3, φ2 switches 1505 and 1603 are turned on, while φ1 switches 1501, 1502, 1503, 1504, 1601 and 1602 remain off. The boost phase may start. The capacitor 1507 may start to discharge through the capacitors 1508 and 1604, and the capacitor 1508 may start to discharge through the capacitor 1604. Since the capacitors are in parallel during the track phase and in series during the boost phase, and the total capacitance is divided by three during the boost phase while the total charge remains fixed, the voltage over the total capacitance must triple, making Vout approximately three times Vin.

Figure 17:
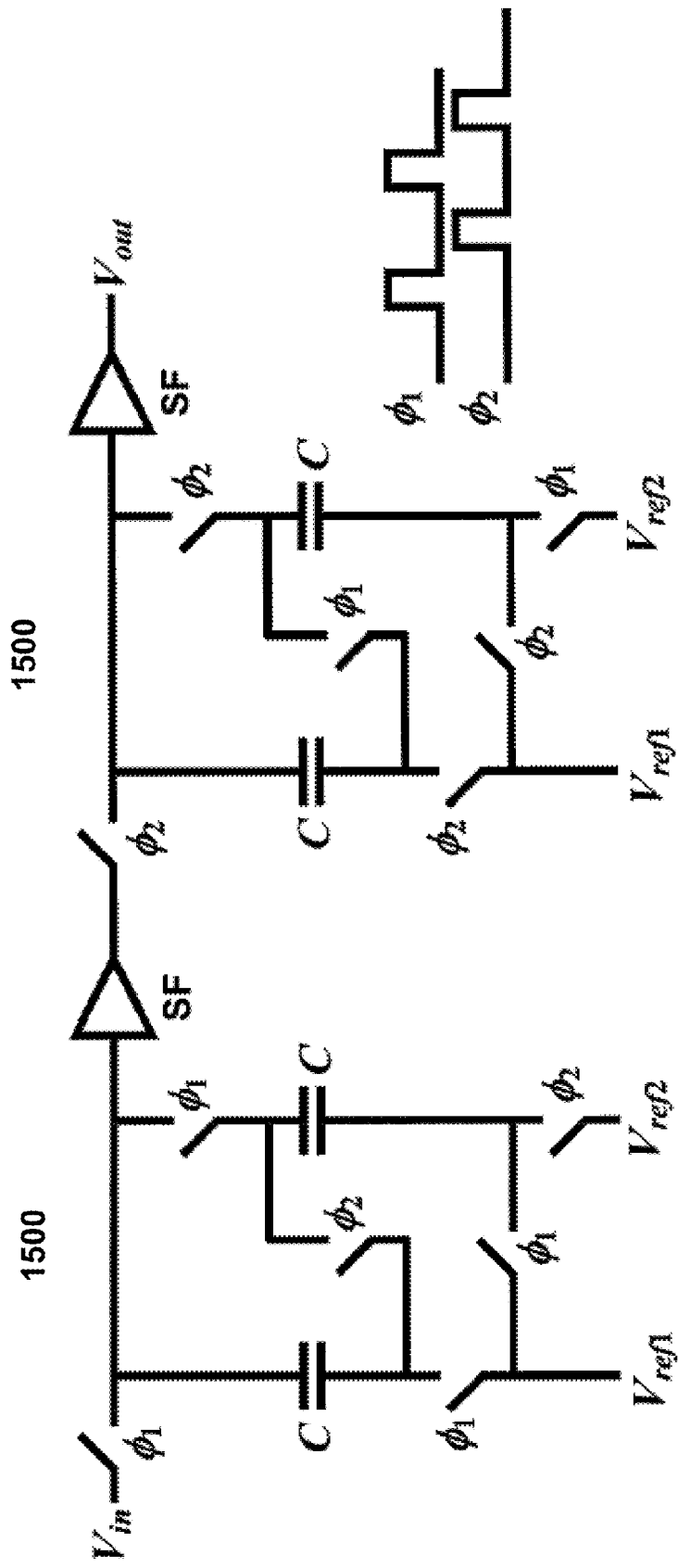
FIG. 17 shows a charge pump according to an embodiment of the present invention.

FIG. 17 shows an embodiment of a charge pump according to an embodiment of the present invention. Two charge pumps 1500 shown in FIG. 15 are connected in series, enabling gain pipelining and amplifying input voltage Vin by a factor of four.

Additional series charge pumps can be added to increase the gain further. In a multi-stage charge pump, the capacitor values do not have to be the same size from stage to stage. It can be observed that the total area consumed by capacitors increases with the square of the gain. Although this feature may, in some cases, be undesirable with respect to area usage, power consumption, and throughput, the charge pump can be used without these penalties when the total noise produced by the ion sensitive pixel and associated fluidic noise is larger than the charge pump KT/C noise when a reasonable capacitor size is used.

Figure 18:
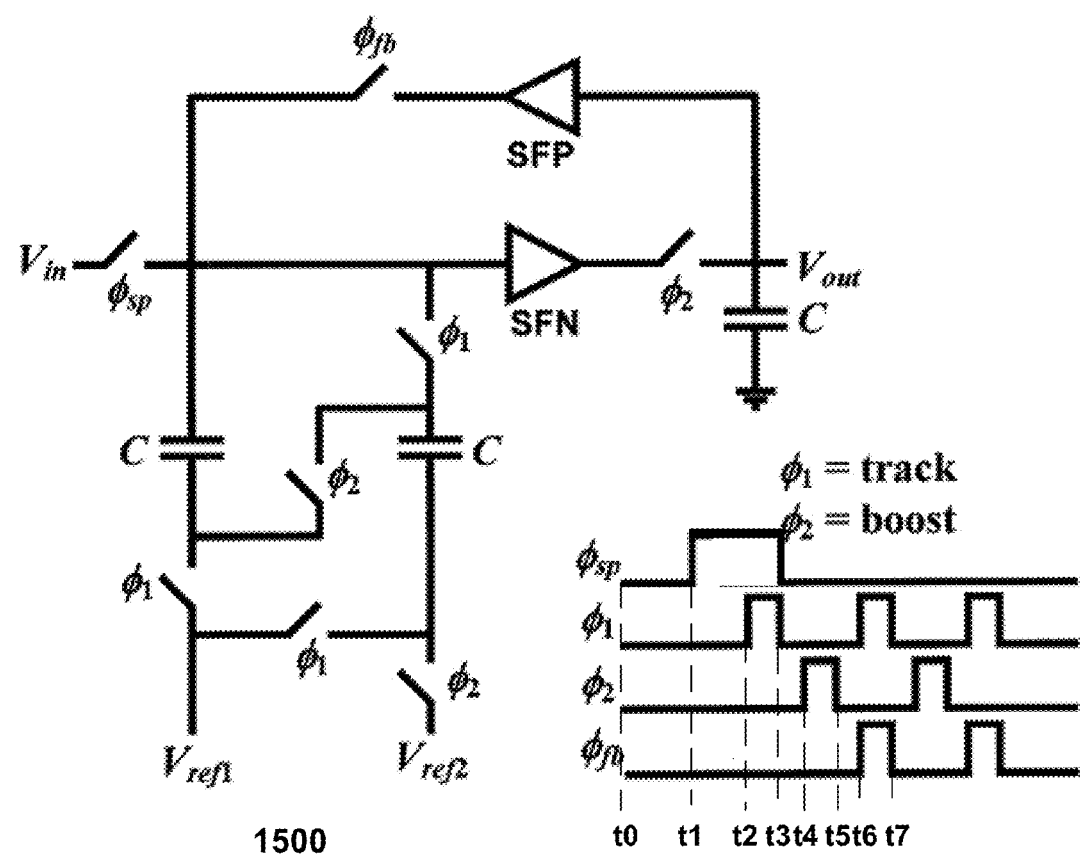
FIG. 18 shows a charge pump according to an embodiment of the present invention.

FIG. 18 shows an embodiment of a charge pump according to an embodiment of the present invention. A feedback path including a source follower SFP and a switch φfb is added to the charge pump 1500, feeding the output Vout back to the input of the charge pump.

At time t0, all switches are off.

At time t1, a switch φsp is on, providing an input voltage Vin to the input of the charge pump 1500.

From time t2 to time t5, the charge pump 1500 operates to push the output voltage Vout to 2(Vin−Vref1), as described before with reference to FIG. 15.

From time t6 to t7, the switch φfb is on, feeding the output voltage 2(Vin−Vref1). back to the input of the charge pump 1500, and the first cycle ends.

During the second cycle, the charge pump 1500 amplifies the output voltage by 2(2(Vin−Vref1)). The process repeats, with the output being amplified during each cycle.

CCD-Based Multi-Transistor Active Pixel Sensor Array

An ion sensitive MOS electrode is charge coupled to adjacent electrodes to facilitate both confinement and isolation of carriers. Measurements of ion concentration are made by discrete charge packets produced at each pixel and confined by potential barriers and wells. The ion sensitive electrode can act as either a barrier level or as a potential well. Working in the charge domain provides several benefits, including but not limited to: 1) increased signal level and improved signal to noise through the accumulation of multiple charge packets within each pixel, 2) better threshold matching of the MOS sensing and reference structures, 3) reduction in flicker noise, and 4) global-snap shot operation.

A floating electrode is used to detect ions in close proximity to the electrode. The electrode is charge coupled to other electrodes and to other transistors to form a pixel that can be placed into an array for addressable readout. It is possible to obtain gain by accumulating charge into another electrode or onto a floating diffusion (FD) node or directly onto the column line. It is desirable to achieve both a reduction in pixel size as well as increase in signal level. To reduce pixel size, ancillary transistors may be eliminated and a charge storage node with certain activation and deactivation sequences may be used.

The ion sensitive (IS) accumulation pixel contains some of the following concepts:
1. Electrodes are charge coupled to the IS electrode;
2. A source of carriers (electrons or holes) for charge packets;
3. A reference electrode to act as a barrier or a well for the charge packets;
4. A floating diffusion node for charge to voltage conversion;
5. Ancillary transistors to provide buffering and isolation for addressable readout; and
6. Sequences to eliminate some or all ancillary transistors depending on the application.

Figure 19:
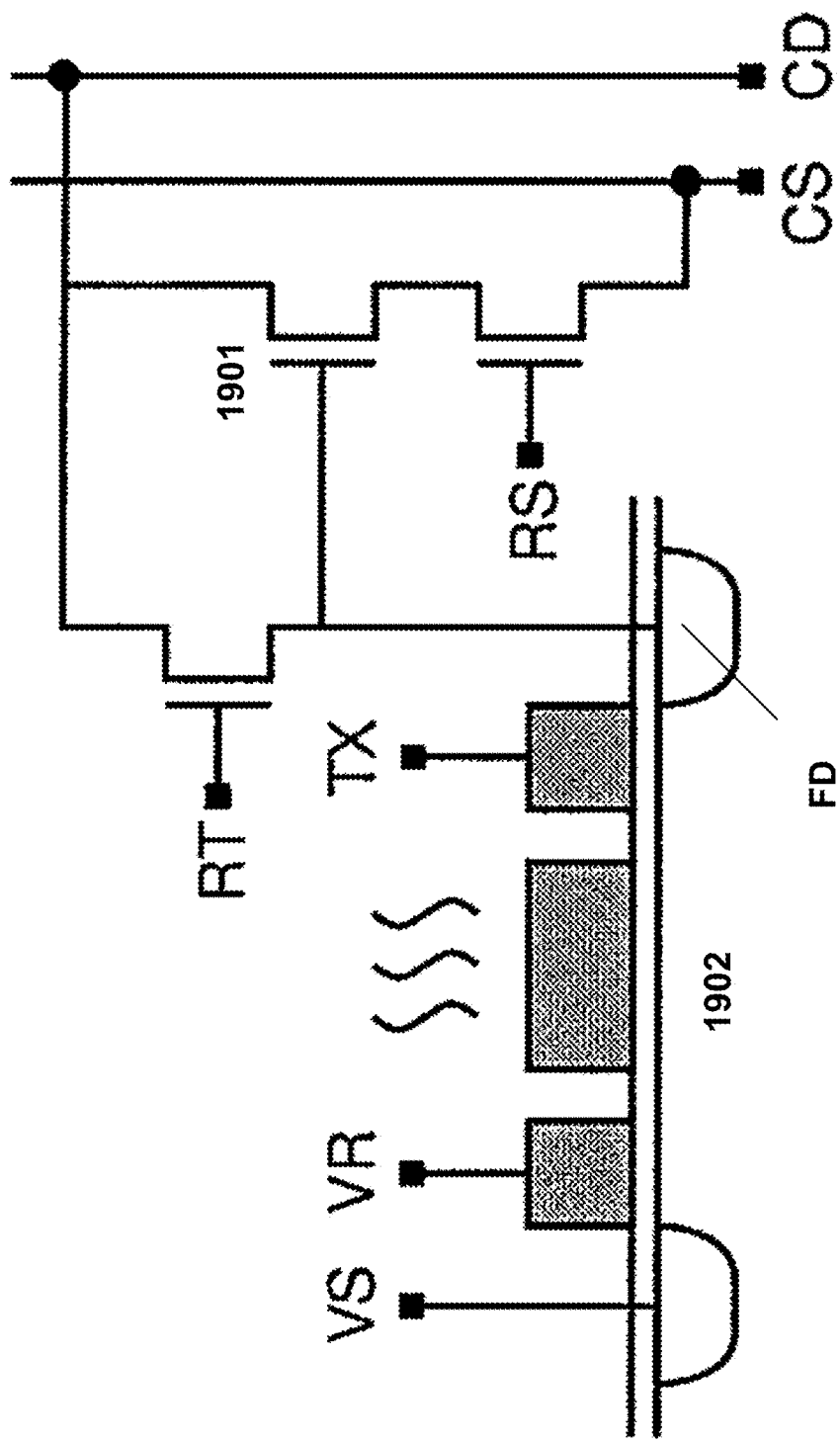
FIG. 19 shows a basic IS accumulation pixel according to an embodiment of the present invention.

The basic IS accumulation pixel is shown in FIG. 19. Charge accumulation can occur either locally at the time of readout or globally during a separate integration time. The embodiment shown in FIG. 19 is a three transistor three electrode (3T3E) pixel. The three transistors include a reset transistor RT, a source follower 1901 and a row selection transistor RS, and the three electrodes include an electrode VS, an electrode VR, and an ion sensitive electrode 1902. The pixel also includes a transfer gate TX. It is also possible to configure the IS accumulation pixel with additional elements to allow simultaneous accumulation and readout. This can be done, for example, by adding 2 more electrodes to pipeline the process. In the basic configuration, charge is accumulated onto the floating diffusion node that is connected to the source of the reset (RT) control gate. In a rolling shutter operation, the floating diffusion (FD) is reset to CD=VDD. The row is then selected and readout through the source follower enabled by row selection (RS). Next, charge is accumulated onto the FD node which discharged the parasitic capacitor. A second sample is then taken. The difference between the samples represents the ion concentration. The samples are correlated and taken relatively quickly in time. Therefore, the thermal noise of the readout circuit is eliminated and the 1/f noise is reduced. To operate in a global shutter mode, all FD nodes are simultaneously reset to VDD. Then charge is accumulated on each isolated FD node. After accumulation, each row is selected by enabling the RS gate. The signal value is readout on the column line with a load on the source follower. Next the pixel is reset and sampled again. The difference between the samples represents the ion concentration. The 1/f noise is reduced through the double sampling. However, the thermal reset noise is not eliminated because the reset value is uncorrelated in time. The thermal noise can be reduced by half the power by following the reset operation with a subthreshold reset before sampling. In general, the thermal noise is low compared to the signal due to the charge accumulation. A correlated reset scheme with global shutter is available in other configurations.

Figure 20:
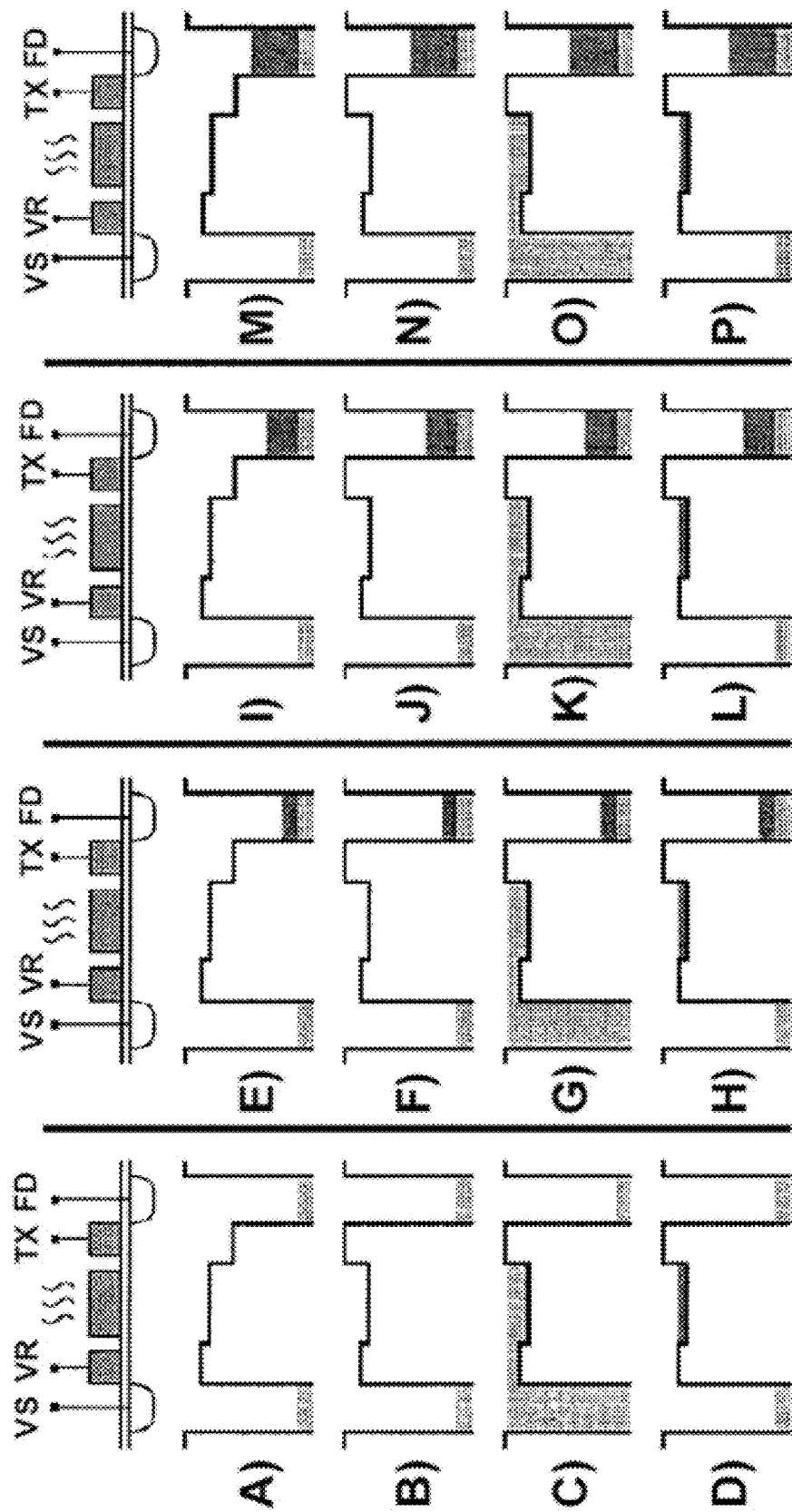

The basic charge accumulation scheme is shown in FIG. 20 using the surface potential diagrams. Only the electrodes are shown since the transistors are only used for readout. In each of these sequences, increasing potential is pointing down as is conventional to show potential wells containing electrons. Four cycles of charge accumulation are shown in FIG. 20 A-P. First, all charge is removed from the channel under the IS electrode and the channels are fully depleted using a high potential on FD (A). Next, the TX gate transitions to a low potential which creates the confinement barrier (B). A fill and spill operation is used to produce a charge packet proportional to the ion concentration at the IS electrode (C-D). In the next cycle, this charge packet is transferred to the FD node which discharges due to the electrons. The diagram shows electrons accumulating on the FD node, but the voltage is actually decreasing. After many cycles, as shown in FIG. 20 E-P, the signal to noise ratio is improved and the signal can be read out with gain. Hundreds to millions of cycles can be used to amplify the signal.

In alternative embodiments, the order of electrodes may be switched, and/or the IS electrode may be used as the barrier rather than the well. Transistors may be added to this accumulation line to enable a large array of pixels. The ancillary transistors are used to increase speed. However, it should be noted that no transistors are necessary to enable a full pixel array of the accumulation line. Instead, an array can be partitioned such that no transistors are needed. In an embodiment, the FD nodes are connected to the column line. Before a pixel is read out, the column line is reset to VDD. Then a row is selected by accumulating charge for that row directly onto the column line. After many cycles, the column discharges to a value directly proportional to the ion concentration. Since the capacitance of the column line depends on the total number of rows, the amount of accumulation required, depends on the number of rows. The array can be partitioned into sub arrays to make timing scalable. For example, every 100 rows can contain a local source follower buffer that is then connected to a global array. This hierarchical approach can be used in general with all readout schemes to make massive arrays of pixels with fast readout.

Due to the thermal activity of carriers, charge packets cannot be generated without noise. Each fill and spill operation produces charge error proportional to KTC (thermal noise in the floating diffusion capacitor), where C is equal to Cox times the area of the ion sensitive electrode. During the fill operation charge can flow freely between the source of electrons and the confinement well. However, during the spill operation, the device enters the subthreshold mode and carriers move by diffusion, mainly in only one direction, which results in half of the thermal noise of a resistive channel. The total noise in electrons for each charge packet is therefore $\sqrt{KTC/2}/q$ where q represents the charge of one electron in coulombs ($1.6 \times 10 e-19$). The signal in electrons is equal to VC/q. The signal to noise ratio after n cycles is equal to $V*\sqrt{2nC/KT}$. Note that the signal to noise ratio improves by the square root of the number of cycles of accumulation. For small signal levels, the amount of accumulation will be limited to the threshold mismatch between the VR reference electrode and the ion sensitive electrode. Since there is a reference electrode in every pixel and the electrodes are charge coupled, the relative threshold mismatch between each pair of electrodes is small. Assuming, this difference is about 1 mV, over 1000 accumulation cycles should be feasible, thereby improving the signal to noise by more than 30 times. By way of example, if the signal is 1 mV and the electrode area is 1 square micron with $Cox=5fF/um^2$, the signal to noise ratio after 1000 cycles is 50 to 1. Since the signal level then reaches 1V, it is expected that no other noise source is relevant. For clarity, the dominant noise is simply the charge packet thermal noise which is well known.

FIGS. 21 and 22 show the IS accumulation pixel with only 2 transistors. The selection transistor is eliminated by using a deactivation sequence after a row is read out. To deactivate, the FD node is discharged, which reduces the potential of the FD node and disables the source follower for that row. The surface potential diagrams for the pixel of FIG. 22 are shown in FIG. 23.

FIG. 24 shows the IS accumulation pixel with 2 transistors and 4 electrodes. This pixel produces the fill and spill charge packets and readout all at the same FD node. The 4th electrode allows global shutter operation and correlated double sampling. For faster readout, single sampling can be used if charge accumulation sufficiently reduces the 1/f noise contribution. FIG. 25 shows the surface potential diagrams for the basic operation of the pixel of FIG. 24.

FIG. 26 shows an IS accumulation pixel with 1 transistor and 3 electrodes. The channel can be depleted and supplied from the same node. This pixel depends on charge coupling, and signal range is lower than signal range for the other pixels.

Several design permutations are available depending on the desired mode of operation. The CCD channels are surface mode and are built in standard CMOS technology preferably below 0.13 um. Extra implants can be added to avoid surface trapping and other defects. A channel stop and channel can be formed from donor and acceptor impurity implants. The channel can be made of multiple implants to produce a potential profile optimal for the mode of operation.

FIG. 27 shows an embodiment of a three transistor (3T) active pixel sensor. The three transistors are a reset transistor 2701, a source follower 2702 and a row selection switch 2703. The reset transistor 2701 has a gate controlled by a reset signal RST, a source coupled to the floating diffusion (FD) of a pixel, and a drain connected to a fixed voltage. The source follower 2702 has its gate connected to the source of the reset transistor 2701, and its drain connected to a fixed voltage. A row selection transistor 2703 has its gate connected to a row line, its drain connected to a fixed voltage and its source connected to a column. Other electrodes interacting with the pixel includes a transfer gate TG, an ion selective electrode ISE, an input control gate ICG, and an input diffusion ID. These three elements form charge coupled electrodes that are operated in an identical way to VS, VR, and TX in FIG. 19.

FIG. 28 shows an alternate embodiment of a 3T active pixel sensor. The difference between the sensor in FIG. 28 and the sensor shown in FIG. 27 is that the sensor 2800 has a second input control gate ICG2, which allows more control over the potential barrier near the ion-sensitive electrode.

FIG. 29 shows an embodiment of a 3T active pixel sensor with a sample and hold circuit, which may be used to eliminate signal variations. As shown, the gate of the row selection transistor 2703 is controlled by a RowSelm signal provided by a row selection shift register. The source of the row selection transistor 2703 is coupled to a current sink ISink 2902 and a column buffer 2903. The current sink ISink 2902 may be biased by a voltage VB1 and the column buffer, which may be an amplifier, may be biased by a voltage VB2.

The sample and hold circuit 2901 may include a switch SH, a switch CAL, a capacitor Csh, and an amplifier Amp. The switch SH's input is coupled to the output of the column buffer 2903, and its output is coupled to a voltage VREF through the switch CAL, the upper part of the capacitor Csh, and the input of the amplifier Amp. The amplifier is biased by a voltage VB2. The output of the amplifier is coupled to a switch 2904 controlled by a signal ColSeln from a column selection shift register. The output of the switch 2904 is buffered by an output buffer 2905 before reaching the output terminal Vout. The output buffer is biased by a voltage VB3.

FIG. 30 shows an embodiment of a 3T active pixel sensor with a correlated double sampling circuit. The most significant difference between the sensor in FIG. 30 and that in FIG. 29 is that the former uses a correlated double sampling circuit 3001 to measure the signal from the column buffer 2903. An amplifier in the correlated double sampling circuit 3001 receives at its first input the output of the column buffer 2903 via a switch SH, and a capacitor Cin. The amplifier receives a reference voltage VREF at its second input, and is biased by the voltage VB2. A reset switch RST and a capacitor Cf are coupled in parallel with the amplifier.

FIG. 31 shows an embodiment of a 2.5T active pixel sensor used for a four pixel array. Each of the pixels has its own transfer transistor TX1, TX2, TX3 and TX4 and its own reset transistor. The drain of each transfer transistor is coupled to the source of the reset transistor in the same pixel, and the source of each transfer transistor is coupled to the gate of the source follower.

FIG. 32 shows an embodiment of a 1.75T active pixel sensor for a four pixel array. Each of the pixels has its own transfer transistor. The source of each transfer transistor is coupled to the floating diffusion of the same pixel, and the drain of each transfer transistor is coupled to the drain of the reset transistor RST of the sensor.

Several embodiments of the present invention are specifically illustrated and described herein. However, it will be appreciated that modifications and variations of the present invention are covered by the above teachings. In other instances, well-known operations, components and circuits have not been described in detail so as not to obscure the embodiments. It can be appreciated that the specific structural and functional details disclosed herein may be representative and do not necessarily limit the scope of the embodiments. For example, some embodiments are described with an NMOS. A skilled artisan would appreciate that a PMOS may be used as well.

Those skilled in the art may appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a computer-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disc Read Only Memory (CD-ROM), Compact Disc Recordable (CD-R), Compact Disc Rewriteable (CD-RW), optical disk, magnetic media, magneto-optical media, removable memory cards or disks, various types of Digital Versatile Disc (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

What is claimed is:

1. A device comprising:
a plurality of pairs of lines;
an array of pixels coupled to the plurality of pairs of lines, a given pixel in the array coupled to a first line and a second line of a given pair of lines, the given pixel comprising:
a chemically-sensitive field-effect transistor (chemFET) including a first terminal directly connected to the first line and directly connected to another chemically-sensitive field-effect transistor not in the given pixel, a second terminal, and a floating gate coupled to a passivation layer; and
a switch connected between the second terminal of the chemFET and the second line.

2. The device of claim 1, further comprising a readout circuit for reading the given pixel, the readout circuit comprising:
a bias circuit to apply a bias voltage to one of the first and second lines of the given pair of lines, and to apply the select signal to turn on the switch; and
a sense circuit to read the given pixel based on a voltage on the other of the first and second lines of the given pair of lines.

3. The device of claim 2, wherein the voltage indicates an ion-concentration of an analyte solution coupled to the chemFET of the given pixel.

4. The device of claim 2, wherein the sense circuit includes a pre-charge circuit to pre-charge the other of the first and second lines of the given pair to a pre-charge voltage prior to a read interval for the given pixel.

5. The device of claim 2, wherein the sense circuit includes a sample circuit to sample the voltage on the second line.

6. The device of claim 5, wherein the sample circuit includes a sample and hold circuit to hold an analog value of the voltage on the second line, and an analog to digital converter to convert the analog value to a digital value.

7. The device of claim 5, wherein the sample circuit includes an analog to digital converter to directly convert the voltage on the second line to a digital value.

8. The device of claim 2, the bias circuitry includes a current source coupled to the other of the first and second lines of the selected pair to provide a bias current to the given pixel during a read interval for the given pixel.

9. The device of claim 2, wherein the voltage on the other of the first and second lines is established based on a threshold voltage of the chemFET of the given pixel.

10. The device of claim 1, wherein the first terminal of the chemFET is a drain terminal, and the second terminal of the chemFET is a source terminal.

11. The device of claim 1, wherein the first terminal of the chemFET is a source terminal, and the second terminal of the chemFET is a drain terminal.

* * * * *